United States Patent
Wang

(10) Patent No.: US 11,631,897 B2
(45) Date of Patent: Apr. 18, 2023

(54) IONIC LIQUID ADDITIVE FOR LITHIUM-ION BATTERY

(71) Applicant: High Tech Battery Inc., Taipei (TW)

(72) Inventor: Kuei Yung Wang, Taipei (TW)

(73) Assignee: HIGH TECH BATTERY INC., Taipei (TW)

( * ) Notice: Subject to any disclaimer, the term of this patent is extended or adjusted under 35 U.S.C. 154(b) by 0 days.

(21) Appl. No.: 17/315,501

(22) Filed: May 10, 2021

(65) Prior Publication Data
US 2022/0238918 A1 Jul. 28, 2022

Related U.S. Application Data

(60) Provisional application No. 63/139,860, filed on Jan. 21, 2021.

(51) Int. Cl.
*H01M 10/0567* (2010.01)
*H01M 10/0525* (2010.01)
*H01M 10/0569* (2010.01)

(52) U.S. Cl.
CPC ... *H01M 10/0567* (2013.01); *H01M 10/0525* (2013.01); *H01M 10/0569* (2013.01); *H01M 2300/0025* (2013.01); *H01M 2300/0045* (2013.01)

(58) Field of Classification Search
None
See application file for complete search history.

(56) References Cited

U.S. PATENT DOCUMENTS

| 2016/0075952 | A1* | 3/2016 | Kim | B01D 11/04 |
| | | | | 208/326 |
| 2019/0020069 | A1* | 1/2019 | Moganty | H01M 10/0569 |

FOREIGN PATENT DOCUMENTS

| CN | 102222571 B | 10/2013 |
| CN | 110204473 A | 9/2019 |
| CN | 110429338 A | 11/2019 |
| CN | 110915037 A | 3/2020 |

(Continued)

OTHER PUBLICATIONS

United Kingdom Combined Search and Examination Report Under Section 17 and 18(3), dated Jun. 22, 2021, issued in corresponding UK Application No. GB2106863.0.

(Continued)

*Primary Examiner* — Jonathan Crepeau
*Assistant Examiner* — Angela J Martin
(74) *Attorney, Agent, or Firm* — OSTROLENK FABER LLP

(57) ABSTRACT

An ionic liquid additive for lithium-ion battery

An ionic liquid for adding to an electrolyte of a lithium-ion battery, the ionic liquid comprises a compound with a dual core structure having the general formula (I):

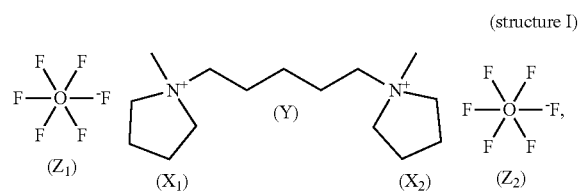

wherein each of cationic group $X_1$ and $X_2$ are heterocyclic aromatic and amine.

12 Claims, 31 Drawing Sheets

(56) References Cited

FOREIGN PATENT DOCUMENTS

| | | | |
|---|---|---|---|
| DE | 958 560 C | 2/1957 | |
| EP | 0 281 994 A1 | 9/1988 | |
| EP | 1 970 990 A1 | 9/2008 | |
| EP | 3 000 801 A1 | 3/2016 | |
| EP | 3000801 A1 * | 3/2016 | ............... C07C 7/20 |
| JP | 2005-026023 A | 1/2005 | |
| JP | 2005-032551 A | 2/2005 | |
| JP | 3974088 B2 | 9/2007 | |
| KR | 10-2139215 B1 | 7/2020 | |

OTHER PUBLICATIONS

Tong He, et al., "Stable, High-Efficiency Pyrrolidinium Based Electrolyte for Solid-State Dye-Sensitized Solar Cells" *ACS Applied Materials & interfaces*, vol. 7(39), 2015 pp. 21381-21390. ISSN: 1944-8244.

Jui-Cheng Chang, et al., "Synthesis and characterization of dicationic ionic liquids that contain both hydrophilic and hydrophobic anions" *Tetrahedron* vol. 66(32), 2010 pp. 6160-6155, ISSN: 0040-4020.

Tharanga Payagala, et al. "Unsymmetrical Dicationic Ionic Liquids: Manipulation Physicochemical Properties Using Specific Structural Architectures" *Chemistry of Materials* vol. 19(24), 2007 pp. 5848-5850, ISSN: 0897-4756.

Jared L. Anderson, et al., "Structure and Properties of High Stability Geminal Dicationic Ionic Liquids" *Journal of the American Chemical Society* vol. 127(2), 2005 pp. 593-604, ISSN: 0002-7863.

Guanglong Ding, et al., "A mechanistic study of geminal dicationic ionic liquids as mobile phase additives for improving the separation performance of high-performance liquid chromatography" *Analytical and Bioanalytical Chemistry* vol. 409(19) 2017 p. 4581-4592. ISSN: 1618-2642.

European Search Report, dated Nov. 10, 2021, issued in corresponding European Patent Application No. 21173764.8. Total 17 pages.

Martin Kubu, et al., "Three-Dimensional 10-Ring Zeolites: The Activities in Toluene Alkylation and Disproportionation," *Catalysis Today*, vol. 259, Jun. 23, 2015, pp. 97-106. XP055417068.

Wing-Leung Wong, et al., "A Green Catalysis of $CO_2$ Fixation to Aliphatic Cyclic Carbonates by a New Ionic Liquid System," Applied Catalysis A: General, vol. 472, Dec. 28, 2013, pp. 160-166. XP028667441.

Extended European Search Report, dated Jan. 26, 2022, issued in corresponding European Patent Application No. 21173764.8. Total 22 pages.

Tong He, et al., "Stable, High-Efficiency Pyrrolidinium-Based Electrolyte for Solid-State Dye-Sensitized Solar Cells," Applied Materials & Interfaces, vol. 7, No. 38, Sep. 3, 2015, pp. 21381-21390, XP 055855650.

Jared L. Anderson, et al., "Structure and Properties of High Stability Geminal Dicationic Ionic Liquids," Journal of the American Chemical Society, vol. 127, No. 2, Published on Web Dec. 23, 2004, pp. 593-604, XP009101530.

Zhengxi Zhang, et al., "Ionic Liquids Based on Aliphatic Tetraalkylammonium Dications and TFSI Anion as Potential Electrolytes," Journal of Power Sources, vol. 167, No. 1, Jan. 25, 2007, pp. 217-222, XP022016399.

Jorgen Fakstorp, et al., "Bifunctional Amines and Ammonium Compounds," Acta Chemica Scandinavica, vol. 11, No. 10, Jan. 1, 1957, pp. 1698-1705, XP008097067.

Kenneth T. Mecklenborg, "Synthesis of Possible Neuromuscular Blocking Agents Related to Succinylcholine," Journal of Organic Chemistry, Jan. 1, 1958, pp. 2023-2025, XP002774139.

Robert W. Jemison, et al., "Base-Catalysed Rearrangements Involving Ylide Intermediates. Part 8. The Preparation and Some Reactions of Stable Ammonium Ylides," Journal of the Chemical Society, Jan. 1, 1981, p. 1154, XP055879575.

Takeshi Oishi, et al., "Synthesis and Reaction of N-Methyl-N-tosylpyrrolidinium Perchlorate, a Selective Tosylating Reagent," Journal of the Chemical Society, Chemical Communications, No. 20, Jan. 1, 1972, p. 1148, XP055879687.

Application GB2106863.0 Supplementary Disclosures, Mar. 31, 2022.

First Office Action and Search Report, dated Sep. 29, 2021, issued in corresponding Taiwanese Patent Application No. 110118054.

Second Office Action, dated Dec. 6, 2021, issued in corresponding Taiwanese Patent Application No. 110118054.

Notice of Grant, dated Mar. 17, 2022, issued in corresponding Taiwanese Patent Application No. 110118054.

\* cited by examiner

Table 1: The synthesis parameters of bis(1-methylpyrrolidium) alkyl halide

| No. | Sample | Raw material X1 | Raw material Y | Reaction Temperature | Reaction Time |
|---|---|---|---|---|---|
| 1 | DiPYR$_{14}$Cl$_2$ | NMPD | 1,4-Dichlorobutane | 70°C | 16hr |
| 2 | DiPYR$_{15}$Cl$_2$ | NMPD | 1,5-Dichloropentane | 70°C | 16hr |
| 3 | DiPYR$_{16}$Cl$_2$ | NMPD | 1,6-Dichlorohexane | 70°C | 16hr |
| 4 | DiPYR$_{17}$Cl$_2$ | NMPD | 1,7-Dichloroheptane | 70°C | 16hr |
| 5 | DiPYR$_{18}$Cl$_2$ | NMPD | 1,8-Dichlorooctane | 70°C | 16hr |
| 6 | DiPYR$_{19}$Cl$_2$ | NMPD | 1,9-Dichlorononane | 70°C | 16hr |
| 7 | DiPYR$_{110}$Cl$_2$ | NMPD | 1,10-Dichlorodecane | 70°C | 16hr |
| 8 | DiPYR$_{1EE}$Cl$_2$ | NMPD | Bis(2-chloroethyl) ether | 70°C | 16hr |
| 9 | DiPYR$_{1EC}$Cl$_2$ | NMPD | Bis(2-chloroethyl) carbonate | 70°C | 16hr |
| 10 | DiPYR$_{1PO}$Cl$_2$ | NMPD | 1,5-dichloro pentan-3-one | 70°C | 16hr |
| 11 | DiPYR$_{1EB}$Cl$_2$ | NMPD | Bis(2-chloroethyl) butanedioate | 70°C | 16hr |
| Note | \multicolumn{5}{l}{1. NMPD: N-methyl pyrrolidine  2. The mixed mole ratio of NMPD to Alkyl halide is 2:1.1  3. Alkyl halide: Acetone = 1:1 vol.%} | | | | |

Figure 1

Table 2: The synthesis parameters of two-core cationic chain halide

| No. | Sample | Raw material X1 | Raw material X2 | Raw material Y | Mole ratio X1:X2:Y | Reaction Temperature | Reaction Time |
|---|---|---|---|---|---|---|---|
| 1 | DiPYR$_{15}$Cl$_2$ | NMPD | - | 1,5-Dichloropentane | 2:0:1.1 | 70°C | 16hr |
| 2 | DiPIP$_{15}$Cl$_2$ | MPIP | - | 1,5-Dichloropentane | 2:0:1.1 | 70°C | 16hr |
| 3 | DiTEA$_{15}$Cl$_2$ | TEA | - | 1,5-Dichloropentane | 2:0:1.1 | 70°C | 16hr |
| 4 | DiMIM$_{15}$Cl$_2$ | MIM | - | 1,5-Dichloropentane | 2:0:1.1 | 25°C | 12hr |
| 5 | PYRPIP$_{15}$Cl$_2$ | NMPD | MPIP | 1,5-Dichloropentane | 1:1:1.1 | 70°C | 16hr |
| 6 | PYRTEA$_{15}$Cl$_2$ | NMPD | TEA | 1,5-Dichloropentane | 1:1:1.1 | 70°C | 16hr |
| 7 | PYRMPE$_{15}$Cl$_2$ | NMPD | MPE | 1,5-Dichloropentane | 1:1:1.1 | 45°C | 12hr |
| 8 | PYRMIM$_{15}$Cl$_2$ | NMPD | MIM | 1,5-Dichloropentane | 1:1:1.1 | 25°C | 12hr |
| 9 | PYRPYO$_{15}$Cl$_2$ | NMPD | PYO | 1,5-Dichloropentane | 1:1:1.1 | 45°C | 12hr |
| 10 | PIPTEA$_{15}$Cl$_2$ | MPIP | TEA | 1,5-Dichloropentane | 1:1:1.1 | 70°C | 16hr |
| 11 | PIPMPE$_{15}$Cl$_2$ | MPIP | MPE | 1,5-Dichloropentane | 1:1:1.1 | 45°C | 12hr |
| 12 | PIPMIM$_{15}$Cl$_2$ | MPIP | MIM | 1,5-Dichloropentane | 1:1:1.1 | 25°C | 12hr |
| 13 | PIPPYO$_{15}$Cl$_2$ | MPIP | PYO | 1,5-Dichloropentane | 1:1:1.1 | 45°C | 12hr |
| 14 | TEAMPE$_{15}$Cl$_2$ | TEA | MPE | 1,5-Dichloropentane | 1:1:1.1 | 45°C | 12hr |
| 15 | TEAMIM$_{15}$Cl$_2$ | TEA | MIM | 1,5-Dichloropentane | 1:1:1.1 | 25°C | 12hr |
| 16 | TEAPYO$_{15}$Cl$_2$ | TEA | PYO | 1,5-Dichloropentane | 1:1:1.1 | 45°C | 12hr |
| 17 | MIMMPE$_{15}$Cl$_2$ | MIM | MPE | 1,5-Dichloropentane | 1:1:1.1 | 25°C | 12hr |
| 18 | MIMPYO$_{15}$Cl$_2$ | MIM | PYO | 1,5-Dichloropentane | 1:1:1.1 | 25°C | 12hr |
| Note | 1. NMPD: N-methyl pyrrolidine ; MPIP: N-methyl piperidine ; TEA: Triethylamine ; MIM: 1-methylimidazole ; MPE: Morpholine ; PYO: Pyrrole  2. Alkyl halide: Acetone = 1:1 vol.% | | | | | | |

Figure 2

Table 3: The synthesis parameters of two-core cationic chain ionic liquid

| No. | Sample | Raw material X1 | Raw material X2 | Raw material Y | Reaction temperature | Reaction time | Raw material Z1 | Raw material Z2 |
|---|---|---|---|---|---|---|---|---|
| 1 | DiPYR$_{14}$(PF$_6$)$_2$ | NMPD | NMPD | 1,4-Dichlorobutane | 70°C | 16hr | KPF$_6$ | KPF$_6$ |
| 2 | DiPYR$_{15}$(PF$_6$)$_2$ | NMPD | NMPD | 1,5-Dichloropentane | 70°C | 16hr | KPF$_6$ | KPF$_6$ |
| 3 | DiPYR$_{16}$(PF$_6$)$_2$ | NMPD | NMPD | 1,6-Dichlorohexane | 70°C | 16hr | KPF$_6$ | KPF$_6$ |
| 4 | DiPYR$_{18}$(PF$_6$)$_2$ | NMPD | NMPD | 1,8-Dichlorooctane | 70°C | 16hr | KPF$_6$ | KPF$_6$ |
| 5 | DiPIP$_{14}$(PF$_6$)$_2$ | MPIP | MPIP | 1,4-Dichlorobutane | 70°C | 16hr | KPF$_6$ | KPF$_6$ |
| 6 | DiPIP$_{15}$(PF$_6$)$_2$ | MPIP | MPIP | 1,5-Dichloropentane | 70°C | 16hr | KPF$_6$ | KPF$_6$ |
| 7 | DiPIP$_{16}$(PF$_6$)$_2$ | MPIP | MPIP | 1,6-Dichlorohexane | 70°C | 16hr | KPF$_6$ | KPF$_6$ |
| 8 | DiPIP$_{18}$(PF$_6$)$_2$ | MPIP | MPIP | 1,8-Dichlorooctane | 70°C | 16hr | KPF$_6$ | KPF$_6$ |
| 9 | DiPYR$_{14}$(PF$_6$)(BF$_4$) | NMPD | NMPD | 1,4-Dichlorobutane | 70°C | 16hr | KPF$_6$ | KBF$_4$ |
| 10 | DiPYR$_{15}$(PF$_6$)(BF$_4$) | NMPD | NMPD | 1,5-Dichloropentane | 70°C | 16hr | KPF$_6$ | KBF$_4$ |
| 11 | DiPYR$_{16}$(PF$_6$)(BF$_4$) | NMPD | NMPD | 1,6-Dichlorohexane | 70°C | 16hr | KPF$_6$ | KBF$_4$ |
| 12 | DiPYR$_{18}$(PF$_6$)(BF$_4$) | NMPD | NMPD | 1,8-Dichlorooctane | 70°C | 16hr | KPF$_6$ | KBF$_4$ |
| 13 | DiPIP$_{14}$(PF$_6$)(BF$_4$) | MPIP | MPIP | 1,4-Dichlorobutane | 70°C | 16hr | KPF$_6$ | KBF$_4$ |
| 14 | DiPIP$_{15}$(PF$_6$)(BF$_4$) | MPIP | MPIP | 1,5-Dichloropentane | 70°C | 16hr | KPF$_6$ | KBF$_4$ |
| 15 | DiPIP$_{16}$(PF$_6$)(BF$_4$) | MPIP | MPIP | 1,6-Dichlorohexane | 70°C | 16hr | KPF$_6$ | KBF$_4$ |
| 16 | DiPIP$_{18}$(PF$_6$)(BF$_4$) | MPIP | MPIP | 1,8-Dichlorooctane | 70°C | 16hr | KPF$_6$ | KBF$_4$ |
| 17 | PYRPIP$_{15}$(PF$_6$)$_2$ | NMPD | MPIP | 1,5-Dichloropentane | 70°C | 16hr | KPF$_6$ | KPF$_6$ |
| 18 | PYRTEA$_{15}$(PF$_6$)$_2$ | NMPD | TEA | 1,5-Dichloropentane | 70°C | 16hr | KPF$_6$ | KPF$_6$ |
| 19 | PYRMPE$_{15}$(PF$_6$)$_2$ | NMPD | MPE | 1,5-Dichloropentane | 45°C | 12hr | KPF$_6$ | KPF$_6$ |
| 20 | PYRMIM$_{15}$(PF$_6$)$_2$ | NMPD | MIM | 1,5-Dichloropentane | 25°C | 12hr | KPF$_6$ | KPF$_6$ |
| 21 | PYRPYO$_{15}$(PF$_6$)$_2$ | NMPD | PYO | 1,5-Dichloropentane | 45°C | 12hr | KPF$_6$ | KPF$_6$ |
| 22 | PIPTEA$_{15}$(PF$_6$)$_2$ | MPIP | TEA | 1,5-Dichloropentane | 70°C | 16hr | KPF$_6$ | KPF$_6$ |
| 23 | PIPMPE$_{15}$(PF$_6$)$_2$ | MPIP | MPE | 1,5-Dichloropentane | 45°C | 12hr | KPF$_6$ | KPF$_6$ |
| 24 | PIPMIM$_{15}$(PF$_6$)$_2$ | MPIP | MIM | 1,5-Dichloropentane | 25°C | 12hr | KPF$_6$ | KPF$_6$ |
| 25 | PIPPYO$_{15}$(PF$_6$)$_2$ | MPIP | PYO | 1,5-Dichloropentane | 45°C | 12hr | KPF$_6$ | KPF$_6$ |
| 26 | TEAMPE$_{15}$(PF$_6$)$_2$ | TEA | MPE | 1,5-Dichloropentane | 45°C | 12hr | KPF$_6$ | KPF$_6$ |
| 27 | TEAMIM$_{15}$(PF$_6$)$_2$ | TEA | MIM | 1,5-Dichloropentane | 25°C | 12hr | KPF$_6$ | KPF$_6$ |

Figure 3A

| # | Name | $X_1$ | $X_2$ | Solvent | Temp | Time | $Z_1$ | $Z_2$ |
|---|------|-----|-----|---------|------|------|-----|-----|
| 28 | TEAPYO$_{15}$(PF$_6$)$_2$ | TEA | PYO | 1,5-Dichloropentane | 45°C | 12hr | KPF$_6$ | KPF$_6$ |
| 29 | MIMMPE$_{15}$(PF$_6$)$_2$ | MIM | MPE | 1,5-Dichloropentane | 25°C | 12hr | KPF$_6$ | KPF$_6$ |
| 30 | MIMPYO$_{15}$(PF$_6$)$_2$ | MIM | PYO | 1,5-Dichloropentane | 25°C | 12hr | KPF$_6$ | KPF$_6$ |
| 31 | PYRPIP$_{15}$(PF$_6$)(BF$_4$) | NMPD | MPIP | 1,5-Dichloropentane | 70°C | 16hr | KPF$_6$ | KBF$_4$ |
| 32 | PYRTEA$_{15}$(PF$_6$)(BF$_4$) | NMPD | TEA | 1,5-Dichloropentane | 70°C | 16hr | KPF$_6$ | KBF$_4$ |
| 33 | PYRMPE$_{15}$(PF$_6$)(BF$_4$) | NMPD | MPE | 1,5-Dichloropentane | 45°C | 12hr | KPF$_6$ | KBF$_4$ |
| 34 | PYRMIM$_{15}$(PF$_6$)(BF$_4$) | NMPD | MIM | 1,5-Dichloropentane | 25°C | 12hr | KPF$_6$ | KBF$_4$ |
| 35 | PYRPYO$_{15}$(PF$_6$)(BF$_4$) | NMPD | PYO | 1,5-Dichloropentane | 45°C | 12hr | KPF$_6$ | KBF$_4$ |
| 36 | PIPTEA$_{15}$(PF$_6$)(BF$_4$) | MPIP | TEA | 1,5-Dichloropentane | 70°C | 16hr | KPF$_6$ | KBF$_4$ |
| 37 | PIPMPE$_{15}$(PF$_6$)(BF$_4$) | MPIP | MPE | 1,5-Dichloropentane | 45°C | 12hr | KPF$_6$ | KBF$_4$ |
| 38 | PIPMIM$_{15}$(PF$_6$)(BF$_4$) | MPIP | MIM | 1,5-Dichloropentane | 25°C | 12hr | KPF$_6$ | KBF$_4$ |
| 39 | PIPPYO$_{15}$(PF$_6$)(BF$_4$) | MPIP | PYO | 1,5-Dichloropentane | 45°C | 12hr | KPF$_6$ | KBF$_4$ |
| 40 | TEAMPE$_{15}$(PF$_6$)(BF$_4$) | TEA | MPE | 1,5-Dichloropentane | 45°C | 12hr | KPF$_6$ | KBF$_4$ |
| 41 | TEAMIM$_{15}$(PF$_6$)(BF$_4$) | TEA | MIM | 1,5-Dichloropentane | 25°C | 12hr | KPF$_6$ | KBF$_4$ |
| 42 | TEAPYO$_{15}$(PF$_6$)(BF$_4$) | TEA | PYO | 1,5-Dichloropentane | 45°C | 12hr | KPF$_6$ | KBF$_4$ |
| 43 | MIMMPE$_{15}$(PF$_6$)(BF$_4$) | MIM | MPE | 1,5-Dichloropentane | 25°C | 12hr | KPF$_6$ | KBF$_4$ |
| 44 | MIMPYO$_{15}$(PF$_6$)(BF$_4$) | MIM | PYO | 1,5-Dichloropentane | 25°C | 12hr | KPF$_6$ | KBF$_4$ |
| 45 | DiPYR$_{15}$(TFSI)(FSI) | NMPD | NMPD | 1,5-Dichloropentane | 70°C | 16hr | LiTFSI | LiFSI |
| 46 | DiPIP$_{15}$(TFSI)(FSI) | MPIP | MPIP | 1,5-Dichloropentane | 70°C | 16hr | LiTFSI | LiFSI |
| 47 | PYRPIP$_{15}$(TFSI)(FSI) | NMPD | MPIP | 1,5-Dichloropentane | 70°C | 16hr | LiTFSI | LiFSI |
| 48 | PYRTEA$_{15}$(TFSI)(FSI) | NMPD | TEA | 1,5-Dichloropentane | 70°C | 16hr | LiTFSI | LiFSI |
| 49 | PIPTEA$_{15}$(TFSI)(FSI) | MPIP | TEA | 1,5-Dichloropentane | 70°C | 16hr | LiTFSI | LiFSI |
| 50 | DiPYR$_{15}$(CF$_3$BF$_3$)(POF$_2$) | NMPD | NMPD | 1,5-Dichloropentane | 70°C | 16hr | LiCF$_3$BF$_3$ | LiPOF$_2$ |
| 51 | DiPIP$_{15}$(CF$_3$BF$_3$)(POF$_2$) | MPIP | MPIP | 1,5-Dichloropentane | 70°C | 16hr | LiCF$_3$BF$_3$ | LiPOF$_2$ |
| 52 | PYRPIP$_{15}$(CF$_3$BF$_3$)(POF$_2$) | NMPD | MPIP | 1,5-Dichloropentane | 70°C | 16hr | LiCF$_3$BF$_3$ | LiPOF$_2$ |
| 53 | PYRTEA$_{15}$(CF$_3$BF$_3$)(POF$_2$) | NMPD | TEA | 1,5-Dichloropentane | 70°C | 16hr | LiCF$_3$BF$_3$ | LiPOF$_2$ |
| 54 | PIPTEA$_{15}$(CF$_3$BF$_3$)(POF$_2$) | MPIP | TEA | 1,5-Dichloropentane | 70°C | 16hr | LiCF$_3$BF$_3$ | LiPOF$_2$ |
| Note | 1. NMPD: N-methyl pyrrolidine ; MPIP: N-methyl piperidine ; TEA: Triethylamine ; MIM: 1-methylimidazole ; MPE: Morpholine ; PYO: Pyrrole   2. Alkyl halide: Acetone = 1:1 vol.%   3. Raw material $X_1$:$X_2$:Y:$Z_1$:$Z_2$=1:1:1.1:1:1 (mol.) | | | | | | | |

Figure 3B

Table 4: The synthesis parameters of aromatic bonded to 1-methylpyrrolidinium halide

| No. | Sample | Raw material X1 | Raw material Y & W | Reaction Temperature | Reaction Time |
|---|---|---|---|---|---|
| 1 | Benzyl-PYR$_{1EE}$Cl | NMPD | Benzyl 2-chloro ethyl ether | 70°C | 12hr |
| 2 | Benzyl-PYR$_{1BE}$Cl | NMPD | Benzyl-4-chloro butyl ether | 70°C | 12hr |
| 3 | Benzoyl-PYR$_{11}$Cl | NMPD | Benzoyl chloride | 70°C | 12hr |
| 4 | Phenacyl-PYR$_{11}$Cl | NMPD | Phenacyl chloride | 70°C | 12hr |
| 5 | Furan-PYR$_{11}$Cl | NMPD | 2-Chlorofuran | 70°C | 12hr |
| 6 | Furan-PYR$_{14}$Cl | NMPD | 2-(4-chlorobutyl)furan | 70°C | 12hr |
| 7 | Furoyl-PYR$_{11}$Cl | NMPD | 2-Furoyl chloride | 70°C | 12hr |
| 8 | Benzenesulfonyl-PYR$_{11}$Cl | NMPD | Benzenesulfonyl chloride | 70°C | 12hr |
| 9 | p-Toluenesulfonyl-PYR$_{11}$Cl | NMPD | p-Toluenesulfonyl chloride | 70°C | 12hr |
| Note | 1. NPYR: N-methyl pyrrolidine<br>2. The mixed mole ratio of NPYR to aromatic halide is 1:1.1<br>3. Aromatic halide: Acetone = 1:1 vol.% | | | | |

Figure 4

Table 5: The synthesis parameters of aromatic bonded to cation halide

| No. | Sample | Raw material X1 | Raw material Y & W | Reaction Temperature | Reaction Time |
|---|---|---|---|---|---|
| 1 | Benzyl-PYR$_{1EE}$Cl | NMPD | Benzyl 2-chloro ethyl ether | 70°C | 12hr |
| 2 | Furan-PYR$_{14}$Cl | NMPD | 2-(4-chlorobutyl)furan | 70°C | 12hr |
| 3 | Furoyl-PYR$_{11}$Cl | NMPD | 2-Furoyl chloride | 70°C | 12hr |
| 4 | Benzyl-PIP$_{1EE}$Cl | MPIP | Benzyl 2-chloro ethyl ether | 70°C | 12hr |
| 5 | Furan-PIP$_{14}$Cl | MPIP | 2-(4-chlorobutyl)furan | 70°C | 12hr |
| 6 | Furoyl-PIP$_{11}$Cl | MPIP | 2-Furoyl chloride | 70°C | 12hr |
| 7 | Benzyl-TEA$_{1EE}$Cl | TEA | Benzyl 2-chloro ethyl ether | 70°C | 12hr |
| 8 | Furan-TEA$_{14}$Cl | TEA | 2-(4-chlorobutyl)furan | 70°C | 12hr |
| 9 | Furoyl-TEA$_{11}$Cl | TEA | 2-Furoyl chloride | 70°C | 12hr |
| 10 | Benzyl-MIM$_{1EE}$Cl | MIM | Benzyl 2-chloro ethyl ether | 25°C | 12hr |
| 11 | Furan-MIM$_{14}$Cl | MIM | 2-(4-chlorobutyl)furan | 25°C | 12hr |
| 12 | Furoyl-MIM$_{11}$Cl | MIM | 2-Furoyl chloride | 25°C | 12hr |
| 13 | Furoyl-MPE$_{11}$Cl | MPE | 2-Furoyl chloride | 45°C | 12hr |
| 14 | Furoyl-PYO$_{11}$Cl | PYO | 2-Furoyl chloride | 45°C | 12hr |
| Note | 1. NMPD: N-methyl pyrrolidine ; MPIP: N-methyl piperidine ; TEA: Triethylamine ; MIM: 1-methylimidazole ; MPE: Morpholine ; PYO: Pyrrole<br>2. Aromatic halide: Acetone = 1:1 vol.% | | | | |

Figure 5

Table 6: The synthesis parameters of aromatic bonded to cation ionic liquid

| No. | Sample | Raw material X1 | Raw material Y & W | Reaction Temperature | Reaction Time | Raw material Z1 |
|---|---|---|---|---|---|---|
| 1 | Benzyl-PYR$_{1EE}$PF$_6$ | NMPD | Benzyl 2-chloro ethyl ether | 70°C | 12hr | KPF$_6$ |
| 2 | Benzyl-PYR$_{1BE}$PF$_6$ | NMPD | Benzyl-4-chloro butyl ether | 70°C | 12hr | KPF$_6$ |
| 3 | Benzoyl-PYR$_{11}$PF$_6$ | NMPD | Benzoyl chloride | 70°C | 12hr | KPF$_6$ |
| 4 | Phenacyl-PYR$_{11}$PF$_6$ | NMPD | Phenacyl chloride | 70°C | 12hr | KPF$_6$ |
| 5 | Furan-PYR$_{11}$PF$_6$ | NMPD | 2-Chlorofuran | 70°C | 12hr | KPF$_6$ |
| 6 | Furan-PYR$_{14}$PF$_6$ | NMPD | 2-(4-chlorobutyl)furan | 70°C | 12hr | KPF$_6$ |
| 7 | Furoyl-PYR$_{11}$PF$_6$ | NMPD | 2-Furoyl chloride | 70°C | 12hr | KPF$_6$ |
| 8 | Benzenesulfonyl-PYR$_{11}$PF$_6$ | NMPD | Benzenesulfonyl chloride | 70°C | 12hr | KPF$_6$ |
| 9 | p-Toluenesulfonyl-PYR$_{11}$PF$_6$ | NMPD | p-Toluenesulfonyl chloride | 70°C | 12hr | KPF$_6$ |
| 10 | Benzyl-PIP$_{1EE}$PF$_6$ | MPIP | Benzyl 2-chloro ethyl ether | 70°C | 12hr | KPF$_6$ |
| 11 | Furan-PIP$_{14}$PF$_6$ | MPIP | 2-(4-chlorobutyl)furan | 70°C | 12hr | KPF$_6$ |
| 12 | Furoyl-PIP$_{11}$PF$_6$ | MPIP | 2-Furoyl chloride | 70°C | 12hr | KPF$_6$ |
| 13 | Benzyl-TEA$_{1EE}$PF$_6$ | TEA | Benzyl 2-chloro ethyl ether | 70°C | 12hr | KPF$_6$ |
| 14 | Furan-TEA$_{14}$PF$_6$ | TEA | 2-(4-chlorobutyl)furan | 70°C | 12hr | KPF$_6$ |
| 15 | Furoyl-TEA$_{11}$PF$_6$ | TEA | 2-Furoyl chloride | 70°C | 12hr | KPF$_6$ |
| 16 | Benzyl-MIM$_{1EE}$PF$_6$ | MIM | Benzyl 2-chloro ethyl ether | 25°C | 12hr | KPF$_6$ |
| 17 | Furan-MIM$_{14}$PF$_6$ | MIM | 2-(4-chlorobutyl)furan | 25°C | 12hr | KPF$_6$ |
| 18 | Furoyl-MIM$_{11}$PF$_6$ | MIM | 2-Furoyl chloride | 25°C | 12hr | KPF$_6$ |

Figure 6A

| 19 | Furoyl-MPE$_{11}$PF$_6$ | MPE | 2-Furoyl chloride | 45°C | 12hr | KPF$_6$ |
|----|----|----|----|----|----|----|
| 20 | Furoyl-PYO$_{11}$PF$_6$ | PYO | 2-Furoyl chloride | 45°C | 12hr | KPF$_6$ |
| 21 | Furoyl-PYR$_{11}$BF$_4$ | NMPD | 2-Furoyl chloride | 70°C | 12hr | KBF$_4$ |
| 22 | Furoyl-PYR$_{11}$FSI | NMPD | 2-Furoyl chloride | 70°C | 12hr | LiFSI |
| 23 | Furoyl-PYR$_{11}$TFSI | NMPD | 2-Furoyl chloride | 70°C | 12hr | LiTFSI |
| 24 | Furoyl-PYR$_{11}$CF$_3$BF$_3$ | NMPD | 2-Furoyl chloride | 70°C | 12hr | LiCF$_3$BF$_3$ |
| 25 | Furoyl-PYR$_{11}$POF$_2$ | NMPD | 2-Furoyl chloride | 70°C | 12hr | LiPOF$_2$ |
| 26 | Furoyl-PYR$_{11}$MeSO$_4$ | NMPD | 2-Furoyl chloride | 70°C | 12hr | KCH$_3$SO$_4$ |
| Note | 1. NMPD: N-methyl pyrrolidine ; MPIP: N-methyl piperidine ; TEA: Triethylamine ; MIM: 1-methylimidazole ; MPE: Morpholine ; PYO: Pyrrole  2. Aromatic halide: Acetone = 1:1 vol.%  3. Raw material X$_1$:(Y&W):Z$_1$=1:1.1:1 (mol.) | | | | | |

Figure 6B

Table 7. The maximum oxidation potential of electrolyte with the two-core structure ionic liquid at the LSV test

| No. | Sample | General formula of ionic liquid: $Z_1X_1YX_2Z_2$ | | | | | Maximum oxidation potential (V) |
|---|---|---|---|---|---|---|---|
| | | $X_1$ | $X_2$ | Y | $Z_1$ | $Z_2$ | |
| 1 | Organic Electrolyte | - | - | - | - | - | 4.652 |
| 2 | $DiPYR_{14}(PF_6)_2$ | NMPD | NMPD | butane, C4 | $PF_6$ | $PF_6$ | 4.906 |
| 3 | $DiPYR_{15}(PF_6)_2$ | NMPD | NMPD | pentane, C5 | $PF_6$ | $PF_6$ | 4.922 |
| 4 | $DiPYR_{16}(PF_6)_2$ | NMPD | NMPD | hexane, C6 | $PF_6$ | $PF_6$ | 4.872 |
| 5 | $DiPYR_{18}(PF_6)_2$ | NMPD | NMPD | octane, C8 | $PF_6$ | $PF_6$ | > 5.0 |
| 6 | $DiPIP_{15}(PF_6)_2$ | MPIP | MPIP | pentane, C5 | $PF_6$ | $PF_6$ | 4.895 |
| 7 | $DiPIP_{18}(PF_6)_2$ | MPIP | MPIP | octane, C8 | $PF_6$ | $PF_6$ | 4.963 |
| 8 | $DiPYR_{15}(PF_6)(BF_4)$ | NMPD | NMPD | pentane, C5 | $PF_6$ | $BF_4$ | > 5.0 |
| 9 | $DiPYR_{18}(PF_6)(BF_4)$ | NMPD | NMPD | octane, C8 | $PF_6$ | $BF_4$ | > 5.0 |
| 10 | $DiPIP_{15}(PF_6)(BF_4)$ | MPIP | MPIP | pentane, C5 | $PF_6$ | $BF_4$ | 4.955 |
| 11 | $DiPIP_{18}(PF_6)(BF_4)$ | MPIP | MPIP | octane, C8 | $PF_6$ | $BF_4$ | > 5.0 |
| 12 | $PYRPIP_{15}(PF_6)_2$ | NMPD | MPIP | pentane, C5 | $PF_6$ | $PF_6$ | 4.929 |
| 13 | $PYRTEA_{15}(PF_6)_2$ | NMPD | TEA | pentane, C5 | $PF_6$ | $PF_6$ | > 5.0 |
| 14 | $PYRMPE_{15}(PF_6)_2$ | NMPD | MPE | pentane, C5 | $PF_6$ | $PF_6$ | 4.653 |
| 15 | $PYRMIM_{15}(PF_6)_2$ | NMPD | MIM | pentane, C5 | $PF_6$ | $PF_6$ | - |
| 16 | $PYRPYO_{15}(PF_6)_2$ | NMPD | PYO | pentane, C5 | $PF_6$ | $PF_6$ | 4.782 |
| 17 | $PIPTEA_{15}(PF_6)_2$ | MPIP | TEA | pentane, C5 | $PF_6$ | $PF_6$ | 4.968 |
| 18 | $PIPMPE_{15}(PF_6)_2$ | MPIP | MPE | pentane, C5 | $PF_6$ | $PF_6$ | 4.372 |
| 19 | $PIPMIM_{15}(PF_6)_2$ | MPIP | MIM | pentane, C5 | $PF_6$ | $PF_6$ | - |

Figure 15A

| 20 | PIPPYO$_{15}$(PF$_6$)$_2$ | MPIP | PYO | pentane, C5 | PF$_6$ | PF$_6$ | 4.739 |
|---|---|---|---|---|---|---|---|
| 21 | TEAMPE$_{15}$(PF$_6$)$_2$ | TEA | MPE | pentane, C5 | PF$_6$ | PF$_6$ | 4.562 |
| 22 | TEAMIM$_{15}$(PF$_6$)$_2$ | TEA | MIM | pentane, C5 | PF$_6$ | PF$_6$ | - |
| 23 | TEAPYO$_{15}$(PF$_6$)$_2$ | TEA | PYO | pentane, C5 | PF$_6$ | PF$_6$ | 4.809 |
| 24 | MIMMPE$_{15}$(PF$_6$)$_2$ | MIM | MPE | pentane, C5 | PF$_6$ | PF$_6$ | - |
| 25 | MIMPYO$_{15}$(PF$_6$)$_2$ | MIM | PYO | pentane, C5 | PF$_6$ | PF$_6$ | - |
| 26 | PYRPIP$_{15}$(PF$_6$)(BF$_4$) | NMPD | MPIP | pentane, C5 | PF$_6$ | BF$_4$ | > 5.0 |
| 27 | PYRTEA$_{15}$(PF$_6$)(BF$_4$) | NMPD | TEA | pentane, C5 | PF$_6$ | BF$_4$ | > 5.0 |
| 28 | PYRPYO$_{15}$(PF$_6$)(BF$_4$) | NMPD | PYO | pentane, C5 | PF$_6$ | BF$_4$ | 4.833 |
| 29 | PIPTEA$_{15}$(PF$_6$)(BF$_4$) | MPIP | TEA | pentane, C5 | PF$_6$ | BF$_4$ | 4.928 |
| 30 | PIPPYO$_{15}$(PF$_6$)(BF$_4$) | MPIP | PYO | pentane, C5 | PF$_6$ | BF$_4$ | 4.76 |
| 31 | TEAPYO$_{15}$(PF$_6$)(BF$_4$) | TEA | PYO | pentane, C5 | PF$_6$ | BF$_4$ | 4.858 |
| 32 | DiPYR$_{15}$(TFSI)(FSI) | NMPD | NMPD | pentane, C5 | TFSI | FSI | 4.937 |
| 33 | DiPIP$_{15}$(TFSI)(FSI) | MPIP | MPIP | pentane, C5 | TFSI | FSI | 4.912 |
| 34 | PYRPIP$_{15}$(TFSI)(FSI) | NMPD | MPIP | pentane, C5 | TFSI | FSI | 4.938 |
| 35 | PYRTEA$_{15}$(TFSI)(FSI) | NMPD | TEA | pentane, C5 | TFSI | FSI | > 5.0 |
| 36 | PIPTEA$_{15}$(TFSI)(FSI) | MPIP | TEA | pentane, C5 | TFSI | FSI | 4.953 |
| 37 | DiPYR$_{15}$(CF$_3$BF$_3$)(POF$_2$) | NMPD | NMPD | pentane, C5 | CF$_3$BF$_3$ | POF$_2$ | > 5.0 |
| 38 | DiPIP$_{15}$(CF$_3$BF$_3$)(POF$_2$) | MPIP | MPIP | pentane, C5 | CF$_3$BF$_3$ | POF$_2$ | 4.935 |
| 39 | PYRPIP$_{15}$(CF$_3$BF$_3$)(POF$_2$) | NMPD | MPIP | pentane, C5 | CF$_3$BF$_3$ | POF$_2$ | > 5.0 |
| 40 | PYRTEA$_{15}$(CF$_3$BF$_3$)(POF$_2$) | NMPD | TEA | pentane, C5 | CF$_3$BF$_3$ | POF$_2$ | > 5.0 |
| 41 | PIPTEA$_{15}$(CF$_3$BF$_3$)(POF$_2$) | MPIP | TEA | pentane, C5 | CF$_3$BF$_3$ | POF$_2$ | 4.976 |
| 42 | DiPYR$_{15}$(BF$_4$)(FSI) | NMPD | NMPD | pentane, C5 | BF$_4$ | FSI | 4.962 |
| 43 | DiPIP$_{15}$(BF$_4$)(FSI) | MPIP | MPIP | pentane, C5 | BF$_4$ | FSI | 4.907 |

Figure 15B

| 44 | PYRPIP$_{15}$(BF$_4$)(FSI) | NMPD | MPIP | pentane, C5 | BF$_4$ | FSI | > 5.0 |
|---|---|---|---|---|---|---|---|
| 45 | PYRTEA$_{15}$(BF$_4$)(FSI) | NMPD | TEA | pentane, C5 | BF$_4$ | FSI | > 5.0 |
| 46 | PIPTEA$_{15}$(BF$_4$)(FSI) | MPIP | TEA | pentane, C5 | BF$_4$ | FSI | 4.974 |
| 47 | DiPYR$_{1EE}$(PF$_6$)$_2$ | NMPD | NMPD | diethyl ether | PF$_6$ | PF$_6$ | 4.774 |
| 48 | DiPYR$_{1EC}$(PF$_6$)$_2$ | NMPD | NMPD | diethyl carbonate | PF$_6$ | PF$_6$ | 4.825 |
| 49 | DiPYR$_{1PO}$(PF$_6$)$_2$ | NMPD | NMPD | pentan-3-one | PF$_6$ | PF$_6$ | 4.833 |
| 50 | DiPYR$_{1EB}$(PF$_6$)$_2$ | NMPD | NMPD | diethyl butanedioate | PF$_6$ | PF$_6$ | 4.706 |
| Note | \multicolumn{7}{l}{1. Organic Electrolyte: 1M LiPF6+EC:DMC:EMC=1:1:1 (vol.)+1 wt.%VC  2. NMPD: N-methyl pyrrolidine ; MPIP: N-methyl piperidine ; TEA: Triethylamine ; MIM: 1-methylimidazole ; MPE: Morpholine ; PYO: Pyrrole  3. The added amount of ionic liquid in the organic electrolyte: 10~15 wt.%  4. The maximum oxidation potential must be greater than 4.7 V, which can be considered to have an improvement.} |

Figure 15C

Table 8. The maximum oxidation potential of electrolyte with aromatic bonded to cation ionic liquid at the LSV test

| No. | Sample | General formula of ionic liquid: $Z_1X_1YW$ | | | Maximum oxidation potential (V) |
|---|---|---|---|---|---|
| | | $X_1$ | Y & W | $Z_1$ | |
| 1 | Organic Electrolyte | - | - | - | 4.652 |
| 2 | $PYR_{1BEE}PF_6$ | NMPD | Benzyl ethyl ether | $PF_6$ | 4.739 |
| 3 | $PYR_{1BBE}PF_6$ | NMPD | Benzyl butyl ether | $PF_6$ | 4.757 |
| 4 | $PYR_{1BZO}PF_6$ | NMPD | Benzoyl | $PF_6$ | 4.746 |
| 5 | $PYR_{1PHC}PF_6$ | NMPD | Phenacyl | $PF_6$ | 4.773 |
| 6 | $PYR_{1FRA}PF_6$ | NMPD | 2-Furan | $PF_6$ | 4.722 |
| 7 | $PYR_{14FRA}PF_6$ | NMPD | 2-ButylFuran | $PF_6$ | 4.736 |
| 8 | $PYR_{1FRO}PF_6$ | NMPD | 2-Furoyl | $PF_6$ | 4.829 |
| 9 | $PYR_{1BSF}PF_6$ | NMPD | Benzenesulfonyl | $PF_6$ | 4.817 |
| 10 | $PYR_{1TSF}PF_6$ | NMPD | p-Toluenesulfonyl | $PF_6$ | 4.801 |
| 11 | $PIP_{1BEE}PF_6$ | MPIP | Benzyl ethyl ether | $PF_6$ | 4.536 |
| 12 | $PIP_{14FRA}PF_6$ | MPIP | 2-ButylFuran | $PF_6$ | 4.622 |
| 13 | $PIP_{1FRO}PF_6$ | MPIP | 2-Furoyl | $PF_6$ | 4.729 |
| 14 | $TEA_{1BEE}PF_6$ | TEA | Benzyl ethyl ether | $PF_6$ | 4.389 |
| 15 | $TEA_{14FRA}PF_6$ | TEA | 2-ButylFuran | $PF_6$ | 4.443 |
| 16 | $TEA_{1FRO}PF_6$ | TEA | 2-Furoyl | $PF_6$ | 4.738 |
| 17 | $MIM_{1BEE}PF_6$ | MIM | Benzyl ethyl ether | $PF_6$ | - |
| 18 | $MIM_{14FRA}PF_6$ | MIM | 2-ButylFuran | $PF_6$ | - |
| 19 | $MIM_{1FRO}PF_6$ | MIM | 2-Furoyl | $PF_6$ | - |
| 20 | $MPE_{1FRO}PF_6$ | MPE | 2-Furoyl | $PF_6$ | - |
| 21 | $PYO_{1FRO}PF_6$ | PYO | 2-Furoyl | $PF_6$ | - |

Figure 16A

| 22 | PYR$_{1FRO}$BF$_4$ | NMPD | 2-Furoyl | BF$_4$ | 4.926 |
|---|---|---|---|---|---|
| 23 | PYR$_{1FRO}$FSI | NMPD | 2-Furoyl | FSI | 4.877 |
| 24 | PYR$_{1FRO}$TFSI | NMPD | 2-Furoyl | TFSI | 4.917 |
| 25 | PYR$_{1FRO}$CF$_3$BF$_3$ | NMPD | 2-Furoyl | CF$_3$BF$_3$ | 4.958 |
| 26 | PYR$_{1FRO}$POF$_2$ | NMPD | 2-Furoyl | POF$_2$ | 4.923 |
| 27 | PYR$_{1FRO}$MeSO$_4$ | NMPD | 2-Furoyl | MeSO$_4$ | 4.607 |
| Note | \multicolumn{5}{l|}{1. Organic Electrolyte: 1M LiPF6+EC:DMC:EMC=1:1:1 (vol.)+1 wt.%VC  2. NMPD: N-methyl pyrrolidine ; MPIP: N-methyl piperidine ; TEA: Triethylamine ; MIM: 1-methylimidazole ; MPE: Morpholine ; PYO: Pyrrole  3. The added amount of ionic liquid in the organic electrolyte: 1~10 wt.%  4. The maximum oxidation potential must be greater than 4.7 V, which can be considered to have an improvement} |

Figure 16B

Table 9. The composition of the electrolyte formulas

| No. | Film-forming agent (A) | | | | Stabilizer (B) | | Ionic liquid (C) | |
|---|---|---|---|---|---|---|---|---|
| | species 1 | content | species 2 | content | species | content | species | content |
| 1 | VC | 1% | - | - | - | - | - | - |
| 2 | VC | 1% | FEC | 1% | - | - | - | - |
| 3 | VC | 1% | FEC | 1% | EPFCP | 3% | - | - |
| 4 | VC | 1% | FEC | 1% | - | - | $PYR_{13}PF_6$ | 5% |
| 5 | VC | 1% | FEC | 1% | HFCP | 2.9% | $PYR_{13}PF_6$ | 5% |
| 6 | VC | 1% | FEC | 1% | EPFCP | 2.9% | $PYR_{13}PF_6$ | 5% |
| 7 | VC | 1% | FEC | 1% | EPFCP | 2.9% | $PYR_{13}PF_6$ | 10% |
| 8 | VC | 1% | FEC | 1% | EPFCP | 2.9% | $PYR_{13}PF_6$ | 15% |
| 9 | VC | 1% | FEC | 1% | - | - | $DiPYR_{15}(PF_6)_2$ | 6% |
| 10 | VC | 1% | FEC | 1% | HFCP | 2% | $DiPYR_{15}(PF_6)_2$ | 6% |
| 11 | VC | 1% | FEC | 1% | EPFCP | 2% | $DiPYR_{15}(PF_6)_2$ | 6% |
| 12 | VC | 1% | FEC | 1% | EPFCP | 2% | $DiPYR_{15}(PF_6)_2$ | 8% |
| 13 | VC | 1% | FEC | 1% | EPFCP | 2% | $DiPYR_{15}(PF_6)_2$ | 10% |
| 14 | VC | 2% | FEC | 1% | EPFCP | 2% | $DiPYR_{15}(PF_6)_2$ | 6% |
| 15 | VC | 3% | FEC | 1% | EPFCP | 2% | $DiPYR_{15}(PF_6)_2$ | 6% |

Figure 21A

| 16 | VC | 1% | FEC | 2% | EPFCP | 2% | DiPYR$_{15}$(PF$_6$)$_2$ | 6% |
|---|---|---|---|---|---|---|---|---|
| 17 | VC | 1% | FEC | 3% | EPFCP | 2% | DiPYR$_{15}$(PF$_6$)$_2$ | 6% |
| 18 | VC | 1% | FEC | 2% | EPFCP | 2.8% | Furoyl-PYR$_{11}$PF$_6$ | 6% |
| 19 | VC | 1% | FEC | 2% | EPFCP | 2.8% | DiPYR$_{15}$(PF$_6$)$_2$ | 6% |
| 20 | VC | 1% | FEC | 2% | EPFCP | 2.8% | DiPYR$_{1EE}$(PF$_6$)$_2$ | 6% |
| 21 | VC | 1% | FEC | 2% | EPFCP | 2.5% | PYRPIP$_{15}$(PF$_6$)$_2$ | 6% |
| 22 | VC | 1% | FEC | 2% | EPFCP | 2.5% | DiPIP$_{15}$(PF$_6$)$_2$ | 6% |
| 23 | VC | 1% | FEC | 2% | EPFCP | 2.5% | DiPYR$_{15}$(PF$_6$)(BF$_4$) | 6% |
| Note | 1. EC: Ethylene carbonate ; DMC: Dimethyl carbonate ; EMC: Methyl ethyl carbonate ; VC: Vinylene carbonate ; FEC: Fluoroethylene carbonate ; EPFCP: Ethoxy (pentafluoro) cyclotriphosphazene ; HFCP: Hexafluoro cyclotriphosphazene ; 2. The basic formula of the organic solvent in the electrolyte is EC:DMC:EMC=1:1:1, and then the film-forming agent, stabilizer and ionic liquid are added according to the weight percentage. The concentration of lithium salt LiPF$_6$ is 1 mole/L (M) for the total electrolyte. 3. The capacity of No. 1~8 is 40 Ah, and the capacity of No. 9~23 is 60 Ah. | | | | | | | |

Figure 21B

Table 10. The self-extinguishing time of various electrolyte formulations and its internal impedance and long-cycle performance of lithium-ion battery

| No. | Electrolyte SET (sec/g) | Lithium-ion battery ACIR (mΩ) | Lithium-ion battery 25°C Charge/Discharge cycle number |
|---|---|---|---|
| 1 | 63 | 3.27 | 1359 |
| 2 | 58 | 3.05 | 1492 |
| 3 | 45 | 2.92 | 1553 |
| 4 | 36 | 3.48 | 1265 |
| 5 | 22 | 3.12 | 1463 |
| 6 | 18 | 2.86 | 1620 |
| 7 | 8 | 3.28 | 1335 |
| 8 | 3 | 4.37 | 1065 |
| 9 | 27 | 3.05 | 1517 |
| 10 | 17 | 2.56 | 1662 |
| 11 | 11 | 2.37 | 1918 |
| 12 | 8 | 2.69 | 1739 |
| 13 | 6 | 3.05 | 1505 |
| 14 | 14 | 3.18 | 1554 |
| 15 | 13 | 4.06 | 1258 |
| 16 | 10 | 2.32 | 2035 |
| 17 | 8 | 2.45 | 1906 |

Figure 23A

| 18 | 14 | 2.63 | 1734 |
|---|---|---|---|
| 19 | 10 | 2.39 | 1895 |
| 20 | 11 | 2.15 | 2120 |
| 21 | 12 | 2.46 | 1887 |
| 22 | 13 | 2.43 | 1864 |
| 23 | 9 | 2.23 | 2117 |
| Note | 1. All formulas are tested by using a pouch cell of lithium iron battery<br>2. The internal impedance ACIR value of the battery is detected by HIOKI BT3561 battery internal resistance meter<br>3. Long-cyclic charge and discharge conditions: cut-off voltage 2.5-3.6 V, charge 0.5C CC-CV / discharge 0.5C, the capacity retention of 80%<br>4. The capacity of No. 1~8 is 40 Ah, and the capacity of No. 9~23 is 60 Ah. | | |

Figure 23B

IONIC LIQUID ADDITIVE FOR LITHIUM-ION BATTERY

CROSS-REFERENCE TO RELATED APPLICATION

The present application claims priority to U.S. Provisional Application No. 63/139,860, filed Jan. 21, 2021, the entire disclosure of which is incorporated by reference herein.

FIELD OF THE INVENTION

The present invention relates to an additive to an electrolyte for lithium-ion battery, in particular but not limited to an ionic liquid as an additive to the electrolyte.

BACKGROUND OF THE INVENTION

In recent years, the demand for batteries with high power, high energy density and long cyclic stability has increased with the rapid development of the application of lithium-ion batteries in power battery systems. Due to the continuous pursuit for high-energy density batteries, the use of electrodes with high-areal density and high-compaction density is currently one of the common methods in the industry. However, a resulting problem would be that the diffusion of lithium ions in the electrode becomes unsatisfactory. Furthermore, the interface impedance between the positive and negative electrodes increases, leading to greater polarization of the battery on the average voltage difference between charging and discharging curves, which makes the battery performance worse.

During the formation of lithium-ion batteries, a solid electrolyte interface (SEI) layer is formed on the surface of the anode, which controls the passage of lithium ions. When the formed SEI film is too thick and the impedance is high, lithium ions cannot migrate and penetrate, it will result in lithium precipitation. When the SEI film is not sufficiently dense and stable, it will dissolve gradually or may rupture during the charging and discharging processes, exposing the negative electrode and permitting its chemical reaction with the electrolyte. This brings about a continual decrease in the capacity of battery as the electrolyte is consumed by reacting with the negative electrode.

Another relatively prominent problem with lithium-ion batteries would be the increase of internal temperature of the battery due to improper heating, overcharging, puncture damage, etc. Puncture damage will result in short circuit when the positive and negative electrodes are in contact. It may not be possible to suppress the rise in internal temperature of the battery and this is likely to result in the decomposition of the SEI film and electrolytes. During the decomposition, $H_2$, $O_2$, HF, $PF_5$ and other active flammable compounds are produced. When the temperature rises to 200° C., the decomposition reaction of electrolytes and cathode materials will be occurred. Such decomposition reaction generates large amount of hydrogen, oxygen, and fluoride, leading to potential fire and explosion hazards. The performance and thermal safety of a lithium-ion battery depends on a lot which includes but not exclusively the cathode/anode materials, the property of the electrolyte as well as their relationship with the SEI layer on the surface of electrode.

An ionic liquid is a molten salt composed of anion and cation, which still exhibits a liquid state below 100° C. It has low volatility, high melting point, high ionic conductivity, a wide potential window and is a good flame retardant. With the aforementioned, it is a reasonable candidate of electrolyte additives for lithium-ion batteries. However, most of the ionic liquids are readily intercalated into the layer structure of graphite on the surface of the anode during the battery charging process, thereby increasing the impedance resistance of the SEI layer and results in severe generation of lithium precipitation. The resulting battery exhibits poor cyclic performance. Even with the presence of film-forming agent and stabilizer, inhibition of the intercalation effect is limited and the generation of the lithium precipitation is unavoidable.

SUMMARY OF THE INVENTION

In the first aspect of the invention there is provided an ionic liquid for adding to an electrolyte of a lithium-ion battery, the ionic liquid comprises a compound with a dual core structure having the general formula (I):

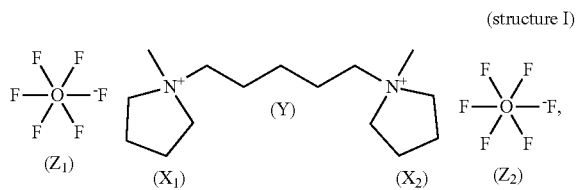

(structure I)

wherein each of cationic group $X_1$ and $X_2$ are heterocyclic aromatic and amine. Preferably, the heterocyclic aromatic is selected from a group consisting piperidinium, pyrrolidinium, pyrazolium and pyridinium.

More preferably, the amine is selected from a group consisting quaternary ammonium, azepane and phosphonium.

Yet more preferably, $X_1$ and $X_2$ is selected from a group consisting of:

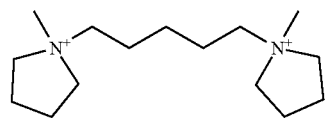 [SMILES: C[N+]1(CCCCC[N+]2(C)CCCC2)CCCC1]

1,5 Bis(1-methylpyrrolidium 1-yl) pentane

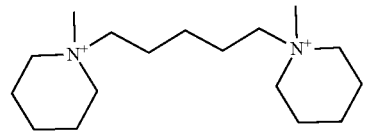 [SMILES: C[N+]1(CCCCC[N+]2(C)CCCCC2)CCCCC1]

1,5 Bis(1-methylpiperidinium 1-yl) pentane

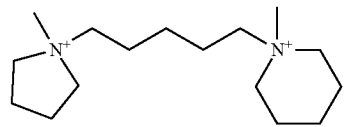 [SMILES: C[N+]1(CCCCC[N+]2(C)CCCC2)CCCCC1]

1,5 (1-methylpyrrolidium 1-yl) (1-methylpiperidinium 1-yl) pentane

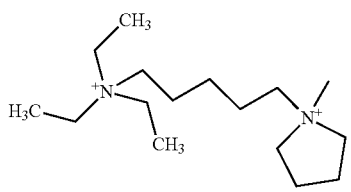 [SMILES: CC[N+](CC)(CC)CCCCC[N+]1(C)CCCC1]

1,5-[(1-methylpyrrolidium 1-yl) (triethylamine N-yl)] pentane

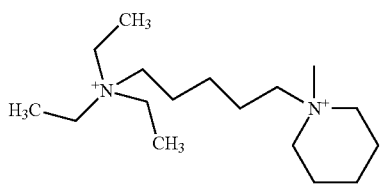 [SMILES: CC[N+](CC)(CC)CCCCC[N+]1(C)CCCCC1]

1,5-[(1-methylpiperidinium 1-yl) (triethylamine N-yl)] pentane

Preferably, the heterocyclic aromatic does not include imidazolium and morpholinium.

More preferably, $X_1$ and $X_2$ comprises two different functional group.

Yet more preferably, Y is any one of C3~C10 alkyl group.

Advantageously, $X_1YX_2$ is selected from a group consisting:

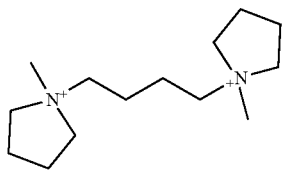 [SMILES: C[N+]1(CCCC[N+]2(C)CCCC2)CCCC1]

1,4 Bis(1-methylpyrrolidium 1-yl) butane

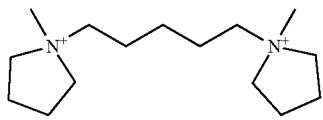 [SMILES: C[N+]1(CCCCC[N+]2(C)CCCC2)CCCC1]

1,5 Bis(1-methylpyrrolidium 1-yl) pentane

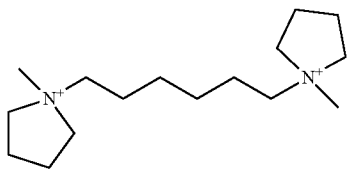 [SMILES: C[N+]1(CCCCCC[N+]2(C)CCCC2)CCCC1]

1,6 Bis(1-methylpyrrolidium 1-yl) hexatane

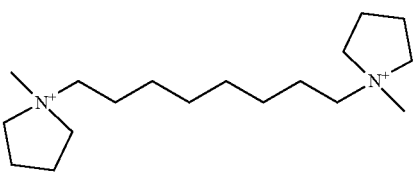 [SMILES: C[N+]1(CCCCCCCC[N+]2(C)CCCC2)CCCC1]

1,8 Bis(1-methylpyrrolidium 1-yl) octane

More advantageously, Y is selected from a group consisting of sulfonyl, carbonic acid, ether, ketone group and ester.

Yet more advantageously, $X_1YX_2$ is selected from a group consisting:

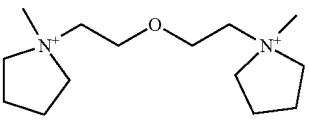 [SMILES: C[N+]1(CCOCC[N+]2(C)CCCC2)CCCC1]

Bis [2-(1-methylpyrrolidinium 1-yl) ethyl] ether

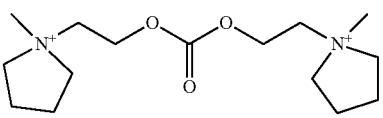 [SMILES: C[N+]1(CCOC(=O)OCC[N+]2(C)CCCC2)CCCC1]

Bis [2-(1-methylpyrrolidinium 1-yl) ethyl] carbonate

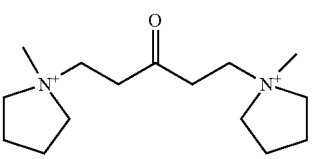 [SMILES: C[N+]1(CCC(=O)CC[N+]2(C)CCCC2)CCCC1]

1,5-Bis(1-methylpyrrolidinium 1-yl) pentan-3-one

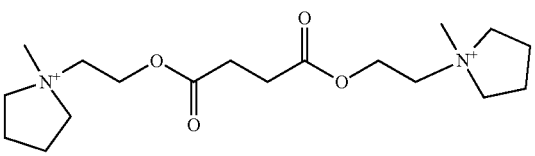 [SMILES: C[N+]1(CCOC(=O)CCC(=O)OCC[N+]2(C)CCCC2)CCCC1]

Bis[2-(1-methylpyrrolidinium 1-yl) ethyl] butanedioate

Preferably, the anionic group $Z_1$ and $Z_2$ os selected from a group consisting: $PF_6^-$ (hexafluorophosphate), $POF_2^-$ (difluorophosphate), $BF_4^-$ (tetrafluoroborate), $B(C_2O_4)_2^-$ (BOB$^-$, bis(oxalato) borate), $BF_2(C_2O_4)^-$ (ODFB$^-$, difluoro(oxalato)borate), $CF_3BF_3^-$ (trifluoromethyltrifluoroborate), $(FSO_2)_2N^-$ (FSI$^-$, bis(fluorosulfonyl)imide), $(CF_3SO_2)_2N^-$ (TFSI$^-$, bis(trifluoromethane)sulfonamide), $CH_3SO_4^-$ (MeSO$_4^-$, methyl sulfate).

In a second aspect of the invention there is provided an ionic liquid for adding to an electrolyte of a lithium-ion battery, the ionic liquid comprises a compound with a dual core structure having the general formula (I):

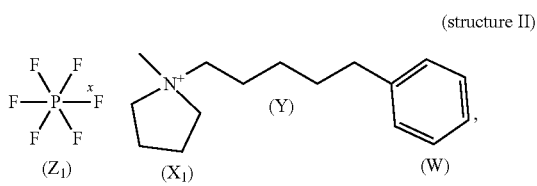

(structure II)

wherein each of cationic group $X_1$ and $X_2$ are heterocyclic aromatic and amine.

Preferably, the heterocyclic aromatic is selected from a group consisting piperidinium, pyrrolidinium, pyrazolium and pyridinium.

More preferably, the amine is selected from a group consisting quaternary ammonium, azepane and phosphonium.

Yet more preferably, Y is any one of C3~C10 alkyl group.

It is preferable that Y is selected from a group consisting of sulfonyl, carbonic acid, ether, ketone group and ester.

Advantageously, $X_1YW$ is selected from a group consisting:

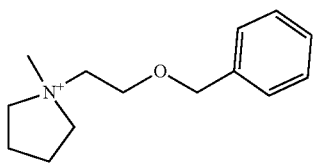 [SMILES: C[N+]1(CCOCc2ccccc2)CCCC1]

Benzyl-2-(1-methylpyrrolidinium 1-yl) ethyl ether

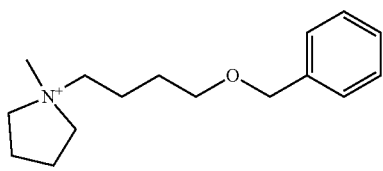 [SMILES: C[N+]1(CCCCOCc2ccccc2)CCCC1]

Benzyl-4-(1-methylpyrrolidinium 1-yl) butyl ether

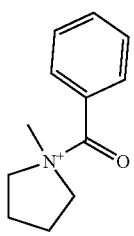

1-(1-Benzoyl)-1-methyl pyrrolidinium

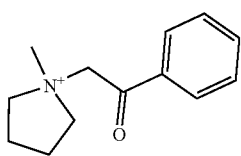

1-(2-Phenacyl)-1-methyl pyrrolidinium

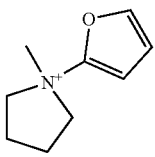

1-(Furan 2-yl)-1-methyl pyrrolidinium

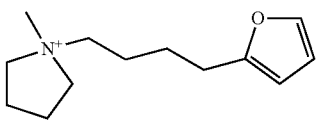

1-(butyl furan 2-yl)-1-methyl pyrrolidinium

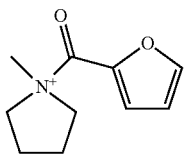

1-(2-Furoyl)-1-methyl pyrrolidinium

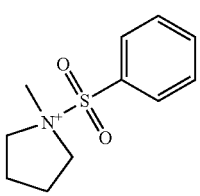

1-Benzensulfonyl-1-methyl pyrrolidinium

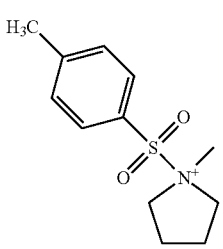 [SMILES: Cc1ccc(S(=O)(=O)[N+]2(C)CCCC2)cc1]

1-p-Toluenesulfonyl-1-methyl pyrrolidinium

More advantageously, the anionic group $Z_1$ and $Z_2$ of the ionic liquid with structural formula I and formula II can include $PF_6^-$ (hexafluorophosphate), $POF_2^-$ (difluorophosphate), $BF_4^-$ (tetrafluoroborate), $B(C_2O_4)_2^-$ (BOB$^-$, bis(oxalato) borate), $BF_2(C_2O_4)^-$ (ODFB$^-$, difluoro(oxalato)borate), $CF_3BF_3^-$ (trifluoromethyltrifluoroborate), $(FSO_2)_2N^-$ (FSI$^-$, bis(fluorosulfonyl)imide), $(CF_3SO_2)_2N^-$ (TFSI$^-$, bis(trifluoromethane) sulfonamide), $CH_3SO_4^-$ (MeSO$_4^-$, methyl sulfate).

In a third aspect of the invention there is provided a lithium ion battery comprising a positive electrode, a negative electrode, a separator, an electrolyte and one or more ionic liquid disclosed herein, wherein an overall amount of ionic liquid added to the electrolyte is 0.1-15 wt. %.

Preferably, the lithium ion battery further comprising a stabilizer, wherein the stabilizer is a cyclophosphazene compound.

More preferably, the stabilizer is selected from a group consisting:

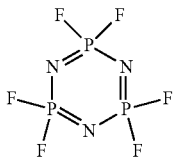

Hexafluoro cyclotriphosphazene

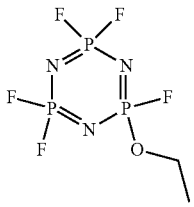

Ethoxy (pentafluoro) cyclotriphosphazene

Yet more preferably, amount of stabilizer added to the electrolyte is 0.1-2.9 wt. %.

It is preferable that a SEI film forming agent is added to the electrolyte.

Advantageously, the SEI film forming agent is selected from a group consisting of fluoroethylene carbonate (FEC), vinylene carbonate (VC), vinyl ethylene carbonate (VEC), ethylene sulfite (ES), propylene sulfite (PS), and ethylene sulfate (DTD), and the combination thereof.

More advantageously, the amount of the SEI film forming agent added to the electrolyte is 0.1-5 wt. %.

More advantageously, the electrolyte is an non-aqueous electrolyte.

Yet more advantageously, the non-aqueous electrolyte comprises a lithium salt selected from a group consisting of $LiPF_6$, $LiClO_4$, $LiBF_4$, $LiSO_3CF_3$, $LiN(SO_2F)_2$, $LiN(SO_2CF_3)_2$, $LiN(SO_2CF_2CF_3)_2$, $LiAsF_6$, $LiAlCl_4$, $LiNO_3$, $LiPOF_2$, $LiB(C_2O_4)_2$, $LiBF_2(C_2O_4)$, $LiCF_3BF_3$, or a combination thereof.

Preferably, concentration of the lithium salt in the electrolyte is 0.5~1.5 mol/L.

More preferably, the nonauqeous electrolyte comprises an organic solvent selected from a group consisting of carbonate, carboxylate, ether, ketone, and combinations thereof More preferably, the carbonate is selected from a group consisting ethylene carbonate (EC), propylene carbonate (PC), diethyl carbonate (DEC), methyl ethyl carbonate (EMC), dimethyl carbonate (DMC), dipropyl carbonate, dibutyl carbonate, and a combination thereof.

Preferably, the carboxylate is carboxylic acid ester.

More preferably, the carboxylic acid ester comprises methyl acetate, ethyl acetate, methyl butyrate, ethyl butyrate, methyl propionate, ethyl propionate and propyl acetate, and a combination thereof.

It is preferable that the positive electrode comprises an active material being lithium metal complex oxide compound.

It is preferable that the metal element of the lithium metal complex oxide is selected from a group consisting of transition metal and non-transition metal.

Preferably, the transition metal is selected from a group consisting vanadium, titanium, chromium, copper, iron, nickel and cobalt.

More preferably, the non-transition metal is selected from a group consisting aluminum and manganese.

Yet more preferably, the negative electrode comprises an active material selected from a group consisting soft carbon, hard carbon, artificial graphite, natural graphite, meso carbon micro bead (MCMB), silicon, silicon oxide compounds, silicon carbon composites, lithium titanate oxide, and the metals that forms alloy with lithium.

It is preferable that the negative electrode comprises an active material that is carbon-based, silicon-based or tin-based.

Advantageously, the separator comprises a membrane.

More advantageously, the membrane comprises a material selected form a group consisting polyethylene (PE), polypropylene (PP), polyvinylidene fluoride (PVDF), ceramic material, glass fiber and a combination thereof.

BRIEF DESCRIPTION OF DRAWINGS

The invention will now be more particularly described, by way of example only, with reference to the accompanying drawings, in which:

FIG. 1 is a table that shows the synthesis parameters of bis(1-methylpyrrolidium) alkyl halide;

FIG. 2 is a table that shows the synthesis parameters of two-core cationic chain halide;

FIG. 3A is a table that shows the synthesis parameters of two-core cationic chain ionic liquid;

FIG. 3B is a continuation of the table in FIG. 3A;

FIG. 4 is a table that shows the synthesis parameters of aromatic bonded to 1-methylpyrrolidinium halide;

FIG. 5 is a table that shows the synthesis parameters of aromatic bonded to cation halide;

FIG. 6A is a table that shows the synthesis parameters of aromatic bonded to cation ionic liquid;

FIG. 6B is a continuation of the table in FIG. 6A;

FIG. 15A is a table showing the maximum oxidation potential of electrolyte with the two-core structure ionic liquid at the LSV test;

FIG. 15B is a continuation of the table in FIG. 15A;

FIG. 15C is a continuation of the table in FIG. 15A and FIG. 15B;

FIG. 16A is a table showing the maximum oxidation potential of electrolyte with aromatic bonded to cation ionic liquid at the LSV test;

FIG. 16B is a continuation of the table in FIG. 16A;

FIG. 21A is a table showing the composition of different electrolyte formulas;

FIG. 21B is a continuation of the table in FIG. 21A;

FIG. 23A is a table showing results of the self-extinguishing time of various electrolyte formulations and its internal impedance and long-cycle performance of lithium-ion battery; and FIG. 23B is a continuation of the table in FIG. 23A.

DETAILED DESCRIPTION OF PREFERRED EMBODIMENT

Figure 7A:
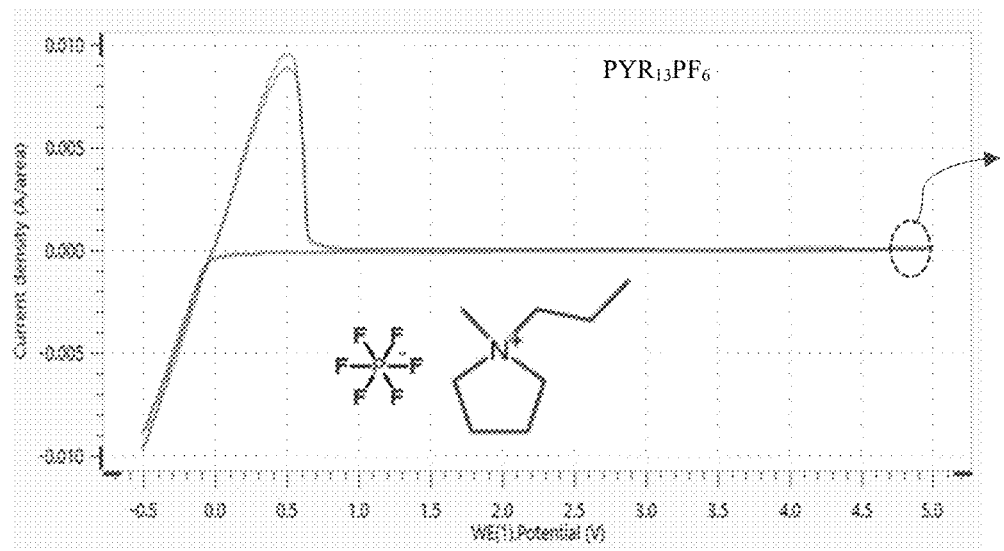
FIG. 7A is a graph showing results of a liner sweep voltammetry LSV of $PYR_{13}PF_6$.

The first aspect of the invention relates to an ionic liquid with dual core cationic chain and aromatic functional group bonded to cation (dual core structure). It has a high melting point and a wide potential window, is not easy to intercalate into graphite layer of anode materials, and can form a solid electrolyte interface (SEI) with uniform, compact, and high lithium diffusion reversibility on the surface of the anode.

The ionic liquid is added to the non-aqueous electrolyte, to enhance the long-term cyclic stability of the high compacted density electrode and improve the thermal stability of the resulting lithium ion battery.

The dual-core structure increases the structural volume of the cation much bigger such that it becomes too large for intercalation in graphite. A uniform and dense SEI layer is formed on the surface of graphite for reversible intercalation and release of lithium ions. This reduces the interface impedance and enhance the long-term cyclic stability for the lithium-ion battery. Furthermore, the SEI layer with high flame retardancy produced after adding the ionic liquid to the electrolyte can absorb internal heat and inhibit thermal runaway.

As discussed above, the dual core cation is characterized by an aromatic compound, amine salt and heterocyclic compound.

The second aspect of the invention involves the use of the ionic liquid in the first aspect of the invention with a non-aqueous electrolyte.

The third aspect of the invention is related to a lithium-ion battery with the non-aqueous electrolyte in the second aspect and the ionic liquid in the second aspect.

In more detail, the dual-core structure of ionic liquid has the two functional groups chain. It is made up of a dual-core cationic chain and an aromatic functional group bonded to cations in the dual-core cationic chain. The dual-core structure has a general formula of $Z_1X_1YX_2Z_2$ and $Z_1X_1YW$, with their chemical structural formulas shown below as structure I and structure II, respectively.

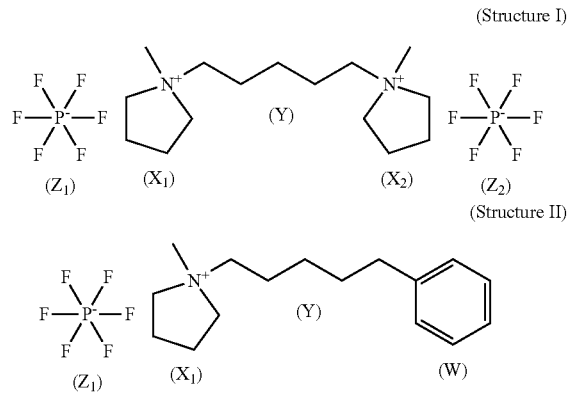

(Structure I)

(Structure II)

The cationic group $X_1$ and $X_2$ in structural formula I and the cationic group $X_1$ in structural formula II are selected from a group consisting heterocyclic aromatics and amine salt. The heterocyclic aromatics includes piperidinium, pyrrolidinium, pyrazolium and pyridinium, while the amine salt includes quaternary ammonium, azepane and phosphonium.

More specifically, the cationic group $X_1$ and $X_2$ in structural formula I and the cationic group $X_1$ in structural formula II are selected from:

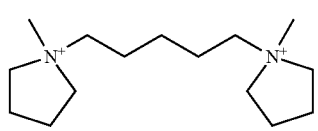 [SMILES: C[N+]1(CCCCC[N+]2(C)CCCC2)CCCC1]

1,5 Bis(1-methylpyrrolidium 1-yl) pentane,

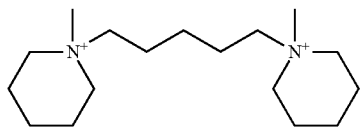 [SMILES: C[N+]1(CCCCC[N+]2(C)CCCCC2)CCCCC1]

1,5 Bis(1-methylpiperidinium 1-yl) pentane,

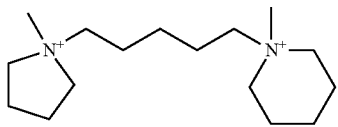 [SMILES: C[N+]1(CCCCC[N+]2(C)CCCC2)CCCCC1]

1,5 (1-methylpyrrolidium 1-yl) (1-methylpiperidinium 1-yl) pentane,

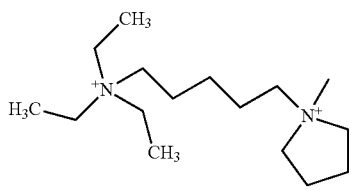 [SMILES: CC[N+](CC)(CC)CCCCC[N+]1(C)CCCC1]

1,5-[(1-methylpyrrolidium 1-yl) (triethylamine N-yl)] pentane, and/or

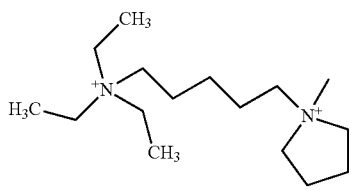 [SMILES: CC[N+](CC)(CC)CCCCC[N+]1(C)CCCC1]

1,5-[(1-methylpiperidinium 1-yl) (triethylamine N-yl)] pentane.

The functional group Y of the ionic liquid with structural formula I and formula II is alkyl group, R indicates the number of carbon atom in the alkyl group, wherein the R=3-10 in particular it is selected from:

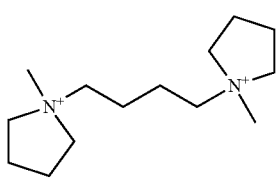 [SMILES: C[N+]1(CCCC[N+]2(C)CCCC2)CCCC1]

1,4 Bis(1-methylpyrrolidium 1-yl) butane,

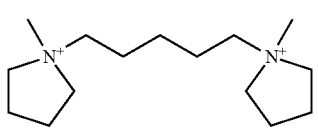 [SMILES: C[N+]1(CCCCC[N+]2(C)CCCC2)CCCC1]

1,5 Bis(1-methylpyrrolidium 1-yl) pentane,

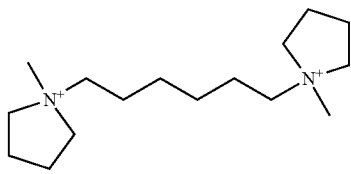 [SMILES: C[N+]1(CCCCCC[N+]2(C)CCCC2)CCCC1]

1,6 Bis (1-methylpyrrolidium 1-yl) hexatane, and/or

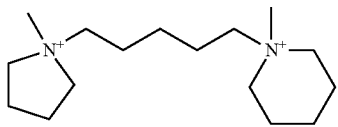 [SMILES: C[N+]1(CCCCC[N+]2(C)CCCC2)CCCCC1]

1,8 Bis(1-methylpyrrolidium 1-yl) octane

The functional group Y of the ionic liquid with structural formula I and formula II is selected from sulfonyl, carbonic acid, ether, ketone group or ester. In particular, the function group Y is selected from:

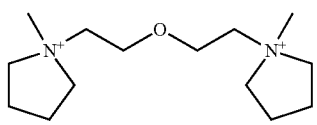 [SMILES: C[N+]1(CCOCC[N+]2(C)CCCC2)CCCC1]

Bis [2-(1-methylpyrrolidinium 1-yl) ethyl] ether,

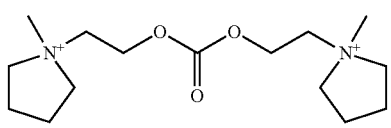 [SMILES: C[N+]1(CCOC(=O)OCC[N+]2(C)CCCC2)CCCC1]

Bis [2-(1-methylpyrrolidinium 1-yl) ethyl] carbonate,

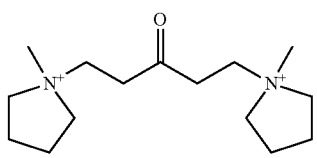 [SMILES: C[N+]1(CCC(=O)CC[N+]2(C)CCCC2)CCCC1]

1,5-Bis(1-methylpyrrolidinium 1-yl) pentan-3-one, and/or

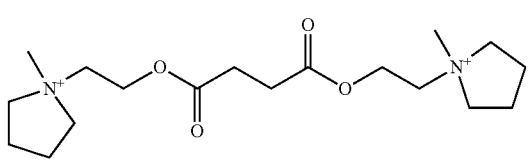 [SMILES: C[N+]1(CCOC(=O)CCC(=O)OCC[N+]2(C)CCCC2)CCCC1]

Bis[2-(1-methylpyrrolidinium 1-yl) ethyl] butanedioate

The cationic group $X_1$, the functional group Y and the aromatic group W of the ionic liquid with structural formula II is selected from:

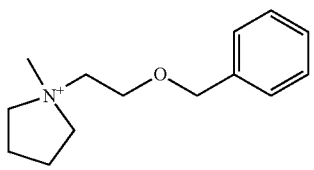 [SMILES: C[N+]1(CCOCc2ccccc2)CCCC1]

Benzyl-2-(1-methylpyrrolidinium 1-yl) ethyl ether,

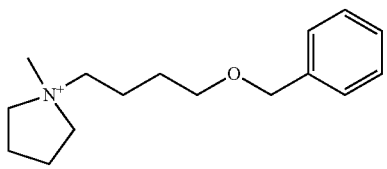 [SMILES: C[N+]1(CCCCOCc2ccccc2)CCCC1]

Benzyl-4-(1-methylpyrrolidinium 1-yl) butyl ether,

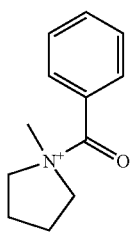

1-(1-Benzoyl)-1-methyl pyrrolidinium,

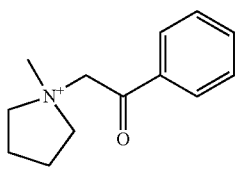

1-(2-Phenacyl)-1-methyl pyrrolidinium,

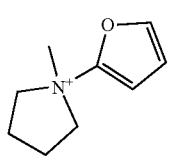

1-(Furan 2-yl)-1-methyl pyrrolidinium,

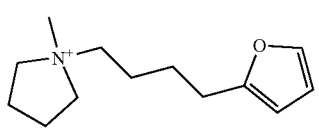

1-(butyl furan 2-yl)-1-methyl pyrrolidinium,

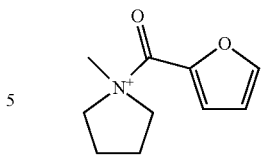

1-(2-Furoyl)-1-methyl pyrrolidinium,

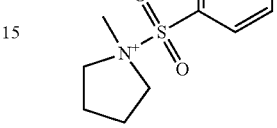

1-Benzensulfonyl-1-methyl pyrrolidinium, and/or

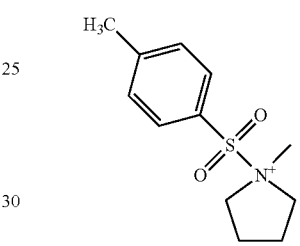

1-p-Toluenesulfonyl-1-methyl pyrrolidinium.

The anionic group $Z_1$ and $Z_2$ of the ionic liquid with structural formula I and formula II may include $PF_6^-$ (hexafluorophosphate), $POF_2^-$ (difluorophosphate), $BF_4^-$ (tetrafluoroborate), $B(C_2O_4)_2^-$ (BOB$^-$, bis(oxalato) borate), $BF_2(C_2O_4)^-$ (ODFB$^-$, difluoro(oxalato)borate), $CF_3BF_3^-$ (trifluoromethyltrifluoroborate), $(FSO_2)_2N^-$ (FSI—, bis(fluorosulfonyl)imide), $(CF_3SO_2)_2N^-$ (TFSI$^-$, bis(trifluoromethane)sulfonamide), and/or $CH_3SO_4^-$ (MeSO$_4^-$, methyl sulfate).

The weight percentage of the ionic liquid in the electrolyte is 0.1-15 wt. %. When the added amount of ionic liquid is too low, the improvement effect of the electrolyte on the surface of anode is not obvious, but that is too high, the thickness of SEI layer formed will be much larger, consequently increases the interface impedance between the cathode and anode, resulting in the decline of battery performance.

The non-aqueous electrolyte, including lithium salt, organic solvent, film-forming agent, stabilizer and ionic liquid.

The stabilizer in the non-aqueous electrolyte is a cyclophosphazene compound, preferably selected from the followings:

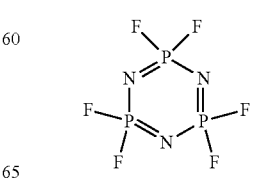

Hexafluoro cyclotriphosphazene, and/or

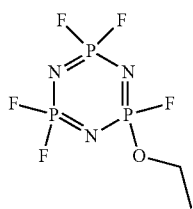

Ethoxy (pentafluoro) cyclotriphosphazene.

The cyclophosphazene compound contains P and F which are both highly efficient flame retardants. The presence of P and F allow for reduction in the amount of ionic liquid to be added into the electrolyte with noticeable thermal stability advantage. F assists in generating more LiF on the SEI film formed on the surface of the electrode. The LiF on the SEI film acts as a good oxidation resister to increase the compatibility between the electrolyte and any active materials in the electrode by reducing the reaction between them and the production of unwanted by-product. This in turns stabilizes the electrochemical reaction of electrodes and improves the long term cyclic performance of lithium-ion batteries with high-voltage. The proposed amount of stabilizer in the electrolyte is 0.1-2.9 wt. %.

The SEI film forming agent in the non-aqueous electrolyte is selected from one or more of fluoroethylene carbonate (FEC), vinylene carbonate (VC), vinyl ethylene carbonate (VEC), ethylene sulfite (ES), propylene sulfite (PS), and ethylene sulfate (DTD).

The film-forming agent has a higher reduction potential and can be preferentially reduced as SEI film on the surface of the graphite electrode. The inorganic lithium compound containing sulfur and fluorine is more stable, and it is beneficial to the insertion and release of lithium ions, lower the reduction and decomposition rate of the electrolyte as well as the occurrence of undesirable side reaction on the surface of negative electrode. The preferred amount of SEI film-forming agent in the electrolyte is 0.1-5 wt. %. It is a fine balance. Too low an amount of the SEI film-forming agent will result insignificant improvement on the surface of the electrode, while too large an amount of the SEI film-forming agent results in undesirable thickening of the SEI film as this will affect the capacity retention of the battery which brings about a decline in the cyclic performance of the overall battery.

The lithium salt in the non-aqueous electrolyte includes any one of $LiPF_6$, $LiClO_4$, $LiBF_4$, $LiSO_3CF_3$, $LiN(SO_2F)_2$, $LiN(SO_2CF_3)_2$, $LiN(SO_2CF_2CF_3)_2$, $LiAsF_6$, $LiAlCl_4$, $LiNO_3$, $LiPOF_2$, $LiB(C_2O_4)_2$, $LiBF_2(C_2O_4)$, $LiCF_3BF_3$, or a combination thereof. The preferred concentration of lithium salt in the electrolyte ranges from 0.5 to 1.5 mol/L.

The organic solvent of the non-aqueous electrolyte is selected from carbonate, carbonate ester (organic carbonate or organocarbonate), carboxylate, carboxylate ester, ethers, ketones or combinations thereof. Among them, carbonates may be any one of ethylene carbonate (EC), propylene carbonate (PC), diethyl carbonate (DEC), methyl ethyl carbonate (EMC), dimethyl carbonate (DMC), and dipropyl carbonate, Dibutyl carbonate, or a combination thereof. The carboxylic acid esters may be any one of methyl acetate, ethyl acetate, methyl butyrate, ethyl butyrate, methyl propionate, ethyl propionate, propyl acetate, and a combination thereof.

Other organic solvents is suitably selected from one of a cyclic ether such as tetrahydrofuran, 2-methyltetrahydrofuran, 1,4-dioxane, a chain ether such as 1,2-dimethoxyethane, 1,2-diethoxy ethane, 1,2-dibutoxyethane, an amide such as dimethylformamide, and a sulfide such as sulfolane, a lactone such as γ-butyrolactone, γ-valerolactone, or the organic solvents may be a combination of two of the above.

In an embodiment of the invention, there is provided a lithium-ion battery which has a positive electrode (cathode), a negative electrode (anode), a separator interposed between the positive and negative electrodes, and an added non-aqueous electrolyte. The positive and negative electrodes contain active materials that permit intercalation and exfoliation of lithium ions. Active material of cathode may be any one or a combination of lithium oxide compounds with metal elements such as vanadium, titanium, chromium, copper, aluminum, iron, nickel, cobalt, manganese, addition of other transition metals or non-transition metal to the aforementioned lithium transition metal oxides compounds, as well as mixture thereof. The specific crystal structure may be a layered lithium containing oxide, a spinel type lithium-containing oxides, or an olivine-type of lithium-containing phosphate compounds, etc. The cathode may contain one of the aforementioned active materials or a combination of two of more of those active materials. Active material of anode may be any one of or a combination of soft carbon, hard carbon, artificial graphite, natural graphite, meso carbon micro bead (MCMB), silicon, silicon oxide compound, silicon carbon composite, lithium titanate oxide, and metals that can form alloys with lithium, etc. Specifically, a carbon-based, silicon-based, tin-based negative electrode can be used. The anode may contain one or more of the aforementioned active materials.

In the above-mentioned lithium-ion battery, the positive and negative electrodes further include a binder and a conductive agent. A slurry of cathode material which contains the cathode active material, a binder and a conductive agent is coated on a current collector of positive electrode. The positive electrode is formed after the slurry dries. Similarly, the slurry of anode material which may include an anode active material, a binder and a conductive agent is coated on the current collector of a negative electrode. The negative electrode is obtained after the slurry dries.

The separator may be formed from any material that is commercially available for making suitable separators in commercial batteries such as but not limited to polyethylene (PE), polypropylene (PP), polyvinylidene fluoride (PVDF), ceramics materials, glass fibers or composite films of a combination of the above listed.

The electrolyte is the non-aqueous electrolyte as described.

The following embodiments are provided as examples only for explaining the invention.

Embodiment 1

The synthesis of ionic liquid with two-core cationic chain (structural formula I: $Z_1X_1YX_2Z_2$)

Step 1. Synthesis of Two-Core Cationic Halide
1. Taking the synthesis of 1,4-bis(1-methylpyrrolidium 1-yl) butane dichloride ($DiPYR_{14}Cl_2$) as an example: N-methyl pyrrolidine (NMPD) is purified by distillation at 85° C., and then mixed them at the mole ratio of NMPD:1,4-dichlorobutane at 2:1.1, followed by the addition of acetone which is at a volume same as that of the dichloroalkyl. It is then mixed and stirred at 70° C. for 16 hours and distilled to remove the acetone. The resulting liquid is $DiPYR_{14}Cl_2$.

2. Change the alkyl chain Y to other functional groups, such as sulfonyl, carbonate, ether, ketone, ester, etc. Taking the synthesis of bis [2-(1-methylpyrrolidinium 1-yl) ethyl] ether dichloride (DiPYR$_{IEE}$Cl$_2$) as an example (No. 8 of FIG. 1/Table 1): Firstly, N-methyl pyrrolidine (NMPD) is purified by distillation at 85° C., and then NMPD and bis(2-chloroethyl) ether are mixed at a mole ratio of 2:1.1 followed by the addition of acetone which is at a volume same as the bis(2-chloroethyl) ether. It is then mixed and stirred at 70° C. for 16 hours and distilled to remove the acetone. The resulting liquid is DiPYR$_{IEE}$Cl$_2$.

The synthesis parameters of other series of bis(1-methylpyrrolidium) alkyl halide ionic liquids are shown in FIG. 1/Table 1.

With reference to FIG. 1/Table 1, the synthesis of DiPYR$_{14}$Cl$_2$:
1) NMPD is purified by distillation at 85° C.,
2) NMPD and 1,4-Dichlorobutane are mixed at a mole ratio of 2:1.1.
3) Addition of acetone which is at a volume same as the 1,4-Dichlorobutane.
4) Mix and stir at 70° C. for 16 hours.
5) Distilled to remove the acetone. The resulting liquid is DiPYR$_{14}$Cl$_2$.

With reference to FIG. 1/Table 1, the synthesis of DiPYR$_{15}$Cl$_2$:
1) NMPD is purified by distillation at 85° C.,
2) NMPD and 1,5-Dichloropentane are mixed at a mole ratio of 2:1.1.
3) Addition of acetone which is at a volume same as the 1,5-Dichloropentane.
4) Mix and stir at 70° C. for 16 hours.
5) Distilled to remove the acetone. The resulting liquid is DiPYR$_{15}$Cl$_2$.

With reference to FIG. 1/Table 1, the synthesis of DiPYR$_{16}$Cl$_2$:
1) NMPD is purified by distillation at 85° C.,
2) NMPD and 1,6-Dichlorohexane are mixed at a mole ratio of 2:1.1.
3) Addition of acetone which is at a volume same as the 1,6-Dichlorohexane.
4) Mix and stir at 70° C. for 16 hours.
5) Distilled to remove the acetone. The resulting liquid is DiPYR$_{16}$Cl$_2$.

With reference to FIG. 1/Table 1, the synthesis of DiPYR$_{17}$Cl$_2$:
1) NMPD is purified by distillation at 85° C.,
2) NMPD and 1,7-Dichloroheptane are mixed at a mole ratio of 2:1.1.
3) Addition of acetone which is at a volume same as the 1,7-Dichloroheptane.
4) Mix and stir at 70° C. for 16 hours.
5) Distilled to remove the acetone. The resulting liquid is DiPYR$_{17}$Cl$_2$.

With reference to FIG. 1/Table 1, the synthesis of DiPYR$_{18}$Cl$_2$:
1) NMPD is purified by distillation at 85° C.,
2) NMPD and 1,8-Dichlorooctane are mixed at a mole ratio of 2:1.1.
3) Addition of acetone which is at a volume same as the 1,8-Dichlorooctane.
4) Mix and stir at 70° C. for 16 hours.
5) Distilled to remove the acetone. The resulting liquid is DiPYR$_{18}$Cl$_2$.

With reference to FIG. 1/Table 1, the synthesis of DiPYR$_{19}$Cl$_2$:
1) NMPD is purified by distillation at 85° C.,
2) NMPD and 1,9-Dichlorononane are mixed at a mole ratio of 2:1.1.
3) Addition of acetone which is at a volume same as the 1,9-Dichlorononane.
4) Mix and stir at 70° C. for 16 hours.
5) Distilled to remove the acetone. The resulting liquid is DiPYR$_{19}$Cl$_2$.

With reference to FIG. 1/Table 1, the synthesis of DiPYR$_{110}$Cl$_2$:
1) NMPD is purified by distillation at 85° C.,
2) NMPD and 1,10-Dichlorodecane are mixed at a mole ratio of 2:1.1.
3) Addition of acetone which is at a volume same as the 1,10-Dichlorodecane.
4) Mix and stir at 70° C. for 16 hours.
5) Distilled to remove the acetone. The resulting liquid is DiPYR$_{110}$Cl$_2$.

With reference to FIG. 1/Table 1, the synthesis of DiPYR$_{IEE}$Cl$_2$:
1) NMPD is purified by distillation at 85° C.,
2) NMPD and Bis(2-chloroethyl)ether are mixed at a mole ratio of 2:1.1.
3) Addition of acetone which is at a volume same as the Bis(2-chloroethyl)ether.
4) Mix and stir at 70° C. for 16 hours.
5) Distilled to remove the acetone. The resulting liquid is DiPYR$_{IEE}$Cl$_2$.

With reference to FIG. 1/Table 1, the synthesis of DiPYR$_{IEC}$Cl$_2$:
1) NMPD is purified by distillation at 85° C.,
2) NMPD and Bis(2-chloroethyl) carbonate are mixed at a mole ratio of 2:1.1.
3) Addition of acetone which is at a volume same as the Bis(2-chloroethyl) carbonate.
4) Mix and stir at 70° C. for 16 hours.
5) Distilled to remove the acetone. The resulting liquid is DiPYR$_{IEC}$Cl$_2$.

With reference to FIG. 1/Table 1, the synthesis of DiPYR$_{IPO}$Cl$_2$:
1) NMPD is purified by distillation at 85° C.,
2) NMPD and 1,5-dichloro pentan-3-one are mixed at a mole ratio of 2:1.1.
3) Addition of acetone which is at a volume same as the 1,5-dichloro pentan-3-one.
4) Mix and stir at 70° C. for 16 hours.
5) Distilled to remove the acetone. The resulting liquid is DiPYR$_{IPO}$Cl$_2$.

With reference to FIG. 1/Table 1, the synthesis of DiPYR$_{IEB}$Cl$_2$:
1) NMPD is purified by distillation at 85° C.,
2) NMPD and Bis(2-chloroethyl) butanedioate are mixed at a mole ratio of 2:1.1.
3) Addition of acetone which is at a volume same as the Bis(2-chloroethyl) butanedioate.
4) Mix and stir at 70° C. for 16 hours.
5) Distilled to remove the acetone. The resulting liquid is DiPYR$_{IEB}$Cl$_2$.

3. Replacing the cations $X_1$ and $X_2$ with other heterocyclic aromatic or amine, which may include imidazolium, quaternary ammonium, piperidinium, pyrrolidinium, morpholinium, trimethylamine, etc. Taking the synthesis of 1,5-bis(1-methylpiperidinium 1-yl) pentane dichloride (DiPIP$_{15}$Cl$_2$) as an example: N-methyl piperidine (MPIP) is purified by vacuum distillation, and then MPIP and 1,5-dichloropentane are mixed at the mole ratio of 2:1.1 followed by the addition of acetone which has a volume same as that of the dichloroalkyl. It is then mixed and stirred at 70° C. for 16 hours. After distilling off the acetone, the remaining liquid is $DiPIP_{15}Cl_2$.

Taking the synthesis of 1,5-(1-methylpyrrolidium 1-yl)(1-methylpiperidinium 1-yl) pentane dichloride ($PYRPIP_{15}Cl_2$) as an example (no. 5 of FIG. 2/Table 2). N-methyl pyrrolidine (NMPD) and N-methyl piperidine (MPIP) are purified by vacuum distillation. NMPD, MPIP, and 1,5-Dichloropentane are mixed at a mole ratio of 1:1:1.1 followed by the addition of acetone which is in the same volume as the 1,5-Dichloropentane. It is then mixed and stirred at 70° C. for 16 hours. After the acetone is distilled off, the remaining liquid is $PYRPIP_{15}Cl_2$. The synthesis parameters of other series of two-core cationic halide ionic liquid are shown in FIG. 2/Table 2

With reference to FIG. 2/Table 2, the synthesis of $DiPYR_{15}Cl_2$:
1) N-methyl pyrrolidine (NMPD) is purified by distillation at 85° C.
2) NMPD and 1,5-Dichloropentane are mixed at a mole ratio of 2:1.1
3) Adding acetone which is in the same volume as the 1,5-Dichloropentane
4) Mix and stir at 70° C. for 16 hours.
5) Acetone is distilled off and the remaining liquid is $DiPYR_{15}Cl_2$.

With reference to FIG. 2/Table 2, the synthesis of $DiPIP_{15}Cl_2$:
1) N-methyl piperidine (MPIP) is purified by vacuum distillation.
2) MPIP and 1,5-Dichloropentane are mixed at a mole ratio of 2:1.1
3) Adding acetone which is in the same volume as the 1,5-Dichloropentane
4) Mix and stir at 70° C. for 16 hours.
5) Acetone is distilled off and the remaining liquid is $DiPIP_{15}Cl_2$.

With reference to FIG. 2/Table 2, the synthesis of $DiTEA_{15}Cl_2$:
1) Triethylamine (TEA) is purified by vacuum distillation.
2) TEA and 1,5-Dichloropentane are mixed at a mole ratio of 2:1.1
3) Adding acetone which is in the same volume as the 1,5-Dichloropentane
4) Mix and stir at 70° C. for 16 hours.
5) Acetone is distilled off and the remaining liquid is $DiTEA_{15}Cl_2$.

With reference to FIG. 2/Table 2, the synthesis of $DiMIM_{15}Cl_2$:
1) 1-methylimidazole (MIM) is purified by vacuum distillation.
2) MIM and 1,5-Dichloropentane are mixed at a mole ratio of 2:1.1
3) Adding acetone which is in the same volume as the 1,5-Dichloropentane
4) Mix and stir at 25° C. for 12 hours.
5) Acetone is distilled off and the remaining liquid is $DiMIM_{15}Cl_2$.

With reference to FIG. 2/Table 2, the synthesis of $PYRPIP_{15}Cl_2$:
1) NMPD and MPIP are purified by vacuum distillation.
2) NMPD and MPIP and 1,5-Dichloropentane are mixed at a mole ratio of 1:1:1.1
3) Adding acetone which is in the same volume as the 1,5-Dichloropentane
4) Mix and stir at 70° C. for 16 hours.
5) Acetone is distilled off and the remaining liquid is $PYRPIP_{15}Cl_2$.

With reference to FIG. 2/Table 2, the synthesis of $PYRTEA_{15}Cl_2$:
1) NMPD and TEA are purified by vacuum distillation.
2) NMPD and TEA and 1,5-Dichloropentane are mixed at a mole ratio of 1:1:1.1
3) Adding acetone which is in the same volume as the 1,5-Dichloropentane
4) Mix and stir at 70° C. for 16 hours.
5) Acetone is distilled off and the remaining liquid is $PYRTEA_{15}Cl_2$.

With reference to FIG. 2/Table 2, the synthesis of $PYRMPE_{15}Cl_2$:
1) NMPD and Morpholine (MPE) are purified by vacuum distillation.
2) NMPD and MPE and 1,5-Dichloropentane are mixed at a mole ratio of 1:1:1.1
3) Adding acetone which is in the same volume as the 1,5-Dichloropentane
4) Mix and stir at 45° C. for 12 hours.
5) Acetone is distilled off and the remaining liquid is $PYRMPE_{15}Cl_2$.

With reference to FIG. 2/Table 2, the synthesis of $PYRMIM_{15}Cl_2$:
1) NMPD and MIM are purified by vacuum distillation.
2) NMPD and MIM and 1,5-Dichloropentane are mixed at a mole ratio of 1:1:1.1
3) Adding acetone which is in the same volume as the 1,5-Dichloropentane
4) Mix and stir at 25° C. for 12 hours.
5) Acetone is distilled off and the remaining liquid is $PYRMPE_{15}Cl_2$.

With reference to FIG. 2/Table 2, the synthesis of $PYRPYO_{15}Cl_2$:
1) NMPD and Pyrrole (PYO) are purified by vacuum distillation.
2) NMPD and PYO and 1,5-Dichloropentane are mixed at a mole ratio of 1:1:1.1
3) Adding acetone which is in the same volume as the 1,5-Dichloropentane
4) Mix and stir at 45° C. for 12 hours.
5) Acetone is distilled off and the remaining liquid is $PYRPYO_{15}Cl_2$.

With reference to FIG. 2/Table 2, the synthesis of $PIPTEA_{15}Cl_2$:
1) MPIP and TEA are purified by vacuum distillation.
2) MPIP and TEA and 1,5-Dichloropentane are mixed at a mole ratio of 1:1:1.1
3) Adding acetone which is in the same volume as the 1,5-Dichloropentane
4) Mix and stir at 70° C. for 16 hours.
5) Acetone is distilled off and the remaining liquid is $PIPTEA_{15}Cl_2$.

With reference to FIG. 2/Table 2, the synthesis of $PIPMPE_{15}Cl_2$:
1) MPIP and MPE are purified by vacuum distillation.
2) MPIP and MPE and 1,5-Dichloropentane are mixed at a mole ratio of 1:1:1.1
3) Adding acetone which is in the same volume as the 1,5-Dichloropentane
4) Mix and stir at 45° C. for 12 hours.
5) Acetone is distilled off and the remaining liquid is $PIPMPE_{15}Cl_2$.

With reference to FIG. 2/Table 2, the synthesis of $PIPMIM_{15}Cl_2$:
1) MPIP and MIM are purified by vacuum distillation.
2) MPIP and MIM and 1,5-Dichloropentane are mixed at a mole ratio of 1:1:1.1
3) Adding acetone which is in the same volume as the 1,5-Dichloropentane
4) Mix and stir at 25° C. for 12 hours.
5) Acetone is distilled off and the remaining liquid is $PIPMIM_{15}Cl_2$.

With reference to FIG. 2/Table 2, the synthesis of $PIPPYO_{15}Cl_2$:
1) MPIP and PYO are purified by vacuum distillation.
2) MPIP and PYO and 1,5-Dichloropentane are mixed at a mole ratio of 1:1:1.1
3) Adding acetone which is in the same volume as the 1,5-Dichloropentane
4) Mix and stir at 45° C. for 12 hours.
5) Acetone is distilled off and the remaining liquid is $PIPPYO_{15}Cl_2$.

With reference to FIG. 2/Table 2, the synthesis of $TEAMPE_{15}Cl_2$:
1) TEA and MPE are purified by vacuum distillation.
2) TEA and MPE and 1,5-Dichloropentane are mixed at a mole ratio of 1:1:1.1
3) Adding acetone which is in the same volume as the 1,5-Dichloropentane
4) Mix and stir at 45° C. for 12 hours.
5) Acetone is distilled off and the remaining liquid is $TEAMPE_{15}Cl_2$.

With reference to FIG. 2/Table 2, the synthesis of $TEAMIM_{15}Cl_2$:
1) TEA and MIM are purified by vacuum distillation.
2) TEA and MIM and 1,5-Dichloropentane are mixed at a mole ratio of 1:1:1.1
3) Adding acetone which is in the same volume as the 1,5-Dichloropentane
4) Mix and stir at 25° C. for 12 hours.
5) Acetone is distilled off and the remaining liquid is $TEAMIM_{15}Cl_2$.

With reference to FIG. 2/Table 2, the synthesis of $TEAPYO_{15}Cl_2$:
1) TEA and PYO are purified by vacuum distillation.
2) TEA and PYO and 1,5-Dichloropentane are mixed at a mole ratio of 1:1:1.1
3) Adding acetone which is in the same volume as the 1,5-Dichloropentane
4) Mix and stir at 45° C. for 12 hours.
5) Acetone is distilled off and the remaining liquid is $TEAPYO_{15}Cl_2$.

With reference to FIG. 2/Table 2, the synthesis of $MIMMPE_{15}Cl_2$:
1) MIM and MPE are purified by vacuum distillation.
2) MIM and MPE and 1,5-Dichloropentane are mixed at a mole ratio of 1:1:1.1
3) Adding acetone which is in the same volume as the 1,5-Dichloropentane
4) Mix and stir at 25° C. for 12 hours.
5) Acetone is distilled off and the remaining liquid is $MIMMPE_{15}Cl_2$.

With reference to FIG. 2/Table 2, the synthesis of $MIMPYO_{15}Cl_2$:
1) MIM and PYO are purified by vacuum distillation.
2) MIM and PYO and 1,5-Dichloropentane are mixed at a mole ratio of 1:1:1.1
3) Adding acetone which is in the same volume as the 1,5-Dichloropentane
4) Mix and stir at 25° C. for 12 hours.
5) Acetone is distilled off and the remaining liquid is $MIMPYO_{15}Cl_2$.

Step 2. Synthesis of Two-Core Cationic Chain Ionic Liquid

1. Taking the synthesis of 1,4-bis(1-methylpyrrolidium 1-yl) butane dihexafluorophosphate $[DiPYR_{14}(PF_6)_2]$ as an example: 1,4-bis(1-methylpyrrolidium 1-yl) butane dichloride $(DiPYR_{14}Cl_2)$ synthesized in Step 1 is added to an equal weight of acetone (as a mixed solvent). followed by adding twice as many mole of potassium hexafluorophosphate. It is stirred at 70° C. for 16 hours. After filtering the white precipitate potassium chloride KCl, the remaining liquid is distilled under reduced pressure to remove the acetone, and then recrystallized to form $DiPYR_{14}(PF_6)_2$. Finally, the synthesized product is filtered, purified and dried in a vacuum oven at 60° C. until its water content is less than 20 ppm. The synthesis parameters of other series of $DiPYR_{1R}(PF_6)_2$ and $DiPIP_{1R}(PF_6)_2$ ionic liquids are shown in FIG. 3A or Table 3.

With reference to FIG. 3A/Table 3, the synthesis of $DiPYR_{14}(PF_6)_2$:
1) $DiPYR_{14}Cl_2$ synthesized in Step 1 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPYR_{14}(PF_6)_2$
7) The product is filtered, purified and dried in a vacuum oven at 60° C. until its water content is less than 20 ppm.

With reference to FIG. 3A/Table 3, the synthesis of $DiPYR_{15}(PF_6)_2$:
1) $DiPYR_{15}Cl_2$ synthesized in Step 1 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPYR_{15}(PF_6)_2$.
7) The product is filtered, purified and dried in a vacuum oven at 60° C. until its water content is less than 20 ppm.

With reference to FIG. 3A/Table 3, the synthesis of $DiPYR_{16}(PF_6)_2$:
1) $DiPYR_{16}Cl_2$ synthesized in Step 1 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPYR_{16}(PF_6)_2$
7) The product is filtered, purified and dried in a vacuum oven at 60° C. until its water content is less than 20 ppm.

With reference to FIG. 3A/Table 3, the synthesis of $DiPYR_{18}(PF_6)_2$:
1) $DiPYR_{18}Cl_2$ synthesized in Step 1 is added to an equal weight of acetone.

2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPYR_{18}(PF_6)_2$.
7) The product is filtered, purified and dried in a vacuum oven at 60° C. until its water content is less than 20 ppm.

With reference to FIG. 3A/Table 3, the synthesis of $DiPIP_{14}(PF_6)_2$:
1) $DiPIP_{14}(PF_6)_2$ synthesized in Step 2 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPIP_{14}(PF_6)_2$
7) The product is filtered, purified and dried in a vacuum oven at 60° C. until its water content is less than 20 ppm.

With reference to FIG. 3A/Table 3, the synthesis of $DiPIP_{15}(PF_6)_2$:
1) $DiPIP_{15}Cl_2$ synthesized in Step 2 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPIP_{15}(PF_6)_2$.
7) The product is filtered, purified and dried in a vacuum oven at 60° C. until its water content is less than 20 ppm.

With reference to FIG. 3A/Table 3, the synthesis of $DiPIP_{16}(PF_6)_2$:
1) $DiPIP_{16}Cl_2$ synthesized in Step 2 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPIP_{16}(PF_6)_2$.
7) The product is filtered, purified and dried in a vacuum oven at 60° C. until its water content is less than 20 ppm.

With reference to FIG. 3A/Table 3, the synthesis of $DiPIP_{18}(PF_6)_2$:
1) $DiPIP_{18}Cl_2$ synthesized in Step 2 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $DiPIP_{18}(PF_6)_2$.
7) The product is filtered, purified and dried in a vacuum oven at 60° C. until its water content is less than 20 ppm.

2. Replacing the cation $X_1$ and $X_2$ with other heterocyclic aromatics or amine, including imidazolium, quaternary ammonium, piperidinium, pyrrolidinium, morpholinium, and triethylamine etc. Taking the synthesis of 1,5-(1-methylpyrrolidium 1-yl)(1-methyl piperidinium 1-yl) pentane dihexafluorophosphate $[PYRPIP_{15}(PF_6)_2]$ as an example: The 1,5-(1-methylpyrrolidium 1-yl)(1-methylpiperidinium 1-yl) pentane dichloride ($PYRPIP_{15}Cl_2$) synthesized in Step 1 is added to an equal weight of acetone (as a mixed solvent). Twice the mole of potassium hexafluorophosphate is then added. It is stirred at 70° C. for 16 hours. After the white precipitate potassium chloride KCl is filtered, the remaining liquid is distilled under reduced pressure to remove the acetone, and then recrystallized to form $PYRPIP_{15}(PF_6)_2$. Finally, the synthesized product is filtered and purified and dried in a vacuum oven at 60° C. until its water content is less than 20 ppm. The synthesis parameters of other series of two-core cationic chain ionic liquids are shown in FIGS. 3A, 3B or Table 3.

With reference to FIG. 3A/Table 3, the synthesis of $PYRPIP_{15}(PF_6)_2$:
1) $PYRPIP_{15}Cl_2$ synthesized in Step 2 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $PYRPIP_{15}(PF_6)_2$
7) The product is filtered, purified and dried in a vacuum oven at 60° C. until its water content is less than 20 ppm.

With reference to FIG. 3A/Table 3, the synthesis of $PYRTEA_{15}(PF_6)_2$:
1) $PYRTEA_{15}Cl_2$ synthesized in Step 2 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $PYRTEA_{15}(PF_6)_2$
7) The product is filtered, purified and dried in a vacuum oven at 60° C. until its water content is less than 20 ppm.

With reference to FIG. 3A/Table 3, the synthesis of $PYRMPE_{15}(PF_6)_2$:
1) $PYRMPE_{15}Cl_2$ synthesized in Step 2 is added to an equal weight of acetone.
2) Adding twice as many moles of potassium hexafluorophosphate.
3) Stir at 45° C. for 12 hours.
4) Filtering the white precipitate KCl.
5) Distill the remaining liquid under reduced pressure to remove the acetone.
6) Recrystallize to form $PYRMPE_{15}(PF_6)_2$
7) The product is filtered, purified and dried in a vacuum oven at 60° C. until its water content is less than 20 ppm.

With reference to FIG. 3A/Table 3, the synthesis of $PYRMIM_{15}(PF_6)_2$:
1) $PYRMIM_{15}Cl_2$ synthesized in Step 2 is added to an equal weight of acetone.
2) Adding twice as many moles of potassium hexafluorophosphate.

3) Stir at 25° C. for 12 hours.
4) Filtering the white precipitate KCl.
5) Distill the remaining liquid under reduced pressure to remove the acetone.
6) Recrystallize to form $PYRMIM_{15}(PF_6)_2$
7) The product is filtered, purified and dried in a vacuum oven at 60° C. until its water content is less than 20 ppm.

With reference to FIG. 3A/Table 3, the synthesis of $PYRPYO_{15}(PF_6)_2$:
1) $PYRPYO_{15}Cl_2$ synthesized in Step 2 is added to an equal weight of acetone.
2) Adding twice as many moles of potassium hexafluorophosphate.
3) Stir at 45° C. for 12 hours.
4) Filtering the white precipitate KCl.
5) Distill the remaining liquid under reduced pressure to remove the acetone.
6) Recrystallize to form $PYRPYO_{15}(PF_6)_2$
7) The product is filtered, purified and dried in a vacuum oven at 60° C. until its water content is less than 20 ppm.

With reference to FIG. 3A/Table 3, the synthesis of $PIPTEA_{15}(PF_6)_2$:
1) $PIPTEA_{15}Cl_2$ synthesized in Step 2 is added to an equal weight of acetone.
2) Adding twice as many moles of potassium hexafluorophosphate.
3) Stir at 70° C. for 16 hours.
4) Filtering the white precipitate KCl.
5) Distill the remaining liquid under reduced pressure to remove the acetone.
6) Recrystallize to form $PIPTEA_{15}(PF_6)_2$
7) The product is filtered, purified and dried in a vacuum oven at 60° C. until its water content is less than 20 ppm.

With reference to FIG. 3A/Table 3, the synthesis of $PIPMPE_{15}(PF_6)_2$:
1) $PIPMPE_{15}Cl_2$ synthesized in Step 2 is added to an equal weight of acetone.
2) Adding twice as many moles of potassium hexafluorophosphate.
3) Stir at 45° C. for 12 hours.
4) Filtering the white precipitate KCl.
5) Distill the remaining liquid under reduced pressure to remove the acetone.
6) Recrystallize to form $PIPMPE_{15}(PF_6)_2$
7) The product is filtered, purified and dried in a vacuum oven at 60° C. until its water content is less than 20 ppm.

With reference to FIG. 3A/Table 3, the synthesis of $PIPMIM_{15}(PF_6)_2$:
1) $PIPMIM_{15}Cl_2$ synthesized in Step 2 is added to an equal weight of acetone.
2) Adding twice as many moles of potassium hexafluorophosphate.
3) Stir at 25° C. for 12 hours.
4) Filtering the white precipitate KCl.
5) Distill the remaining liquid under reduced pressure to remove the acetone.
6) Recrystallize to form $PIPMIM_{15}(PF_6)_2$.
7) The product is filtered, purified and dried in a vacuum oven at 60° C. until its water content is less than 20 ppm.

With reference to FIG. 3A/Table 3, the synthesis of $PIPPYO_{15}(PF_6)_2$:
1) $PIPPYO_{15}Cl_2$ synthesized in Step 2 is added to an equal weight of acetone.
2) Adding twice as many moles of potassium hexafluorophosphate.
3) Stir at 45° C. for 12 hours.
4) Filtering the white precipitate KCl.
5) Distill the remaining liquid under reduced pressure to remove the acetone.
6) Recrystallize to form $PIPPYO_{15}(PF_6)_2$.
7) The product is filtered, purified and dried in a vacuum oven at 60° C. until its water content is less than 20 ppm.

With reference to FIG. 3A/Table 3, the synthesis of $TEAMPE_{15}(PF_6)_2$:
1) $TEAMPE_{15}Cl_2$ synthesized in Step 2 is added to an equal weight of acetone.
2) Adding twice as many moles of potassium hexafluorophosphate.
3) Stir at 45° C. for 12 hours.
4) Filtering the white precipitate KCl.
5) Distill the remaining liquid under reduced pressure to remove the acetone.
6) Recrystallize to form $TEAMPE_{15}(PF_6)_2$.
7) The product is filtered, purified and dried in a vacuum oven at 60° C. until its water content is less than 20 ppm.

With reference to FIG. 3A/Table 3, the synthesis of $TEAMIM_{15}(PF_6)_2$:
1) $TEAMIM_{15}Cl_2$ synthesized in Step 2 is added to an equal weight of acetone.
2) Adding twice as many moles of potassium hexafluorophosphate.
3) Stir at 25° C. for 12 hours.
4) Filtering the white precipitate KCl.
5) Distill the remaining liquid under reduced pressure to remove the acetone.
6) Recrystallize to form $TEAMIM_{15}(PF_6)_2$.
7) The product is filtered, purified and dried in a vacuum oven at 60° C. until its water content is less than 20 ppm.

With reference to FIG. 3B/Table 3, the synthesis of $TEAPYO_{15}(PF_6)_2$:
1) $TEAPYO_{15}Cl_2$ synthesized in Step 2 is added to an equal weight of acetone.
2) Adding twice as many moles of potassium hexafluorophosphate.
3) Stir at 45° C. for 12 hours.
4) Filtering the white precipitate KCl.
5) Distill the remaining liquid under reduced pressure to remove the acetone.
6) Recrystallize to form $TEAPYO_{15}(PF_6)_2$
7) The product is filtered, purified and dried in a vacuum oven at 60° C. until its water content is less than 20 ppm.

With reference to FIG. 3B/Table 3, the synthesis of $MIMMPE_{15}(PF_6)_2$:
1) $MIMMPE_{15}Cl_2$ synthesized in Step 2 is added to an equal weight of acetone.
2) Adding twice as many moles of potassium hexafluorophosphate.
3) Stir at 25° C. for 12 hours.
4) Filtering the white precipitate KCl.
5) Distill the remaining liquid under reduced pressure to remove the acetone.
6) Recrystallize to form $MIMMPE_{15}(PF_6)_2$ 7) The product is filtered, purified and dried in a vacuum oven at 60° C. until its water content is less than 20 ppm.

With reference to FIG. 3B/Table 3, the synthesis of MIMPYO$_{15}$(PF$_6$)$_2$:
1) MIMPYO$_{15}$Cl$_2$ synthesized in Step 2 is added to an equal weight of acetone.
2) Adding twice as many moles of potassium hexafluorophosphate.
3) Stir at 25° C. for 12 hours.
4) Filtering the white precipitate KCl.
5) Distill the remaining liquid under reduced pressure to remove the acetone.
6) Recrystallize to form MIMPYO$_{15}$(PF$_6$)$_2$
7) The product is filtered, purified and dried in a vacuum oven at 60° C. until its water content is less than 20 ppm.

3. Replacing the other anion Z$_1$ and Z$_2$, which may include PF$_6^-$ (hexafluorophosphate), POF$_2^-$ (difluorophosphate), BF$_4^-$ (tetrafluoroborate), B(C$_2$O$_4$)$_2^-$ (BOB$^-$, bis(oxalato) borate), BF$_2$(C$_2$O$_4$)$^-$ (ODFB$^-$, difluoro(oxalato)borate), CF$_3$BF$_3^-$ (trifluoromethyltrifluoroborate), (FSO$_2$)$_2$N$^-$ (FSI$^-$, bis(fluorosulfonyl)imide), (CF$_3$SO$_2$)$_2$N (TFSI$^-$, bis (trifluoromethane)sulfonamide), CH$_3$SO$_4^-$ (MeSO$_4^-$, methyl sulfate), etc.

Taking the synthesis of 1,5-(1-methylpyrrolidium 1-yl)(1-methylpiperidinium) 1-yl) pentane hexafluorophosphate tetrafluoroborate [PYRPIP$_{15}$(PF$_6$)(BF$_4$)] as an example. The 1,5-(1-methylpyrrolidium 1-yl)(1-methylpiperidinium 1-yl) pentane dichloride (PYRPIP$_{15}$Cl$_2$) synthesized in Step 1 is added to an equal weight of acetone (as a mixed solvent) followed by the addition of same mole of potassium hexafluorophosphate and potassium tetrafluoroborate. It is stirred at 70° C. for 16 hours. After the white precipitate potassium chloride KCl is filtered, the remaining liquid is distilled under reduced pressure to remove the acetone, and then recrystallized to form PYRPIP$_{15}$ (PF$_6$)(BF$_4$). Finally, the synthesized product is filtered, purified, and dried in a vacuum oven at 60° C. to until its water content is below 20 ppm. The synthesis parameters of other series of two-core cationic chain ionic liquids are shown in FIGS. 3A/3B/Table 3.

With reference to FIG. 3A/Table 3, the synthesis of DiPYR$_{14}$(PF$_6$) (BF$_4$):
1) DiPYR$_{14}$Cl$_2$ synthesized in Step 1 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form DiPYR$_{14}$(PF$_6$) (BF$_4$).
7) The product is filtered, purified and dried in a vacuum oven at 60° C. until its water content is less than 20 ppm.

With reference to FIG. 3A/Table 3, the synthesis of DiPYR$_{15}$(PF$_6$) (BF$_4$):
1) DiPYR$_{15}$Cl$_2$ synthesized in Step 1 is added to an equal weight of acetone
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form DiPYR$_{15}$(PF$_6$) (BF$_4$).
7) The product is filtered, purified and dried in a vacuum oven at 60° C. until its water content is less than 20 ppm.

With reference to FIG. 3A/Table 3, the synthesis of DiPYR$_{16}$(PF$_6$) (BF$_4$):
1) DiPYR$_{16}$Cl$_2$ synthesized in Step 1 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form DiPYR$_{16}$(PF$_6$) (BF$_4$).
7) The product is filtered, purified and dried in a vacuum oven at 60° C. until its water content is less than 20 ppm.

With reference to FIG. 3A/Table 3, the synthesis of DiPYR$_{18}$(PF$_6$) (BF$_4$):
1) DiPYR$_{18}$Cl$_2$ synthesized in Step 1 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form DiPYR$_{18}$(PF$_6$) (BF$_4$).
7) The product is filtered, purified and dried in a vacuum oven at 60° C. until its water content is less than 20 ppm.

With reference to FIG. 3A/Table 3, the synthesis of DiPIP$_{14}$(PF$_6$) (BF$_4$):
1) DiPIP$_{14}$Cl$_2$ synthesized in Step 2 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form DiPIP$_{14}$(PF$_6$) (BF$_4$).
7) The product is filtered, purified and dried in a vacuum oven at 60° C. until its water content is less than 20 ppm.

With reference to FIG. 3A/Table 3, the synthesis of DiPIP$_{15}$(PF$_6$) (BF$_4$):
1) DiPIP$_{15}$Cl$_2$ synthesized in Step 2 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form DiPIP$_{15}$(PF$_6$) (BF$_4$).
7) The product is filtered, purified and dried in a vacuum oven at 60° C. until its water content is less than 20 ppm.

With reference to FIG. 3A/Table 3, the synthesis of DiPIP$_{16}$(PF$_6$) (BF$_4$):
1) DiPIP$_{16}$Cl$_2$ synthesized in Step 2 is added to an equal weight of acetone.
2) Adding same mole of potassium hexafluorophosphate and potassium tetrafluoroborate.
3) Stir at 70° C. for 16 hours.

4) Filtering the white precipitate KCl.
5) Distill the remaining liquid under reduced pressure to remove the acetone.
6) Recrystallize to form $DiPIP_{16}(PF_6)(BF_4)$.
7) The product is filtered, purified and dried in a vacuum oven at 60° C. until its water content is less than 20 ppm.

With reference to FIG. 3A/Table 3, the synthesis of $DiPIP_{18}(PF_6)(BF_4)$:
1) $DiPIP_{18}Cl_2$ synthesized in Step 2 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form $DiPIP_{18}(PF_6)(BF_4)$.
7) The product is filtered, purified and dried in a vacuum oven at 60° C. until its water content is less than 20 ppm.

With reference to FIG. 3B/Table 3, the synthesis of $PYRPIP_{15}(PF_6)(BF_4)$:
1) $PYRPIP_{15}Cl_2$ synthesized in Step 2 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form $PYRPIP_{15}(PF_6)(BF_4)$.
7) The product is filtered, purified and dried in a vacuum oven at 60° C. until its water content is less than 20 ppm.

With reference to FIG. 3B/Table 3, the synthesis of $PYRTEA_{15}(PF_6)(BF_4)$:
1) $PYRTEA_{15}Cl_2$ synthesized in Step 2 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form $PYRTEA_{15}(PF_6)(BF_4)$.
7) The product is filtered, purified and dried in a vacuum oven at 60° C. until its water content is less than 20 ppm.

With reference to FIG. 3B/Table 3, the synthesis of $PYRMPE_{15}(PF_6)(BF_4)$:
1) $PYRMPE_{15}Cl_2$ synthesized in Step 2 is added to an equal weight of acetone.
2) Adding same mole of potassium hexafluorophosphate and potassium tetrafluoroborate.
3) Stir at 45° C. for 12 hours.
4) Filtering the white precipitate KCl.
5) Distill the remaining liquid under reduced pressure to remove the acetone.
6) Recrystallize to form $PYRMPE_{15}(PF_6)(BF_4)$.
7) The product is filtered, purified and dried in a vacuum oven at 60° C. until its water content is less than 20 ppm.

With reference to FIG. 3B/Table 3, the synthesis of $PYRMIM_{15}(PF_6)(BF_4)$:
1) $PYRMIM_{15}Cl_2$ synthesized in Step 2 is added to an equal weight of acetone.
2) Adding same mole of potassium hexafluorophosphate and potassium tetrafluoroborate.
3) Stir at 25° C. for 12 hours.
4) Filtering the white precipitate KCl.
5) Distill the remaining liquid under reduced pressure to remove the acetone.
6) Recrystallize to form $PYRMIM_{15}(PF_6)(BF_4)$.
7) The product is filtered, purified and dried in a vacuum oven at 60° C. until its water content is less than 20 ppm.

With reference to FIG. 3B/Table 3, the synthesis of $PYRPYO_{15}(PF_6)(BF_4)$:
1) $PYRPYO_{15}Cl_2$ synthesized in Step 2 is added to an equal weight of acetone.
2) Adding same mole of potassium hexafluorophosphate and potassium tetrafluoroborate.
3) Stir at 45° C. for 12 hours.
4) Filtering the white precipitate KCl.
5) Distill the remaining liquid under reduced pressure to remove the acetone.
6) Recrystallize to form $PYRPYO_{15}(PF_6)(BF_4)$.
7) The product is filtered, purified and dried in a vacuum oven at 60° C. until its water content is less than 20 ppm.

With reference to FIG. 3B/Table 3, the synthesis of $PIPTEA_{15}(PF_6)(BF_4)$:
1) $PIPTEA_{15}Cl_2$ synthesized in Step 2 is added to an equal weight of acetone.
2) Adding same mole of potassium hexafluorophosphate and potassium tetrafluoroborate.
3) Stir at 70° C. for 16 hours.
4) Filtering the white precipitate KCl.
5) Distill the remaining liquid under reduced pressure to remove the acetone.
6) Recrystallize to form $PIPTEA_{15}(PF_6)(BF_4)$.
7) The product is filtered, purified and dried in a vacuum oven at 60° C. until its water content is less than 20 ppm.

With reference to FIG. 3B/Table 3, the synthesis of $PIPMPE_{15}(PF_6)(BF_4)$:
1) $PIPMPE_{15}Cl_2$ synthesized in Step 2 is added to an equal weight of acetone.
2) Adding same mole of potassium hexafluorophosphate and potassium tetrafluoroborate.
3) Stir at 45° C. for 12 hours.
4) Filtering the white precipitate KCl.
5) Distill the remaining liquid under reduced pressure to remove the acetone.
6) Recrystallize to form $PIPMPE_{15}(PF_6)(BF_4)$.
7) The product is filtered, purified and dried in a vacuum oven at 60° C. until its water content is less than 20 ppm.

With reference to FIG. 3B/Table 3, the synthesis of $PIPMIM_{15}(PF_6)(BF_4)$:
1) $PIPMIM_{15}Cl_2$ synthesized in Step 2 is added to an equal weight of acetone.
2) Adding same mole of potassium hexafluorophosphate and potassium tetrafluoroborate.
3) Stir at 25° C. for 12 hours.
4) Filtering the white precipitate KCl.
5) Distill the remaining liquid under reduced pressure to remove the acetone.
6) Recrystallize to form $PIPMIM_{15}(PF_6)(BF_4)$.
7) The product is filtered, purified and dried in a vacuum oven at 60° C. until its water content is less than 20 ppm.

With reference to FIG. 3B/Table 3, the synthesis of PIPPYO$_{15}$(PF$_6$)(BF$_4$):
1) PIPPYO$_{15}$Cl$_2$ synthesized in Step 2 is added to an equal weight of acetone.
2) Adding same mole of potassium hexafluorophosphate and potassium tetrafluoroborate.
3) Stir at 45° C. for 12 hours.
4) Filtering the white precipitate KCl.
5) Distill the remaining liquid under reduced pressure to remove the acetone.
6) Recrystallize to form PIPPYO$_{15}$(PF$_6$)(BF$_4$).
7) The product is filtered, purified and dried in a vacuum oven at 60° C. until its water content is less than 20 ppm.

With reference to FIG. 3B/Table 3, the synthesis of TEAMPE$_{15}$(PF$_6$)(BF$_4$):
1) TEAMPE$_{15}$Cl$_2$ synthesized in Step 2 is added to an equal weight of acetone.
2) Adding same mole of potassium hexafluorophosphate and potassium tetrafluoroborate.
3) Stir at 45° C. for 12 hours.
4) Filtering the white precipitate KCl.
5) Distill the remaining liquid under reduced pressure to remove the acetone.
6) Recrystallize to form TEAMPE$_{15}$(PF$_6$)(BF$_4$).
7) The product is filtered, purified and dried in a vacuum oven at 60° C. until its water content is less than 20 ppm.

With reference to FIG. 3B/Table 3, the synthesis of TEAMIM$_{15}$(PF$_6$)(BF$_4$):
1) TEAMIM$_{15}$Cl$_2$ synthesized in Step 2 is added to an equal weight of acetone.
2) Adding same mole of potassium hexafluorophosphate and potassium tetrafluoroborate.
3) Stir at 25° C. for 12 hours
4) Filtering the white precipitate KCl.
5) Distill the remaining liquid under reduced pressure to remove the acetone.
6) Recrystallize to form TEAMIM$_{15}$(PF$_6$)(BF$_4$).
7) The product is filtered, purified and dried in a vacuum oven at 60° C. until its water content is less than 20 ppm.

With reference to FIG. 3B/Table 3, the synthesis of TEAPYO$_{15}$(PF$_6$)(BF$_4$):
1) TEAPYO$_{15}$Cl$_2$ synthesized in Step 2 is added to an equal weight of acetone.
2) Adding same mole of potassium hexafluorophosphate and potassium tetrafluoroborate.
3) Stir at 45° C. for 12 hours.
4) Filtering the white precipitate KCl.
5) Distill the remaining liquid under reduced pressure to remove the acetone.
6) Recrystallize to form TEAPYO$_{15}$(PF$_6$)(BF$_4$).
7) The product is filtered, purified and dried in a vacuum oven at 60° C. until its water content is less than 20 ppm.

With reference to FIG. 3B/Table 3, the synthesis of MIMMPE$_{15}$(PF$_6$)(BF$_4$):
1) MIMMPE$_{15}$Cl$_2$ synthesized in Step 2 is added to an equal weight of acetone.
2) Adding same mole of potassium hexafluorophosphate and potassium tetrafluoroborate.
3) Stir at 25° C. for 12 hours.
4) Filtering the white precipitate KCl.
5) Distill the remaining liquid under reduced pressure to remove the acetone.
6) Recrystallize to form MIMMPE$_{15}$(PF$_6$)(BF$_4$):
7) The product is filtered, purified and dried in a vacuum oven at 60° C. until its water content is less than 20 ppm.

With reference to FIG. 3B/Table 3, the synthesis of MIMPYO$_{15}$(PF$_6$)(BF$_4$):
1) MIMPYO$_{15}$Cl$_2$ synthesized in Step 2 is added to an equal weight of acetone.
2) Adding same mole of potassium hexafluorophosphate and potassium tetrafluoroborate.
3) Stir at 25° C. for 12 hours.
4) Filtering the white precipitate KCl.
5) Distill the remaining liquid under reduced pressure to remove the acetone.
6) Recrystallize to form MIMPYO$_{15}$(PF$_6$)(BF$_4$).
7) The product is filtered, purified and dried in a vacuum oven at 60° C. until its water content is less than 20 ppm.

With reference to FIG. 3B/Table 3, the synthesis of DiPYR$_{15}$(TFSI)(FSI):
1) DiPYR$_{15}$Cl$_2$ synthesized in Step 1 is added to an equal weight of acetone.
2) Adding same mole of lithium trifluoromethanesulfonimide and lithium bis(fluorosulfonyl)imide.
3) Stir at 70° C. for 16 hours.
4) Filtering the white precipitate LiCl.
5) Distill the remaining liquid under reduced pressure to remove the acetone.
6) Recrystallize to form DiPYR$_{15}$(TFSI)(FSI).
7) The product is filtered, purified and dried in a vacuum oven at 60° C. until its water content is less than 20 ppm.

With reference to FIG. 3B/Table 3, the synthesis of DiPIP$_{15}$(TFSI)(FSI):
1) DiPIP$_{15}$Cl$_2$ synthesized in Step 2 is added to an equal weight of acetone.
2) Adding same mole of lithium bis(trifluoromethane)sulfonimide and lithium bis(fluorosulfonyl)imide.
3) Stir at 70° C. for 16 hours.
4) Filtering the white precipitate LiCl.
5) Distill the remaining liquid under reduced pressure to remove the acetone.
6) Recrystallize to form DiPIP$_{15}$(TFSI)(FSI).
7) The product is filtered, purified and dried in a vacuum oven at 60° C. until its water content is less than 20 ppm.

With reference to FIG. 3B/Table 3, the synthesis of PYRPIP$_{15}$(TFSI)(FSI):
1) PYRPIP$_{15}$Cl$_2$ synthesized in Step 2 is added to an equal weight of acetone.
2) Adding same mole of lithium bis(trifluoromethane)sulfonimide and lithium bis(fluorosulfonyl)imide.
3) Stir at 70° C. for 16 hours.
4) Filtering the white precipitate LiCl.
5) Distill the remaining liquid under reduced pressure to remove the acetone.
6) Recrystallize to form PYRPIP$_{15}$(TFSI)(FSI).
7) The product is filtered, purified and dried in a vacuum oven at 60° C. until its water content is less than 20 ppm.

With reference to FIG. 3B/Table 3, the synthesis of PYRTEA$_{15}$(TFSI)(FSI):
1) PYRTEA$_{15}$Cl$_2$ synthesized in Step 2 is added to an equal weight of acetone.
2) Adding same mole of lithium bis(trifluoromethane)sulfonimide and lithium bis(fluorosulfonyl)imide.
3) Stir at 70° C. for 16 hours.
4) Filtering the white precipitate LiCl.

5) Distill the remaining liquid under reduced pressure to remove the acetone.
6) Recrystallize to form PYRTEA$_{15}$(TFSI)(FSI).
7) The product is filtered, purified and dried in a vacuum oven at 60° C. until its water content is less than 20 ppm.

With reference to FIG. 3B/Table 3, the synthesis of PIPTEA$_{15}$(TFSI)(FSI):
1) PIPTEA$_{15}$Cl$_2$ synthesized in Step 2 is added to an equal weight of acetone.
2) Adding same mole of lithium bis(trifluoromethane) sulfonimide and lithium bis(fluorosulfonyl)imide
3) Stir at 70° C. for 16 hours.
4) Filtering the white precipitate LiCl.
5) Distill the remaining liquid under reduced pressure to remove the acetone.
6) Recrystallize to form PIPTEA$_{15}$(TFSI)(FSI).
7) The product is filtered, purified and dried in a vacuum oven at 60° C. until its water content is less than 20 ppm.

With reference to FIG. 3B/Table 3, the synthesis of DiPYR$_{15}$(CF$_3$BF$_3$)(POF$_2$):
1) DiPYR$_{15}$Cl$_2$ synthesized in Step 1 is added to an equal weight of acetone.
2) Adding same mole of lithium (trifluoromethyl)trifluoroborate and lithium difluorophosphate.
3) Stir at 70° C. for 16 hours.
4) Filtering the white precipitate LiCl.
5) Distill the remaining liquid under reduced pressure to remove the acetone.
6) Recrystallize to form DiPYR$_{15}$(CF$_3$BF$_3$)(POF$_2$).
7) The product is filtered, purified and dried in a vacuum oven at 60° C. until its water content is less than 20 ppm.

With reference to FIG. 3B/Table 3, the synthesis of DiPIP$_{15}$(CF$_3$BF$_3$)(POF$_2$):
1) DiPIP$_{15}$Cl$_2$ synthesized in Step 2 is added to an equal weight of acetone.
2) Adding same mole of lithium (trifluoromethyl)trifluoroborate and lithium difluorophosphate.
3) Stir at 70° C. for 16 hours.
4) Filtering the white precipitate LiCl.
5) Distill the remaining liquid under reduced pressure to remove the acetone.
6) Recrystallize to form DiPIP$_{15}$(CF$_3$BF$_3$)(POF$_2$).
7) The product is filtered, purified and dried in a vacuum oven at 60° C. until its water content is less than 20 ppm.

With reference to FIG. 3B/Table 3, the synthesis of PYRPIP$_{15}$(CF$_3$BF$_3$)(POF$_2$):
1) PYRPIP$_{15}$Cl$_2$ synthesized in Step 2 is added to an equal weight of acetone.
2) Adding same mole of lithium (trifluoromethyl)trifluoroborate and lithium difluorophosphate.
3) Stir at 70° C. for 16 hours.
4) Filtering the white precipitate LiCl.
5) Distill the remaining liquid under reduced pressure to remove the acetone.
6) Recrystallize to form PYRPIP$_{15}$(CF$_3$BF$_3$)(POF$_2$).
7) The product is filtered, purified and dried in a vacuum oven at 60° C. until its water content is less than 20 ppm.

With reference to FIG. 3B/Table 3, the synthesis of PYRTEA$_{15}$(CF$_3$BF$_3$)(POF$_2$):
1) PYRTEA$_{15}$Cl$_2$ synthesized in Step 2 is added to an equal weight of acetone.
2) Adding same mole of lithium (trifluoromethyl)trifluoroborate and lithium difluorophosphate.
3) Stir at 70° C. for 16 hours.
4) Filtering the white precipitate LiCl.
5) Distill the remaining liquid under reduced pressure to remove the acetone.
6) Recrystallize to form PYRTEA$_{15}$(CF$_3$BF$_3$)(POF$_2$).
7) The product is filtered, purified and dried in a vacuum oven at 60° C. until its water content is less than 20 ppm.

With reference to FIG. 3B/Table 3, the synthesis of PIPTEA$_{15}$(CF$_3$BF$_3$)(POF$_2$):
1) PIPTEA$_{15}$Cl$_2$ synthesized in Step 2 is added to an equal weight of acetone.
2) Adding same mole of lithium (trifluoromethyl)trifluoroborate and lithium difluorophosphate.
3) Stir at 70° C. for 16 hours.
4) Filtering the white precipitate LiCl.
5) Distill the remaining liquid under reduced pressure to remove the acetone.
6) Recrystallize to form PIPTEA$_{15}$(CF$_3$BF$_3$)(POF$_2$).
7) The product is filtered, purified and dried in a vacuum oven at 60° C. until its water content is less than 20 ppm.

Embodiment 2

Synthesis of Ionic Liquid with the Aromatic Functional Group Bonded to a Cation (Structural Formula II: Z$_1$X$_1$YW)

Step 1. Synthesis of Aromatic Group Bonded to Cation Halide

1. Taking the synthesis of benzyl-2-(1-methylpyrrolidinium 1-yl) ethyl ether chloride (Benzyl-PYR$_{IEE}$Cl) as an example. Firstly, N-methyl pyrrolidine (NMPD) is purified by distillation at 85° C. Then NMPD and Benzyl 2-chloroethyl ether are mixed at the mole ratio of 1:1.1 followed by adding acetone of the same volume as the benzyl-2-chloroethyl ether. It is mixed and stirred at 70° C. for 12 hours. Acetone is distilled off with the remaining liquid being benzyl-PYR$_{IEE}$Cl. The synthesis parameters of other series of aromatic bonded to 1-methylpyrrolidinium halide are shown in FIG. 4/Table 4.

2. The synthesis of 1-(2-Furoyl)-1-methyl pyrrolidinium chloride (Furoyl-PYR$_{11}$Cl) as an example. First, N-methyl pyrrolidine (NMPD) is purified by distillation at 85° C. Then NMPD and 2-Furoyl chloride are mixed at a mole ratio of 1:1.1 followed by adding acetone at the same volume as the 2-furoyl chloride. It is then mixed and stirred at 70° C. for 12 hours. Acetone is removed by distillation and the remaining liquid is Furoyl-PYR$_{11}$Cl. The synthesis parameters of other series of aromatic bonded to 1-methylpyrrolidinium halide are shown in FIG. 4/Table 4.

With reference to FIG. 4/Table 4, the synthesis of Benzyl-PYR$_{IEE}$Cl:
1) NMPD is purified by distillation at 85° C.
2) NMPD and Benzyl-2-chloroethyl ether are mixed at the mole ratio of 1:1.1.
3) Adding acetone of the same volume as the Benzyl-2-chloroethyl ether.
4) Mix and stir at 70° C. for 12 hours.
5) Acetone is distilled off with the remaining liquid being Benzyl-PYR$_{IEE}$Cl.

With reference to FIG. 4/Table 4, the synthesis of Benzyl-PYR$_{IBE}$Cl:
1) NMPD is purified by distillation at 85° C.
2) NMPD and Benzyl-4-chloro butyl ether are mixed at the mole ratio of 1:1.1.
3) Adding acetone of the same volume as the Benzyl-4-chloro butyl ether.
4) Mix and stir at 70° C. for 12 hours.
5) Acetone is distilled off with the remaining liquid being Benzyl-PYR$_{IBE}$Cl.

With reference to FIG. 4/Table 4, the synthesis of Benzoyl-PYR$_{11}$Cl:
1) NMPD is purified by distillation at 85° C.
2) NMPD and Benzoyl chloride are mixed at the mole ratio of 1:1.1.
3) Adding acetone of the same volume as the Benzoyl chloride.
4) Mix and stir at 70° C. for 12 hours.
5) Acetone is distilled off with the remaining liquid being Benzoyl-PYR$_{11}$Cl.

With reference to FIG. 4/Table 4, the synthesis of Phenacyl-PYR$_{11}$Cl:
1) NMPD is purified by distillation at 85° C.
2) NMPD and Phenacyl chloride are mixed at the mole ratio of 1:1.1.
3) Adding acetone of the same volume as the Phenacyl chloride.
4) Mix and stir at 70° C. for 12 hours.
5) Acetone is distilled off with the remaining liquid being Phenacyl-PYR$_{11}$Cl.

With reference to FIG. 4/Table 4, the synthesis of Furan-PYR$_{11}$Cl:
1) NMPD is purified by distillation at 85° C.
2) NMPD and 2-Chlorofuran are mixed at the mole ratio of 1:1.1.
3) Adding acetone of the same volume as the 2-Chlorofuran.
4) Mix and stir at 70° C. for 12 hours.
5) Acetone is distilled off with the remaining liquid being Furan-PYR$_{11}$Cl.

With reference to FIG. 4/Table 4, the synthesis of Furan-PYR$_{14}$Cl:
1) NMPD is purified by distillation at 85° C.
2) NMPD and 2-(4-chlorobutyl)furan are mixed at the mole ratio of 1:1.1.
3) Adding acetone of the same volume as the 2-(4-chlorobutyl)furan.
4) Mix and stir at 70° C. for 12 hours.
5) Acetone is distilled off with the remaining liquid being Furan-PYR$_{14}$Cl.

With reference to FIG. 4/Table 4, the synthesis of Furoyl-PYR$_{11}$Cl:
1) NMPD is purified by distillation at 85° C.
2) NMPD and 2-Furoyl chloride are mixed at the mole ratio of 1:1.1.
3) Adding acetone of the same volume as the 2-Furoyl chloride.
4) Mix and stir at 70° C. for 12 hours.
5) Acetone is distilled off with the remaining liquid being Furoyl-PYR$_{11}$Cl.

With reference to FIG. 4/Table 4, the synthesis of Benzenesulfonyl-PYR$_{11}$Cl:
1) NMPD is purified by distillation at 85° C.
2) NMPD and Benzenesulfonyl chloride are mixed at the mole ratio of 1:1.1.
3) Adding acetone of the same volume as the Benzenesulfonyl chloride.
4) Mix and stir at 70° C. for 12 hours.
5) Acetone is distilled off with the remaining liquid being Benzenesulfonyl-PYR$_{11}$Cl.

With reference to FIG. 4/Table 4, the synthesis of p-Toluenesulfonyl-PYR$_{11}$Cl:
1) NMPD is purified by distillation at 85° C.
2) NMPD and p-Toluenesulfonyl chloride are mixed at the mole ratio of 1:1.1.
3) Adding acetone of the same volume as the p-Toluenesulfonyl chloride.
4) Mix and stir at 70° C. for 12 hours.
5) Acetone is distilled off with the remaining liquid being p-Toluenesulfonyl-PYR$_{11}$Cl.

3. Replacing the cation $X_1$ with other heterocyclic aromatic or amine such as imidazolium, quaternary ammonium, piperidinium, pyrrolidinium, morpholinium, triethylamine etc. Taking the synthesis of 1-(2-Furoyl)-1-methyl piperidinium chloride (Furoyl-PIP$_{11}$Cl) as an example. Firstly, N-methyl piperidine (MPIP) is purified by vacuum distillation, and then the MPIP and 2-Furoyl chloride are mixed at a mole ratio of 1:1.1. Acetone, same volume as 2-furoyl chloride, is added. It is mixed and stirred at 70° C. for 12 hours. Acetone is distilled off with the remaining liquid as Furoyl-PIP$_{11}$Cl. The synthesis parameters of other series of aromatic bonded to cation halide ionic liquids are shown in FIG. 5/Table 5.

With reference to FIG. 5/Table 5, the synthesis of Benzyl-PYR$_{IEE}$Cl:
1) NMPD is purified by distillation at 85° C.
2) NMPD and Benzyl 2-chloroethyl ether are mixed at a mole ratio of 1:1.1.
3) Acetone, same volume as Benzyl 2-chloroethyl ether, is added.
4) Mix and stir at 70° C. for 12 hours.
5) Acetone is distilled off with the remaining liquid as Benzyl-PYR$_{IEE}$Cl.

With reference to FIG. 5/Table 5, the synthesis of Furan-PYR$_{14}$Cl:
1) NMPD is purified by distillation at 85° C.
2) NMPD and 2-(4-chlorobutyl)furan are mixed at a mole ratio of 1:1.1.
3) Acetone, same volume as 2-(4-chlorobutyl)furan, is added.
4) Mix and stir at 70° C. for 12 hours.
5) Acetone is distilled off with the remaining liquid as Furan-PYR$_{14}$Cl.

With reference to FIG. 5/Table 5, the synthesis of Furoyl-PYR$_{11}$Cl:
1) NMPD is purified by distillation at 85° C.
2) NMPD and 2-Furoyl chloride are mixed at a mole ratio of 1:1.1.
3) Acetone, same volume as 2-Furoyl chloride, is added.
4) Mix and stir at 70° C. for 12 hours.
5) Acetone is distilled off with the remaining liquid as Furoyl-PYR$_{11}$Cl.

With reference to FIG. 5/Table 5, the synthesis of Benzyl-PIP$_{IEE}$Cl:
1) MPIP is purified by vacuum distillation.
2) MPIP and Benzyl 2-chloroethyl ether are mixed at a mole ratio of 1:1.1.
3) Acetone, same volume as Benzyl 2-chloroethyl ether, is added.
4) Mix and stir at 70° C. for 12 hours.
5) Acetone is distilled off with the remaining liquid as Benzyl-PIP$_{IEE}$Cl.

With reference to FIG. 5/Table 5, the synthesis of Furan-PIP$_{14}$Cl:

1) MPIP is purified by vacuum distillation.
2) MPIP and 2-(4-chlorobutyl)furan are mixed at a mole ratio of 1:1.1.
3) Acetone, same volume as 2-(4-chlorobutyl)furan, is added.
4) Mix and stir at 70° C. for 12 hours.
5) Acetone is distilled off with the remaining liquid as Furan-PIP$_{14}$Cl.

With reference to FIG. 5/Table 5, the synthesis of Furoyl-PIP$_{11}$Cl:
1) MPIP is purified by vacuum distillation.
2) MPIP and 2-Furoyl chloride are mixed at a mole ratio of 1:1.1.
3) Acetone, same volume as 2-Furoyl chloride, is added.
4) Mix and stir at 70° C. for 12 hours.
5) Acetone is distilled off with the remaining liquid as Furoyl-PIP$_{11}$Cl.

With reference to FIG. 5/Table 5, the synthesis of Benzyl-TEA$_{IEE}$Cl:
1) TEA is purified by vacuum distillation.
2) TEA and Benzyl 2-chloroethyl ether are mixed at a mole ratio of 1:1.1.
3) Acetone, same volume as Benzyl 2-chloroethyl ether, is added.
4) Mix and stir at 70° C. for 12 hours.
5) Acetone is distilled off with the remaining liquid as Benzyl-TEA$_{IEE}$Cl.

With reference to FIG. 5/Table 5, the synthesis of Furan-TEA$_{14}$Cl:
1) TEA is purified by vacuum distillation.
2) TEA and 2-(4-chlorobutyl)furan are mixed at a mole ratio of 1:1.1.
3) Acetone, same volume as 2-(4-chlorobutyl)furan, is added.
4) Mix and stir at 70° C. for 12 hours.
5) Acetone is distilled off with the remaining liquid as Furan-TEA$_{14}$Cl.

With reference to FIG. 5/Table 5, the synthesis of Furoyl-TEA$_{11}$Cl:
1) TEA is purified by vacuum distillation.
2) TEA and 2-Furoyl chloride are mixed at a mole ratio of 1:1.1.
3) Acetone, same volume as 2-Furoyl chloride, is added.
4) Mix and stir at 70° C. for 12 hours.
5) Acetone is distilled off with the remaining liquid as Furoyl-PIP$_{11}$Cl.

With reference to FIG. 5/Table 5, the synthesis of Benzyl-MIM$_{IEE}$Cl:
1) MIM is purified by vacuum distillation.
2) MIM and Benzyl 2-chloroethyl ether are mixed at a mole ratio of 1:1.1.
3) Acetone, same volume as Benzyl 2-chloroethyl ether, is added.
4) Mix and stir at 25° C. for 12 hours.
5) Acetone is distilled off with the remaining liquid as Benzyl-PYR$_{IEE}$Cl.

With reference to FIG. 5/Table 5, the synthesis of Furan-MIM$_{14}$Cl:
1) MIM is purified by vacuum distillation.
2) MIM and 2-(4-chlorobutyl)furan mixed at a mole ratio of 1:1.1.
3) Acetone, same volume as 2-(4-chlorobutyl)furan, is added.
4) Mix and stir at 25° C. for 12 hours.
5) Acetone is distilled off with the remaining liquid as Furan-MIM$_{14}$Cl.

With reference to FIG. 5/Table 5, the synthesis of Furoyl-MIM$_{11}$Cl:
1) MIM is purified by vacuum distillation.
2) MIM and 2-Furoyl chloride are mixed at a mole ratio of 1:1.1.
3) Acetone, same volume as 2-Furoyl chloride, is added.
4) Mix and stir at 25° C. for 12 hours.
5) Acetone is distilled off with the remaining liquid as Furoyl-MIM$_{11}$Cl.

With reference to FIG. 5/Table 5, the synthesis of Furoyl-MPE$_{11}$Cl:
1) MPE is purified by vacuum distillation.
2) MPE and 2-Furoyl chloride are mixed at a mole ratio of 1:1.1.
3) Acetone, same volume as 2-Furoyl chloride, is added.
4) Mix and stir at 45° C. for 12 hours.
5) Acetone is distilled off with the remaining liquid as Furoyl-MPE$_{11}$Cl.

With reference to FIG. 5/Table 5, the synthesis of Furoyl-PYO$_{11}$Cl:
1) PYO is purified by vacuum distillation.
2) PYO and 2-Furoyl chloride are mixed at a mole ratio of 1:1.1.
3) Acetone, same volume as 2-Furoyl chloride, is added.
4) Mix and stir at 45° C. for 12 hours.
5) Acetone is distilled off with the remaining liquid as Furoyl-PYO$_{11}$Cl.

Step 2. Synthesis of Ionic Liquid with Aromatic Group Bonded to Cation

1. Taking the synthesis of 1-(2-Furoyl)-1-methyl pyrrolidinium hexafluorophosphate (Furoyl-PYR$_{11}$PF$_6$) as an example. 1-(2-furoyl)-1-methyl pyrrolidinium chloride (Furoyl-PYR$_{11}$Cl) synthesized in Step 1 is added to an equal weight of acetone (as a mixed solvent) followed by adding a same mole number of potassium hexafluorophosphate. It is stirred at 70° C. for 12 hours. After the white precipitate potassium chloride KCl is filtered, the remaining liquid is distilled under reduced pressure to remove the acetone, and then recrystallized to form Furoyl-PYR$_{11}$PF$_6$. Finally, the synthesized product is filtered, purified, and dried in a vacuum oven at 60° C. until its water content is less than 20 ppm. The synthesis parameters of other series of aromatic bonded to cation ionic liquid are shown in FIG. 6A, FIG. 6B or Table 6.

2. Replacing the cation X$_1$ with other heterocyclic aromatic or amine, such as imidazolium, quaternary ammonium, piperidinium, pyrrolidinium, morpholinium, triethylamine etc. Taking the synthesis of 1-(2-Furoyl)-1-methyl piperidinium hexafluorophosphate (Furoyl-PIP$_{11}$PF$_6$) as an example. 1-(2-furoyl)-1-methyl piperidinium chloride (Furoyl-PIP$_{11}$Cl) synthesized in Step 1 is added to an equal weight of acetone (as a mixed solvent) followed by the same mole number of potassium hexafluorophosphate. It is stirred at 70° C. for 12 hours. The white precipitate potassium chloride KCl is filtered out. The remaining liquid is distilled under reduced pressure to remove acetone, and then recrystallized to form Furoyl-PIP$_{11}$PF$_6$. Finally, the synthesized product is filtered, purified and dried in a vacuum oven at 60° C. until a water content of less than 20 ppm. The synthesis parameters of other series of aromatic bonded to cation ionic liquid are shown in FIG. 6A, FIG. 6B or Table 6.

3. Replacing anion Z$_1$ such as PF$_6^-$ (hexafluorophosphate), POF$_2^-$ (difluorophosphate), BF$_4^-$ (tetrafluoroborate), B(C$_2$O$_4$)$_2^-$ (BOB$^-$, bis(oxalato) borate), BF$_2$(C$_2$O$_4$)$^-$ (ODFB$^-$, difluoro(oxalato)borate), CF$_3$BF$_3^-$(trifluoromethyltrifluoroborate), (FSO$_2$)$_2$N$^-$ (FSI$^-$, bis(fluorosulfonyl)imide), $(CF_3SO_2)_2N^-$ (TFSI$^-$, bis(trifluoromethane) sulfonamide), $CH_3SO_4^-$ (MeSO$_4^-$, methyl sulfate), etc. Taking the synthesis of 1-(2-Furoyl)-1-methyl pyrrolidinium tetrafluoroborate (Furoyl-PYR$_{11}$BF$_4$) as an example. 1-(2-furoyl)-1-methyl pyrrolidinium chloride (Furoyl-PYR$_{11}$Cl) synthesized in Step 1 is added to the same weight of acetone (as a mixed solvent). The same mole number of potassium tetrafluoroborate is added. It is stirred at 70° C. for 12 hours. The white precipitate potassium chloride KCl is filtered. The remaining liquid is distilled under reduced pressure to remove acetone, and then recrystallized to form Furoyl-PYR$_{11}$BF$_4$. Finally, the synthesized product is filtered purified and dried in a vacuum oven at 60° C. until its water content is below 20 ppm. The synthesis parameters of other series of aromatic bonded to cation ionic liquid are shown in FIG. 6/Table 6.

With reference to FIG. 6A/Table 6, the synthesis of Benzyl-PYR$_{IEE}$PF$_6$:
1) Benzyl-PYR$_{IEE}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Benzyl-PYR$_{IEE}$PF$_6$.
7) The product is filtered, purified, and dried in a vacuum oven at 60° C. until its water content is less than 20 ppm.

With reference to FIG. 6A or Table 6, the synthesis of Benzyl-PYR$_{IBE}$PF$_6$:
1) Benzyl-PYR$_{IBE}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Benzyl-PYR$_{IBE}$PF$_6$.
7) The product is filtered, purified, and dried in a vacuum oven at 60° C. until its water content is less than 20 ppm.

With reference to FIG. 6A or Table 6, the synthesis of Benzoyl-PYR$_{11}$PF$_6$:
1) Benzoyl-PYR$_{11}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Benzoyl-PYR$_{11}$PF$_6$.
7) The product is filtered, purified, and dried in a vacuum oven at 60° C. until its water content is less than 20 ppm.

With reference to FIG. 6A or table 6, the synthesis of Phenacyl-PYR$_{11}$PF$_6$:
1) Phenacyl-PYR$_{11}$ in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Phenacyl-PYR$_{11}$PF$_6$.
7) The product is filtered, purified, and dried in a vacuum oven at 60° C. until its water content is less than 20 ppm.

With reference to FIG. 6A/Table 6, the synthesis of Furan-PYR$_{11}$PF$_6$:
1) Furan-PYR$_{11}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Furan-PYR$_{11}$PF$_6$.
7) The product is filtered, purified, and dried in a vacuum oven at 60° C. until its water content is less than 20 ppm.

With reference to FIG. 6A/Table 6, the synthesis of Furan-PYR$_{14}$PF$_6$:
1) Furan-PYR$_{14}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Furan-PYR$_{14}$PF$_6$.
7) The product is filtered, purified, and dried in a vacuum oven at 60° C. until its water content is less than 20 ppm.

With reference to FIG. 6A/Table 6, the synthesis of Furoyl-PYR$_{11}$PF$_6$:
1) Furoyl-PYR$_{11}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Furoyl-PYR$_{11}$PF$_6$
7) The product is filtered, purified, and dried in a vacuum oven at 60° C. until its water content is less than 20 ppm.

With reference to FIG. 6A/Table 6, the synthesis of Benzenesulfonyl-PYR$_{11}$PF$_6$:
1) Benzenesulfonyl-PYR$_{11}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Benzenesulfonyl-PYR$_{11}$PF$_6$.
7) The product is filtered, purified, and dried in a vacuum oven at 60° C. until its water content is less than 20 ppm.

With reference to FIG. 6A/Table 6, the synthesis of p-Toluenesulfonyl-PYR$_{11}$PF$_6$:
1) p-Toluenesulfonyl-PYR$_{11}$Cl in Step 1 is added to an equal weight of acetone.

2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form p-Toluenesulfonyl-$PYR_{11}PF_6$.
7) The product is filtered, purified, and dried in a vacuum oven at 60° C. until its water content is less than 20 ppm.

With reference to FIG. 6A/Table 6, the synthesis of Benzyl-$PIP_{IEE}PF_6$:
1) Benzyl-$PIP_{IEE}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Benzyl-$PIP_{IEE}PF_6$.
7) The product is filtered, purified, and dried in a vacuum oven at 60° C. until its water content is less than 20 ppm.

With reference to FIG. 6A/Table 6, the synthesis of Furan-$PIP_{14}PF_6$:
1) Furan-$PIP_{14}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Furan-$PIP_{14}PF_6$.
7) The product is filtered, purified, and dried in a vacuum oven at 60° C. until its water content is less than 20 ppm.

With reference to FIG. 6A/Table 6, the synthesis of Furoyl-$PIP_{11}PF_6$:
1) Furoyl-$PIP_{11}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone
6) Recrystallized to form Furoyl-PIP $11PF_6$.
7) The product is filtered, purified, and dried in a vacuum oven at 60° C. until its water content is less than 20 ppm.

With reference to FIG. 6A/Table 6, the synthesis of Benzyl-$TEA_{IEE}PF_6$:
1) Benzyl-$TEA_{IEE}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Benzyl-$TEA_{IEE}PF_6$.
7) The product is filtered, purified, and dried in a vacuum oven at 60° C. until its water content is less than 20 ppm.

With reference to FIG. 6A/Table 6, the synthesis of Furan-$TEA_{14}PF_6$:
1) Furan-$TEA_{14}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone.
6) Recrystallized to form Furan-$TEA_{14}PF_6$.
7) The product is filtered, purified, and dried in a vacuum oven at 60° C. until its water content is less than 20 ppm With reference to FIG. 6A/Table 6, the synthesis of Furoyl-$TEA_{11}PF_6$:
1) Furoyl-$TEA_{11}$Cl in Step 1 is added to an equal weight of acetone.
2) Same mole number of potassium hexafluorophosphate is added.
3) Stir at 70° C. for 12 hours.
4) White precipitate potassium chloride KCl is filtered.
5) Remaining liquid is distilled under reduced pressure to remove the acetone
6) Recrystallized to form Furoyl-$TEA_{11}PF_6$.
7) The product is filtered, purified, and dried in a vacuum oven at 60° C. until its water content is less than 20 ppm With reference to FIG. 6A/Table 6, the synthesis of Benzyl-$MIM_{IEE}PF_6$:
1) Benzyl-$MIM_{IEE}$Cl in Step 1 is added to an equal weight of acetone.
2) Same mole number of potassium hexafluorophosphate is added.
3) Stir at 25° C. for 12 hours.
4) White precipitate potassium chloride KCl is filtered.
5) Remaining liquid is distilled under reduced pressure to remove the acetone.
6) Recrystallized to form Benzyl-$MIM_{IEE}PF_6$.
7) The product is filtered, purified, and dried in a vacuum oven at 60° C. until its water content is less than 20 ppm.

With reference to FIG. 6A/Table 6, the synthesis of Furan-$MIM_{14}PF_6$:
1) Furan-$MIM_{14}$Cl in Step 1 is added to an equal weight of acetone.
2) Same mole number of potassium hexafluorophosphate is added.
3) Stir at 25° C. for 12 hours.
4) White precipitate potassium chloride KCl is filtered.
5) Remaining liquid is distilled under reduced pressure to remove the acetone.
6) Recrystallized to form Furan-$MIM_{14}PF_6$
7) The product is filtered, purified, and dried in a vacuum oven at 60° C. until its water content is less than 20 ppm.

With reference to FIG. 6A/Table 6, the synthesis of Furoyl-$MIM_{11}PF_6$:
1) Furoyl-$MIM_{11}$Cl in Step 1 is added to an equal weight of acetone.
2) Same mole number of potassium hexafluorophosphate is added.
3) Stir at 25° C. for 12 hours.
4) White precipitate potassium chloride KCl is filtered.
5) Remaining liquid is distilled under reduced pressure to remove the acetone.
6) Recrystallized to form Furoyl-$MIM_{11}PF_6$
7) The product is filtered, purified, and dried in a vacuum oven at 60° C. until its water content is less than 20 ppm With reference to FIG. 6B/Table 6, the synthesis of Furoyl-MPE$_{11}$PF$_6$:
1) Furoyl-MPE$_{11}$Cl in Step 1 is added to an equal weight of acetone.
2) Same mole number of potassium hexafluorophosphate is added.
3) Stir at 45° C. for 12 hours.
4) White precipitate potassium chloride KCl is filtered.
5) Remaining liquid is distilled under reduced pressure to remove the acetone.
6) Recrystallized to form Furoyl-MPE$_{11}$PF$_6$.
7) The product is filtered, purified, and dried in a vacuum oven at 60° C. until its water content is less than 20 ppm.

With reference to FIG. 6B/Table 6, the synthesis of Furoyl-PYO$_{11}$PF$_6$.
1) Furoyl-PYO$_{11}$Cl in Step 1 is added to an equal weight of acetone.
2) Same mole number of potassium hexafluorophosphate is added.
3) Stir at 45° C. for 12 hours.
4) White precipitate potassium chloride KCl is filtered.
5) Remaining liquid is distilled under reduced pressure to remove the acetone.
6) Recrystallized to form Furoyl-PYO$_{11}$PF$_6$.
7) The product is filtered, purified, and dried in a vacuum oven at 60° C. until its water content is less than 20 ppm.

With reference to FIG. 6B/Table 6, the synthesis of Furoyl-PYR$_{11}$BF$_4$:
1) Furoyl-PYR$_{11}$Cl in Step 1 is added to an equal weight of acetone.
2) Same mole number of potassium tetrafluoroborate is added.
3) Stir at 70° C. for 12 hours.
4) White precipitate potassium chloride KCl is filtered.
5) Remaining liquid is distilled under reduced pressure to remove the acetone.
6) Recrystallized to form Furoyl-PYR$_{11}$BF$_4$.
7) The product is filtered, purified, and dried in a vacuum oven at 60° C. until its water content is less than 20 ppm.

With reference to FIG. 6B/Table 6, the synthesis of Furoyl-PYR$_{11}$FSI.
1) Furoyl-PYR$_{11}$Cl in Step 1 is added to an equal weight of acetone.
2) Same mole number of lithiumbis(fluorosulfonyl)imide is added.
3) Stir at 70° C. for 12 hours.
4) White precipitate lithium chloride LiCl is filtered.
5) Remaining liquid is distilled under reduced pressure to remove the acetone.
6) Recrystallized to form Furoyl-PYR$_{11}$FSI.
7) The product is filtered, purified, and dried in a vacuum oven at 60° C. until its water content is less than 20 ppm.

With reference to FIG. 6B/Table 6, the synthesis of Furoyl-PYR$_{11}$TFSI.
1) Furoyl-PYR$_{11}$Cl in Step 1 is added to an equal weight of acetone.
2) Same mole number of lithium bis(trifluoromethane) sulfonamide is added.
3) Stir at 70° C. for 12 hours.
4) White precipitate lithium chloride LiCl is filtered.
5) Remaining liquid is distilled under reduced pressure to remove the acetone.
6) Recrystallized to form Furoyl-PYR$_{11}$TFSI.
7) The product is filtered, purified, and dried in a vacuum oven at 60° C. until its water content is less than 20 ppm.

With reference to FIG. 6B/Table 6, the synthesis of Furoyl-PYR$_{11}$CF$_3$BF$_3$.
1) Furoyl-PYR$_{11}$Cl in Step 1 is added to an equal weight of acetone.
2) Same mole number of lithium trifluoromethyltrifluoroborate is added.
3) Stir at 70° C. for 12 hours.
4) White precipitate lithium chloride LiCl is filtered.
5) Remaining liquid is distilled under reduced pressure to remove the acetone.
6) Recrystallized to form Furoyl-PYR$_{11}$CF$_3$BF$_3$.
7) The product is filtered, purified, and dried in a vacuum oven at 60° C. until its water content is less than 20 ppm.

With reference to FIG. 6B/Table 6, the synthesis of Furoyl-PYR$_{11}$POF$_2$:
1) Furoyl-PYR$_{11}$Cl in Step 1 is added to an equal weight of acetone.
2) Same mole number of lithium difluorophosphate is added.
3) Stir at 70° C. for 12 hours.
4) White precipitate lithium chloride LiCl is filtered.
5) Remaining liquid is distilled under reduced pressure to remove the acetone.
6) Recrystallized to form Furoyl-PYR$_{11}$POF$_2$.
7) The product is filtered, purified, and dried in a vacuum oven at 60° C. until its water content is less than 20 ppm.

With reference to FIG. 6B/Table 6, the synthesis of Furoyl-PYR$_{11}$MeSO$_4$:
1) Furoyl-PYR$_{11}$Cl in Step 1 is added to an equal weight of acetone.
2) Same mole number of potassium methyl sulfate is added.
3) Stir at 70° C. for 12 hours.
4) White precipitate potassium chloride KCl is filtered.
5) Remaining liquid is distilled under reduced pressure to remove the acetone.
6) Recrystallized to form Furoyl-PYR$_{11}$MeSO$_4$:
The product is filtered, purified, and dried in a vacuum oven at 60° C. until its water content is less than 20 ppm Embodiment 3

Figure 7B:
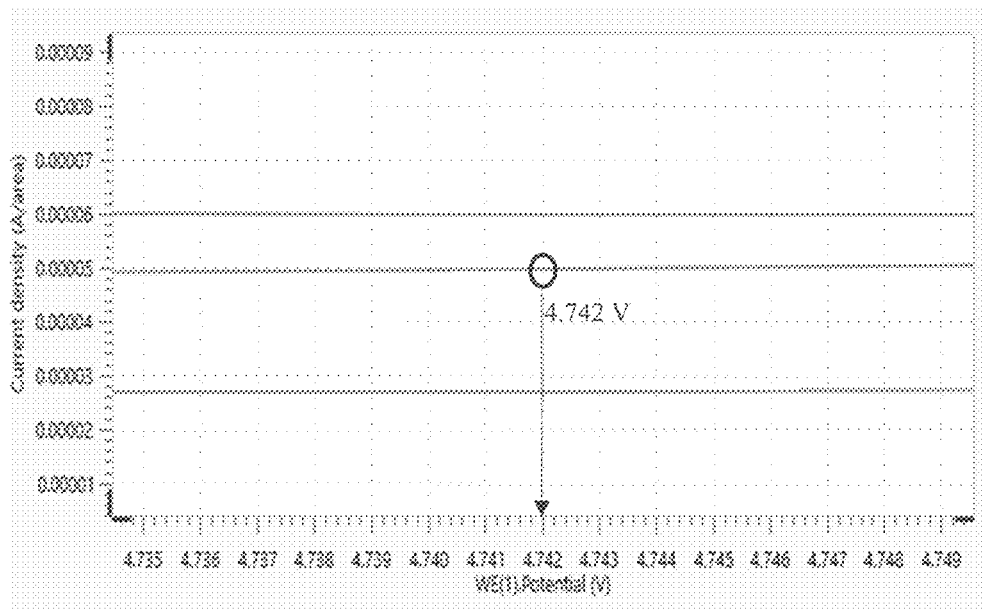
FIG. 7B is a graph showing the circled part in FIG. 7A in a different scale.

According to the maximum solubility, an ionic liquid with the two-core cationic chain or an ionic liquid with aromatic bonded to cation is added to a non-aqueous electrolyte. The amount of ionic liquid is about 10-15 wt. % of the electrolyte. Then, a linear sweep voltammetry (LSV) is conducted using the AutoLab 302N electrochemistry to obtain the maximum oxidation potential of the electrolyte.
Testing Conditions of LSV:
working electrode Pt, reference electrode Li, counter electrode Li, scan voltage range 0.5~5.0 V, scan rate 0.03 V/s.
1. Traditional ionic liquid with aromatic heterocycle: 1-propyl-1-methylpyrrolidium hexafluorophosphate (PYR$_{13}$PF$_6$)
Electrolyte: 1M LiPF$_6$+EC:DMC:EMC=1:1:1 (vol.)+1 wt. % VC+15 wt. % PYR$_{13}$PF$_6$
With reference to FIGS. 7A and 7B, the LSV test shows that the lithium deposition/dissolution reaction at low potential. A corrosion current greater than $5 \times 10^{-5}$ (Amp.) occurred at the high potential of 4.742V in the first cycle. That is an oxidation reaction, which means that the maximum oxidation potential of the organic electrolyte with adding 15 wt. % $PYR_{13}PF_6$ is 4.742 V. The potential window of that is about 0-4.742 V. There is no side reaction in this electrolyte within this working voltage range.

2. Two-core cationic chain ionic liquid: 1,5 bis(1-methylpyrrolidium 1-yl) pentane dihexafluorophosphate [$DiPYR_{15}(PF_6)_2$], 1,8 bis(1-methylpyrrolidium 1-yl) octane dihexafluorophosphate [$DiPYR_{18}(PF_6)_2$]

Figure 8A:
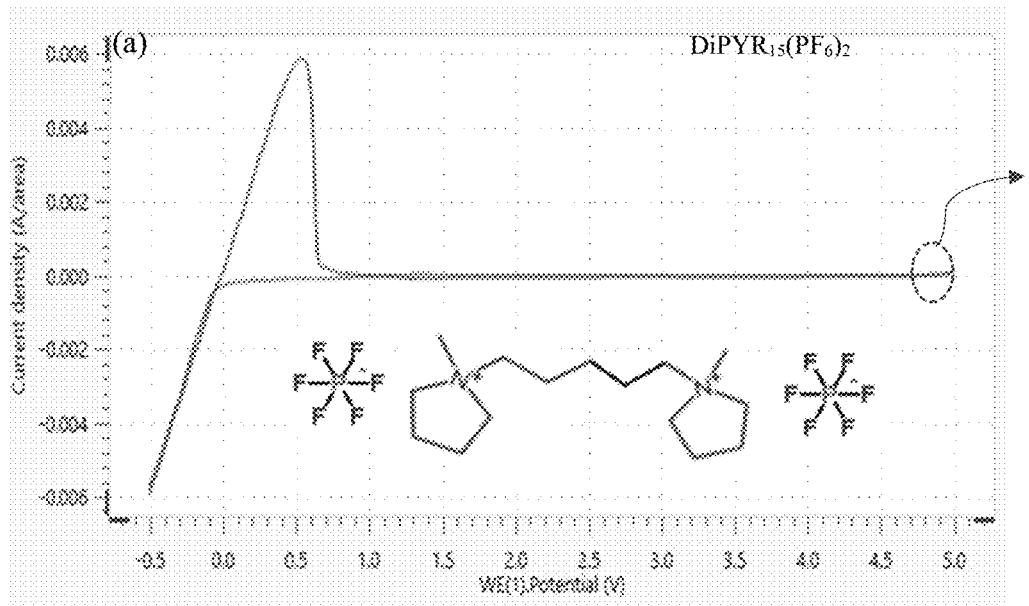
FIG. 8A is a graph showing results of a linear sweep voltammetry LSV of $DiPYR_{15}(PF_6)_2$.
Figure 8B:
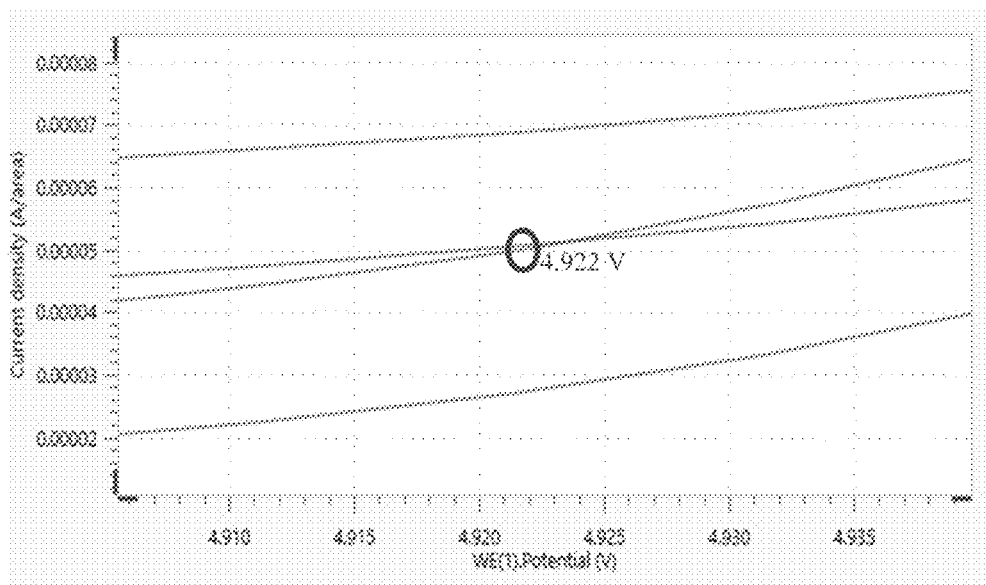
FIG. 8B is a graph showing the reading of the circled part in FIG. 8A.

Electrolyte:
  (a) 1M $LiPF_6$+EC:DMC:EMC=1:1:1 (vol.)+1 wt. % VC+10 wt. % $DiPYR_{15}(PF_6)_2$,
  (b) 1M $LiPF_6$+EC:DMC:EMC=1:1:1 (vol.)+1 wt. % VC+10 wt. % $DiPYR_{18}(PF_6)_2$ With reference to FIGS. 8A and 8B, the LSV test showed that the lithium deposition/dissolution reaction also occurs at low potential. The corrosion current greater than $5 \times 10^{-5}$ (Amp.) occurred at the high potential of 4.922V in the first cycle. This means that the maximum oxidation potential of the organic electrolyte with 10 wt. % $DiPYR_{15}(PF_6)_2$ added is 4.922V. The potential window is about 0-4.922 V which indicates that the addition of $DiPYR_{15}(PF_6)_2$ can increase the maximum oxidation potential of the electrolyte, reduces the dissociation reaction under the high working voltage, and inhibits the growth of internal impedance in the lithium-ion battery.

Figure 9A:
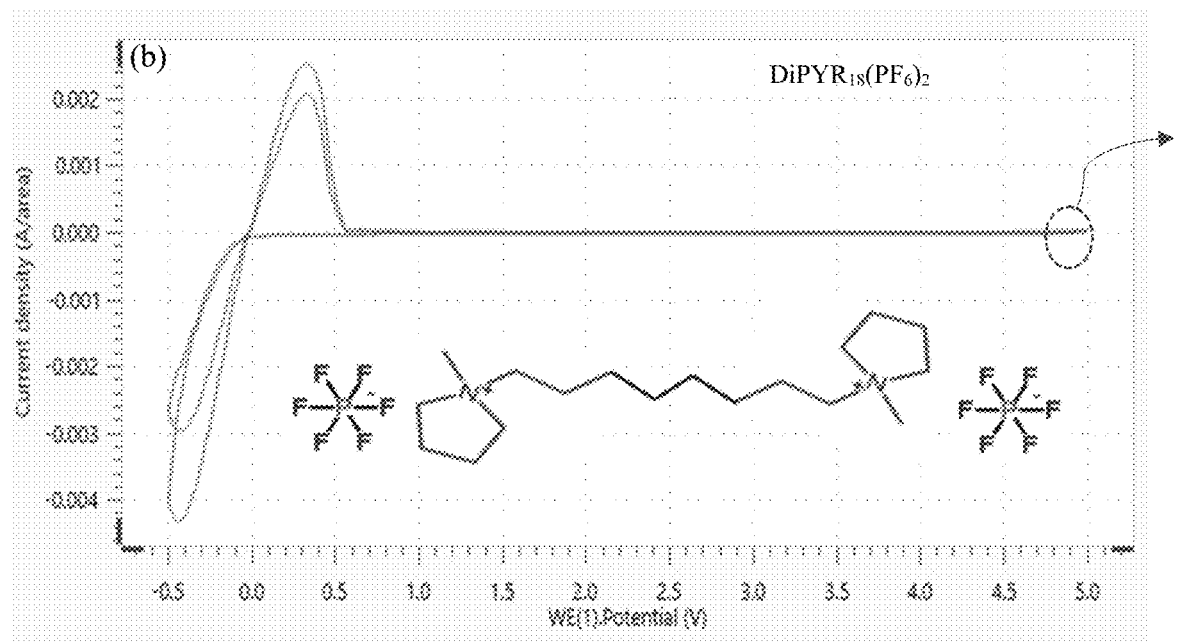
FIG. 9A is a graph showing results of a linear sweep voltammetry LSV of $DiPYR_{18}(PF_6)_2$.
Figure 9B:
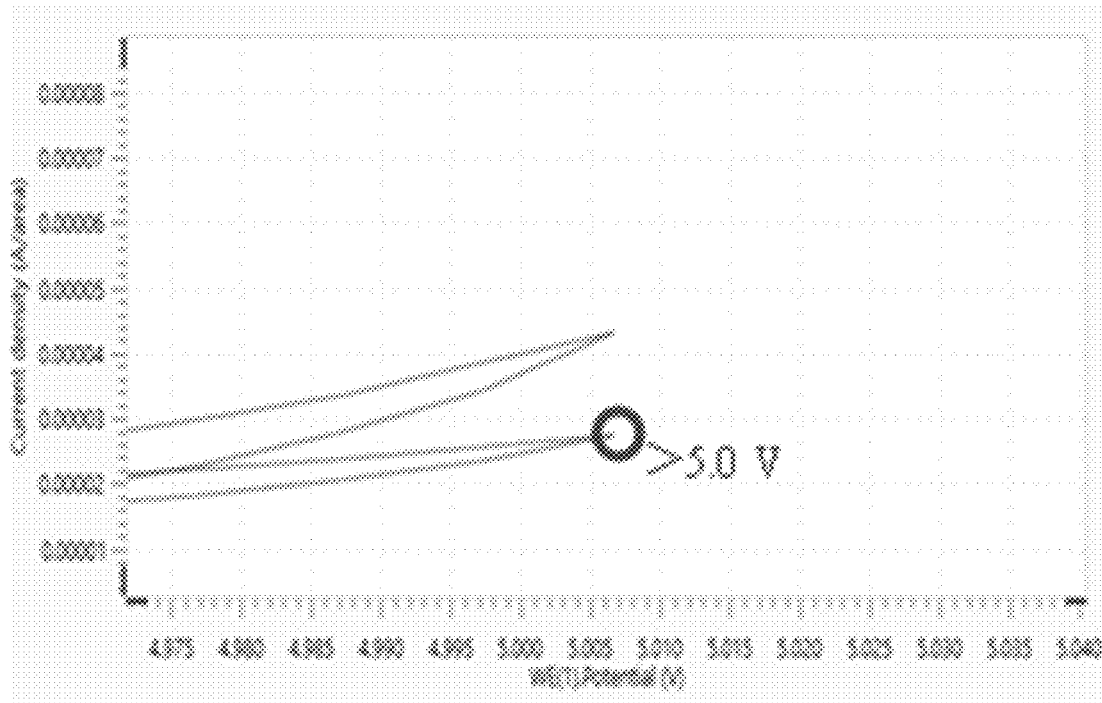
FIG. 9B is a graph showing the reading of the circled part in FIG. 9A.

With reference to FIGS. 9A and 9B, the LSV test shows that there was no corrosion current greater than $5 \times 10^{-5}$ (Amp.) at a high voltage of 5.02 V in the first cycle. This means that the maximum oxidation potential of organic electrolyte with adding 10 wt. % $DiPYR_{18}(PF_6)_2$ is greater than 5.0V. It indicates that the addition of $DiPYR_{18}(PF_6)_2$ can increase the maximum oxidation potential of the electrolyte with the ability of withstanding high voltage being better than that of the addition of $DiPYR_{15}(PF_6)_2$.

4. Replacing the alkyl chain Y with other functional groups, replacing the cation $X_1$ and $X_2$ with other heterocyclic aromatic or amine, or replacing the anion $Z_1$ and $Z_2$. Taking the following ionic liquids with two-core cationic chain as examples: bis [2-(1-methylpyrrolidinium 1-yl) ethyl] ether dihexafluorophosphate [$DiPYR_{IEE}(PF_6)_2$], 1,5-(1-methylpyrrolidium 1-yl)(1-methylpiperidinium) 1-yl) pentane dihexafluorophosphate [$PYRPIP_{15}(PF_6)_2$], 1,5-bis (1-methylpiperidinium 1-yl) pentane dihexafluorophosphate [$DiPIP_{15}(PF_6)_2$], 1,5-bis (1-methylpyrrolidium 1-yl) pentane (hexafluorophosphate) (tetrafluoroborate) [$DiPYR_{15}(PF_6)(BF_4)$], 1,5-(1-methylpyrrolidium 1-yl) (1-methyl-imidazolium-3-yl) pentane dihexafluorophosphate [$PYRMIM_{15}(PF_6)_2$].

Electrolyte:
  (a) 1M $LiPF_6$+EC:DMC:EMC=1:1:1 (vol.)+1 wt. % VC+15 wt. % $DiPYR_{IEE}(PF_6)_2$,
  (b) 1M $LiPF_6$+EC:DMC:EMC=1:1:1 (vol.)+1 wt. % VC+10 wt. % $PYRPIP_{15}(PF_6)_2$,
  (c) 1M $LiPF_6$+EC:DMC:EMC=1:1:1 (vol.)+1 wt. % VC+10 wt. % $DiPIP_{15}(PF_6)_2$,
  (d) 1M $LiPF_6$+EC:DMC:EMC=1:1:1 (vol.)+1 wt. % VC+15 wt. % $DiPYR_{15}(PF_6)(BF_4)$,
  (e) 1M $LiPF_6$+EC:DMC:EMC=1:1:1 (vol.)+1 wt. % VC+10 wt. % $PYRMIM_{15}(PF_6)_2$.

With reference to FIGS. 11A to 14B, the LSV test shows that the maximum oxidation potentials of the above four ionic liquids in the initial cycle are 4.774V, 4.929V, 4.895V and greater than 5.0V, respectively which indicates that the alkyl functional group Y, heterocyclic aromatic cation $X_1$ and $X_2$, and anion $Z_1$ and $Z_2$ can change the maximum oxidation potential of the electrolyte. Among them, the electrolyte with $DiPYR_{15}(PF_6)(BF_4)$ added has the best ability of withstanding high voltage. In addition, by replacing the cations $X_1$ and $X_2$ with methylimidazole (MIM) and morpholine (MPE) cations with result in extremely unstable electrolytes, and the highest oxidation potential of that cannot be determined. For the other types of ionic liquids with two-core cationic chain and the aromatic bonded to cation, the maximum oxidation potential of their electrolytes at the LSV test are shown in FIG. 15/Table 7 and FIG. 16/Table 8.

With reference to FIGS. 15A, 15B and 15C, the maximum oxidation potential must be greater than 4.7V to be considered to present an improvement. Any added amount of ionic liquid (as detailed below) would be of an amount of 10-15 wt. % in the organic electrolyte:

The maximum oxidation potential (V) of an organic electrolyte, 1M LiPF6+EC:DMC:EMC=1:1:1 (vol.)+1 wt. % VC, as a control sample is 4.652V.

The maximum oxidation potential (V) of $DiPYR_{14}(PF_6)_2$, $X_1$ is NMPD, $X_2$ is NMPD, Y is Butane, C4, $Z_1$ is $PF_6$, $Z_2$ is $PF_6$ is 4.906V.

The maximum oxidation potential (V) of $DiPYR_{15}(PF_6)_2$, $X_1$ is NMPD, $X_2$ is NMPD, Y is Pentane, C5, $Z_1$ is $PF_6$, $Z_2$ is $PF_6$ is 4.922V.

The maximum oxidation potential (V) of $DiPYR_{16}(PF_6)_2$, $X_1$ is NMPD, $X_2$ is NMPD, Y is Hexane, C6, $Z_1$ is $PF_6$, $Z_2$ is $PF_6$ is 4.872V.

The maximum oxidation potential (V) of $DiPYR_{18}(PF_6)_2$, $X_1$ is NMPD, $X_2$ is NMPD, Y is Octane, C8, $Z_1$ is $PF_6$, $Z_2$ is $PF_6$ is >5.0V.

The maximum oxidation potential (V) of $DiPIP_{15}(PF_6)_2$, $X_1$ is MPIP, $X_2$ is MPIP, Y is Pentane, C5, $Z_1$ is $PF_6$, $Z_2$ is $PF_6$ is 4.895V.

The maximum oxidation potential (V) of $DiPIP_{18}(PF_6)_2$, $X_1$ is MPIP, $X_2$ is MPIP, Y is Octane, C8, $Z_1$ is $PF_6$, $Z_2$ is $PF_6$ is 4.963V.

The maximum oxidation potential (V) of $DiPYR_{15}(PF_6)(BF_4)$, $X_1$ is NMPD, $X_2$ is NMPD, Y is Pentane, C5, $Z_1$ is $PF_6$, $Z_2$ is $BF_4$ is >5.0V.

The maximum oxidation potential (V) of $DiPYR_{15}(PF_6)(BF_4)$, $X_1$ is NMPD, $X_2$ is NMPD, Y is Octane, C8, $Z_1$ is $PF_6$, $Z_2$ is $BF_4$ is >5.0V.

The maximum oxidation potential (V) of $DiPIP_{15}(PF_6)(BF_4)$, $X_1$ is MPIP, $X_2$ is MPIP, Y is Pentane, C5, $Z_1$ is $PF_6$, $Z_2$ is $BF_4$ is 4.955V.

The maximum oxidation potential (V) of $DiPIP_{18}(PF_6)(BF_4)$, $X_1$ is MPIP, $X_2$ is MPIP, Y is Octane, C8, $Z_1$ is $PF_6$, $Z_2$ is $BF_4$ is >5.0V.

The maximum oxidation potential (V) of $PYRPIP_{15}(PF_6)_2$, $X_1$ is NMPD, $X_2$ is MPIP, Y is Pentane, C5, $Z_1$ is $PF_6$, $Z_2$ is $PF_6$ is 4.929V.

The maximum oxidation potential (V) of $PYRTEA_{15}(PF_6)_2$, $X_1$ is NMPD, $X_2$ is TEA, Y is Pentane, C5, $Z_1$ is $PF_6$, $Z_2$ is $PF_6$ is >5.0V.

The maximum oxidation potential (V) of $PYRMPE_{15}(PF_6)_2$, $X_1$ is NMPD, $X_2$ is MPE, Y is Pentane, C5, $Z_1$ is $PF_6$, $Z_2$ is $PF_6$ is 4.653V.

The maximum oxidation potential (V) of $PYRMIM_{15}(PF_6)_2$, $X_1$ is NMPD, $X_2$ is MIM, Y is Pentane, C5, $Z_1$ is $PF_6$, $Z_2$ is $PF_6$ is unavailable.

The maximum oxidation potential (V) of PYRPYO$_{15}$ (PF$_6$)$_2$, X$_1$ is NMPD, X$_2$ is PYO, Y is Pentane, C5, Z$_1$ is PF$_6$, Z$_2$ is PF$_6$ is 4.782V.

The maximum oxidation potential (V) of PIPTEA$_{15}$ (PF$_6$)$_2$, X$_1$ is MPIP, X$_2$ is TEA, Y is Pentane, C5, Z$_1$ is PF$_6$, Z$_2$ is PF$_6$ is 4.968V.

The maximum oxidation potential (V) of PIPMPE$_{15}$ (PF$_6$)$_2$, X$_1$ is MPIP, X$_2$ is MPE, Y is Pentane, C5, Z$_1$ is PF$_6$, Z$_2$ is PF$_6$ is 4.372V.

The maximum oxidation potential (V) of PIPMIM$_{15}$ (PF$_6$)$_2$, X$_1$ is MPIP, X$_2$ is MIM, Y is Pentane, C5, Z$_1$ is PF$_6$, Z$_2$ is PF$_6$ is unavailable.

The maximum oxidation potential (V) of PIPPYO$_{15}$ (PF$_6$)$_2$, X$_1$ is MPIP, X$_2$ is PYO, Y is Pentane, C5, Z$_1$ is PF$_6$, Z$_2$ is PF$_6$ is 4.739V.

The maximum oxidation potential (V) of TEAMPE$_{15}$ (PF$_6$)$_2$, X$_1$ is TEA, X$_2$ is MPE, Y is Pentane, C5, Z$_1$ is PF$_6$, Z$_2$ is PF$_6$ is 4.562V.

The maximum oxidation potential (V) of TEAMIM$_{15}$ (PF$_6$)$_2$ X$_1$ is TEA, X$_2$ is MIM, Y is Pentane, C5, Z$_1$ is PF$_6$, Z$_2$ is PF$_6$ is unavailable.

The maximum oxidation potential (V) of TEAPYO$_{15}$ (PF$_6$)$_2$, X$_1$ is TEA, X$_2$ is PYO, Y is Pentane, C5, Z$_1$ is PF$_6$, Z$_2$ is PF$_6$ is 4.809V.

The maximum oxidation potential (V) of MIMMPE$_{15}$ (PF$_6$)$_2$, X$_1$ is MIM, X$_2$ is MPE, Y is Pentane, C5, Z$_1$ is PF$_6$, Z$_2$ is PF$_6$ is unavailable.

The maximum oxidation potential (V) of MIMPYO$_{15}$ (PF$_6$)$_2$, X$_1$ is MIM, X$_2$ is PYO, Y is Pentane, C5, Z$_1$ is PF$_6$, Z$_2$ is PF$_6$ is unavailable.

The maximum oxidation potential (V) of PYRPIP$_{15}$ (PF$_6$)(PF$_4$), X$_1$ is NMPD, X$_2$ is MPIP, Y is Pentane, C5, Z$_1$ is PF$_6$, Z$_2$ is BF$_4$ is >5.0V.

The maximum oxidation potential (V) of PYRTEA$_{15}$ (PF$_6$)(PF$_4$), X$_1$ is NMPD, X$_2$ is TEA, Y is Pentane, C5, Z$_1$ is PF$_6$, Z$_2$ is BF$_4$ is >5.0V.

The maximum oxidation potential (V) of PYRPYO$_{15}$ (PF$_6$)(PF$_4$), X$_1$ is NMPD, X$_2$ is PYO, Y is Pentane, C5, Z$_1$ is PF$_6$, Z$_2$ is BF$_4$ is 4.833V.

The maximum oxidation potential (V) of PIPTEA$_{15}$ (PF$_6$)(PF$_4$), X$_1$ is MPIP, X$_2$ is TEA, Y is Pentane, C5, Z$_1$ is PF$_6$, Z$_2$ is BF$_4$ is 4.928V.

The maximum oxidation potential (V) of PIPPYO$_{15}$ (PF$_6$)(PF$_4$), X$_1$ is MPIP, X$_2$ is PYO, Y is Pentane, C5, Z$_1$ is PF$_6$, Z$_2$ is BF$_4$ is 4.760V.

The maximum oxidation potential (V) of TEAPYO$_{15}$ (PF$_6$)(PF$_4$), X$_1$ is TEA, X$_2$ is PYO, Y is Pentane, C5, Z$_1$ is PF$_6$, Z$_2$ is BF$_4$ is 4.858V.

The maximum oxidation potential (V) of DiPYR$_{15}$ (TFSI)(FSI), X$_1$ is NMPD, X$_2$ is NMPD, Y is Pentane, C5, Z$_1$ is TFSI, Z$_2$ is FSI is 4.937V.

The maximum oxidation potential (V) of DiPIP$_{15}$ (TFSI)(FSI), X$_1$ is MPIP, X$_2$ is MPIP, Y is Pentane, C5, Z$_1$ is TFSI, Z$_2$ is FSI is 4.912V.

The maximum oxidation potential (V) of PYRPIP$_{15}$ (TFSI)(FSI), X$_1$ is NMPD, X$_2$ is MPIP, Y is Pentane, C5, Z$_1$ is TFSI, Z$_2$ is FSI is 4.938V.

The maximum oxidation potential (V) of PYRTEA$_{15}$ (TFSI)(FSI), X$_1$ is NMPD, X$_2$ is TEA, Y is Pentane, C5, Z$_1$ is TFSI, Z$_2$ is FSI is >5.0V.

The maximum oxidation potential (V) of PIPTEA$_{15}$ (TFSI)(FSI), X$_1$ is MPIP, X$_2$ is TEA, Y is Pentane, C5, Z$_1$ is TFSI, Z$_2$ is FSI is 4.953V.

The maximum oxidation potential (V) of DiPYR$_{15}$ (CF$_3$BF$_3$)(POF$_2$), X$_1$ is NMPD, X$_2$ is NMPD, Y is Pentane, C5, Z$_1$ is CF$_3$BF$_3$, Z$_2$ is POF$_2$ is >5.0V.

The maximum oxidation potential (V) of DiPIP$_{15}$ (CF$_3$BF$_3$)(POF$_2$), X$_1$ is MPIP, X$_2$ is MPIP, Y is Pentane, C5, Z$_1$ is CF$_3$BF$_3$, Z$_2$ is POF$_2$ is 4.935V.

The maximum oxidation potential (V) of PYRPIP$_{15}$ (CF$_3$BF$_3$)(POF$_2$), X$_1$ is NMPD, X$_2$ is MPIP, Y is Pentane, C5, Z$_1$ is CF$_3$BF$_3$, Z$_2$ is POF$_2$ is >5.0V.

The maximum oxidation potential (V) of PYRTEA$_{15}$ (CF$_3$BF$_3$)(POF$_2$), X$_1$ is NMPD, X$_2$ is TEA, Y is Pentane, C5, Z$_1$ is CF$_3$BF$_3$, Z$_2$ is POF$_2$ is >5.0V.

The maximum oxidation potential (V) of PIPTEA$_{15}$ (CF$_3$BF$_3$)(POF$_2$), X$_1$ is MPIP, X$_2$ is TEA, Y is Pentane, C5, Z$_1$ is CF$_3$BF$_3$, Z$_2$ is POF$_2$ is 4.976V.

The maximum oxidation potential (V) of DiPYR$_{14}$ (BF$_4$)(FSI), X$_1$ is NMPD, X$_2$ is NMPD, Y is Pentane, C5, Z$_1$ is BF$_4$, Z$_2$ is FSI is 4.962V.

The maximum oxidation potential (V) of DiPIP$_{15}$(BF$_4$)(FSI), X$_1$ is MPIP, X$_2$ is MPIP, Y is Pentane, C5, Z$_1$ is BF$_4$, Z$_2$ is FSI is 4.907V.

The maximum oxidation potential (V) of PYRPIP$_{15}$ (BF$_4$)(FSI), X$_1$ is NMPD, X$_2$ is MPIP, Y is Pentane, C5, Z$_1$ is BF$_4$, Z$_2$ is FSI is >5.0V.

The maximum oxidation potential (V) of PYRTEA$_{15}$ (BF$_4$)(FSI), X$_1$ is NMPD, X$_2$ is TEA, Y is Pentane, C5, Z$_1$ is BF$_4$, Z$_2$ is FSI is >5.0V.

The maximum oxidation potential (V) of PIPTEA$_{15}$ (BF$_4$)(FSI), X$_1$ is MPIP, X$_2$ is TEA, Y is Pentane, C5, Z$_1$ is BF$_4$, Z$_2$ is FSI is 4.974V.

The maximum oxidation potential (V) of DiPYR$_{IEE}$ (PF$_6$)$_2$, X$_1$ is NMPD, X$_2$ is NMPD, Y is iethyl ether, Z$_1$ is PF$_6$, Z$_2$ is PF$_6$ is 4.774V.

The maximum oxidation potential (V) of DiPYR$_{IEC}$ (PF$_6$)$_2$, X$_1$ is NMPD, X$_2$ is NMPD, Y is Diethyl carbonate, C4, Z$_1$ is PF$_6$, Z$_2$ is PF$_6$ is 4.825V.

The maximum oxidation potential (V) of DiPYR$_{IPO}$ (PF$_6$)$_2$, X$_1$ is NMPD, X$_2$ is NMPD, Y is Pentan-3-one, Z$_1$ is PF$_6$, Z$_2$ is PF$_6$ is 4.833V.

The maximum oxidation potential (V) of DiPYR$_{IEB}$ (PF$_6$)$_2$, X$_1$ is NMPD, X$_2$ is NMPD, Y is Diethyl butanedioate, Z$_1$ is PF$_6$, Z$_2$ is PF$_6$ is 4.706V.

With reference to FIGS. 16A and 16B, again, the maximum oxidation potential must be greater than 4.7V to be considered to present an improvement. Any added amount of ionic liquid (as detailed below) would be of an amount of 1-10 wt. % in the organic electrolyte:

The maximum oxidation potential (V) of an organic electrolyte, 1M LiPF6+EC:DMC:EMC=1:1:1 (vol.)+1 wt. % VC, as a control sample is 4.652V.

The maximum oxidation potential (V) of PYR$_{1BEE}$PF$_6$ with X$_1$ is NMPD, Y & W are Benzyl ethyl ether, Z$_1$ is PF$_6$, is 4.739V.

The maximum oxidation potential (V) of PYR$_{1BBE}$PF$_6$ with X$_1$ is NMPD, Y & W are Benzyl butyl ether, Z$_1$ is PF$_6$, is 4.757V.

The maximum oxidation potential (V) of PYR$_{1BZO}$PF$_6$ with X$_1$ is NMPD, Y & W are Benzoyl, Z$_1$ is PF$_6$, is 4.746V.

The maximum oxidation potential (V) of PYR$_{1PHC}$PF$_6$ with X$_1$ is NMPD, Y & W are Phenacyl, Z$_1$ is PF$_6$, is 4.773V.

The maximum oxidation potential (V) of PYR$_{1FRA}$PF$_6$ with X$_1$ is NMPD, Y & W are 2-Furan, Z$_1$ is PF$_6$, is 4.722V.

The maximum oxidation potential (V) of PYR$_{14FRA}$PF$_6$ with X$_1$ is NMPD, Y & W are 2-ButylFuran, Z$_1$ is PF$_6$, is 4.736V.

The maximum oxidation potential (V) of $PYR_{1FRO}PF_6$ with $X_1$ is NMPD, Y & W are 2-Furoyl, $Z_1$ is $PF_6$, is 4.829V.

The maximum oxidation potential (V) of $PYR_{1BSF}PF_6$ with $X_1$ is NMPD, Y & W are Benzenesulfonyl, $Z_1$ is $PF_6$, is 4.817V.

The maximum oxidation potential (V) of $PYR_{1TSF}PF_6$ with $X_1$ is NMPD, Y & W are p-Toluenesulfonyl, $Z_1$ is $PF_6$, is 4.801V.

The maximum oxidation potential (V) of $PIP_{1BEE}PF_6$ with $X_1$ is MPIP, Y & W are Benzyl ethyl ether, $Z_1$ is $PF_6$, is 4.536V.

The maximum oxidation potential (V) of $PIP_{14FRA}PF_6$ with $X_1$ is MPIP, Y & W are 2-ButylFuran, $Z_1$ is $PF_6$, is 4.622V.

The maximum oxidation potential (V) of $PIP_{1FRO}PF_6$ with $X_1$ is MPIP, Y & W are 2-Furoyl, $Z_1$ is $PF_6$, is 4.729V.

The maximum oxidation potential (V) of $TEA_{1BEE}PF_6$ with $X_1$ is TEA, Y & W are Benzyl ethyl ether, $Z_1$ is $PF_6$, is 4.389V.

The maximum oxidation potential (V) of $TEA_{14FRA}PF_6$ with $X_1$ is TEA, Y & W are 2-ButylFuran, $Z_1$ is $PF_6$, is 4.443V.

The maximum oxidation potential (V) of $TEA_{1FRO}PF_6$ with $X_1$ is TEA, Y & W are 2-Furoyl, $Z_1$ is $PF_6$, is 4.738V.

The maximum oxidation potential (V) of $MIM_{1BEE}PF_6$ with $X_1$ is MIM, Y & W are Benzyl ethyl ether, $Z_1$ is $PF_6$, is unavailable.

The maximum oxidation potential (V) of $MIM_{14FRA}PF_6$ with $X_1$ is MIM, Y & W are 2-ButylFuran, $Z_1$ is $PF_6$, is unavailable.

The maximum oxidation potential (V) of $MIM_{14FRO}PF_6$ with $X_1$ is MIM, Y & W are 2-Furoyl, $Z_1$ is $PF_6$, is unavailable.

The maximum oxidation potential (V) of $MPE_{1FRO}PF_6$ with $X_1$ is MPE, Y & W are 2-Furoyl, $Z_1$ is $PF_6$, is unavailable.

The maximum oxidation potential (V) of $PYO_{1FRO}PF_6$ with $X_1$ is PYO, Y & W are 2-Furoyl, $Z_1$ is $PF_6$, is unavailable.

The maximum oxidation potential (V) of $PYO_{1FRO}BF_4$ with $X_1$ is NMPD, Y & W are 2-Furoyl, $Z_1$ is $BF_4$, is 4.926V.

The maximum oxidation potential (V) of $PYR_{1FRO}FSI$ with $X_1$ is NMPD, Y & W are 2-Furoyl, $Z_1$ is FSI, is 4.877V.

The maximum oxidation potential (V) of $PYR_{1FRO}TFSI$ with $X_1$ is NMPD, Y & W are 2-Furoyl, $Z_1$ is TFSI, is 4.917V.

The maximum oxidation potential (V) of $PYR_{1FRO}CF_3BF_3$ with $X_1$ is NMPD, Y & W are 2-Furoyl, $Z_1$ is $CF_3BF_3$, is 4.958V.

The maximum oxidation potential (V) of $PYR_{1FRO}POF_2$ with $X_1$ is NMPD, Y & W are 2-Furoyl, $Z_1$ is $POF_2$, is 4.923V.

The maximum oxidation potential (V) of $PYR_{1FRO}MeSO_4$ with $X_1$ is NMPD, Y & W are 2-Furoyl, $Z_1$ is $MeSO_4$, is 4.607V.

With reference to Tables 7 and 8, the LSV test shows that the highest oxidation potential of the related electrolyte cannot be determined, when the cation $X_1$ and $X_2$ of two-core cationic chain ionic liquid are methylimidazole (MIM) and morpholine (MPE) cations. There is no obvious improvement on the ability of withstanding high voltage. In addition, while the cation $X_1$ of ionic liquid with aromatic bonded to cation is the N-methyl pyrrolidine (NMPD), the maximum oxidation potential of related electrolyte is higher than 4.7 V, which shows an enhancement on the withstanding high voltage of electrolyte.

Embodiment 4

According to the maximum solubility, an ionic liquid with the two-core cationic chain or an ionic liquid with aromatic bonded to cation is added to a non-aqueous electrolyte. The amount of ionic liquid is about 10-15 wt. % of the electrolyte. Then, a cyclic voltammetry (CV) is conducted using the AutoLab 302N electrochemistry instrument to understand the oxidation-reduction reaction between the electrolyte and the graphite anode under different voltages.

CV Test Conditions:
Working electrode: (Anode material) meso carbon micro bead
MCMB:SuperP:CMC:SBR=95.5:1.0:1.5:2.0
Reference electrode Li, counter electrode Li, scan voltage range 0~2.5V, scan rate 1 mV/s.

Figure 17:
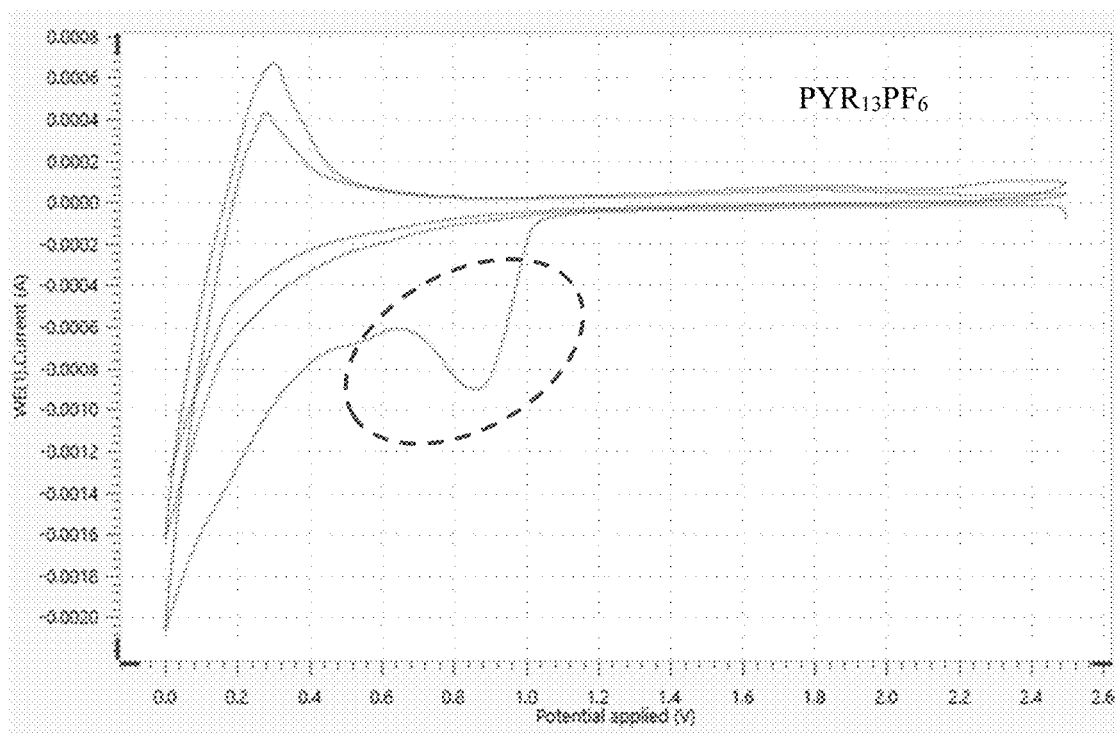
FIG. 17 is a graph showing results of a linear sweep voltammetry LSV of PYR$_{13}$PF$_6$.

1. Traditional cationic ionic liquid with aromatic heterocycle: 1-propyl-1-methylpyrrolidium hexafluorophosphate ($PYR_{13}PF_6$)
   Electrolyte: 1M $LiPF_6$+EC:DMC:EMC=1:1:1 (vol.)+1 wt. % VC+15 wt. % $PYR_{13}PF_6$
   With reference to FIG. 17, the CV test shows that a reduction peak appeared at 0.7-1.0 V when 15 wt. % $PYR_{13}PF_6$ ionic liquid was added to the electrolyte. The reason being that the $PYR_{13}^+$ cations are intercalated into the layered structure on the surface of MCMB, preventing lithium ions from migrating into the layered structure. This leads to the generation of lithium precipitation on the surface of anode, thereby increasing the interface impedance, and causing a decline in the cycle stability of battery.

Figure 18A:
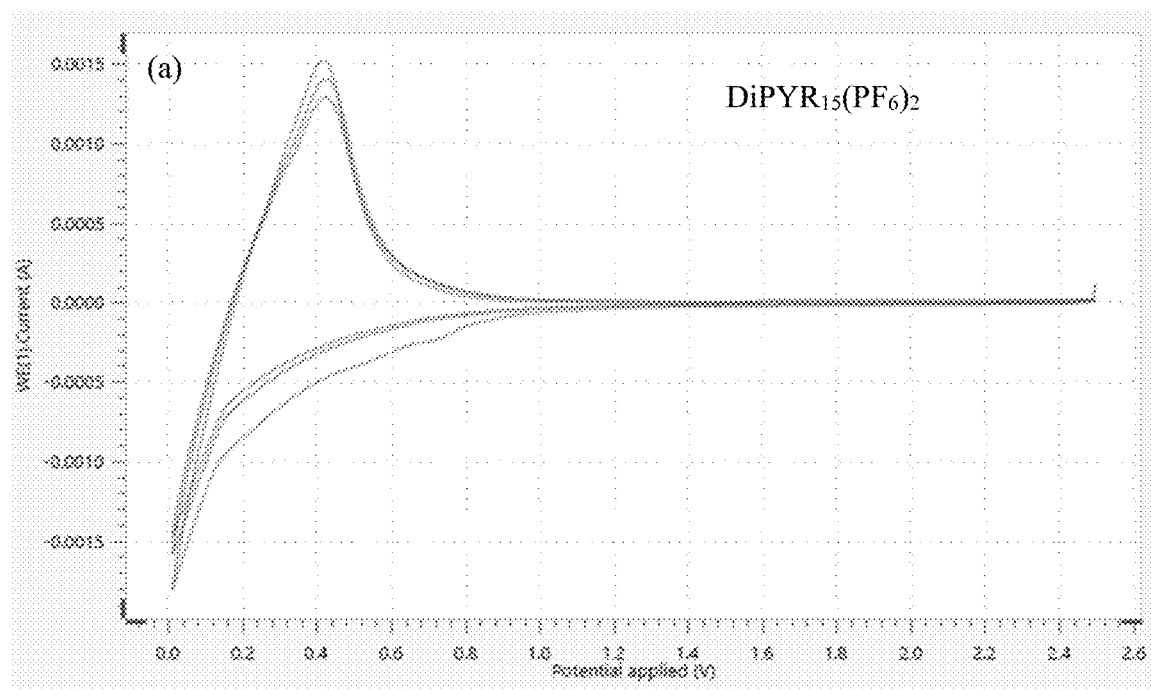
FIG. 18A is a graph showing results of a linear sweep voltammetry LSV of Di PYR$_{15}$(PF$_6$)$_2$.
Figure 18B:
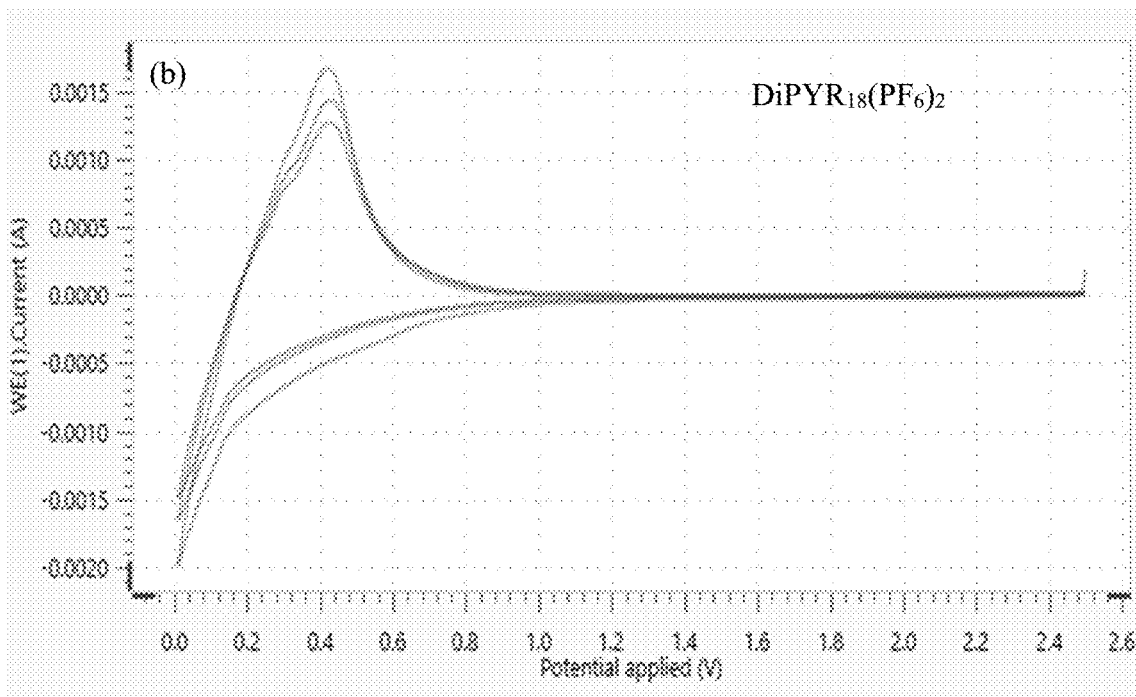
FIG. 18B is a graph showing results of a linear sweep voltammetry LSV of Di PYR$_{18}$(PF$_6$)$_2$.
Figure 19A:
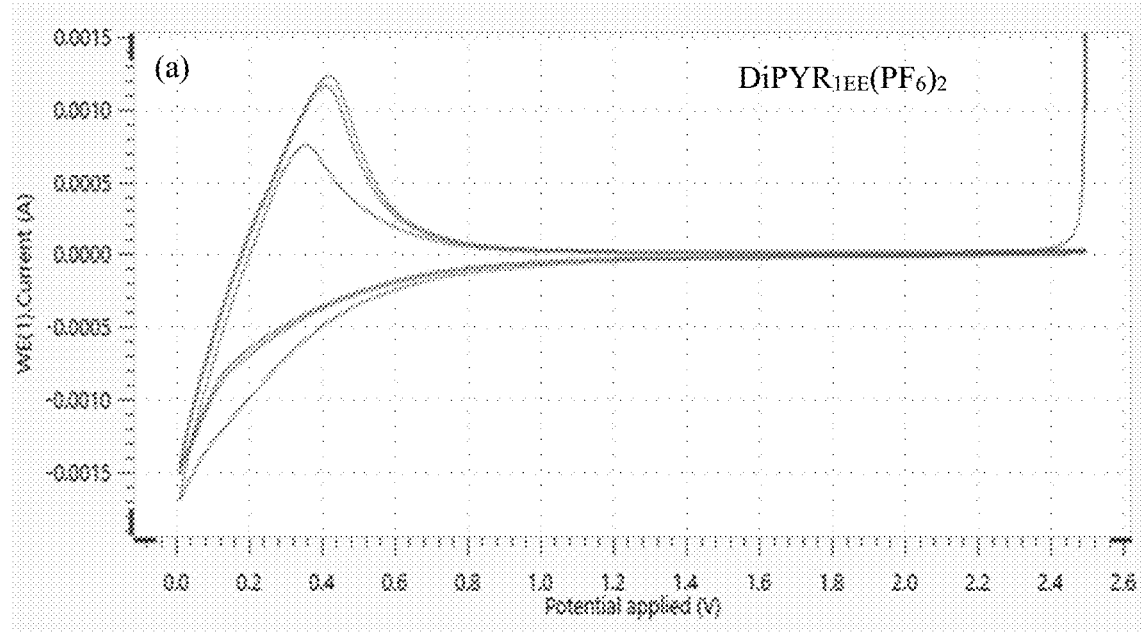
FIG. 19A is a graph showing results of a linear sweep voltammetry LSV of DiPYR$_{IEE}$(PF$_6$)$_2$.
Figure 19B:
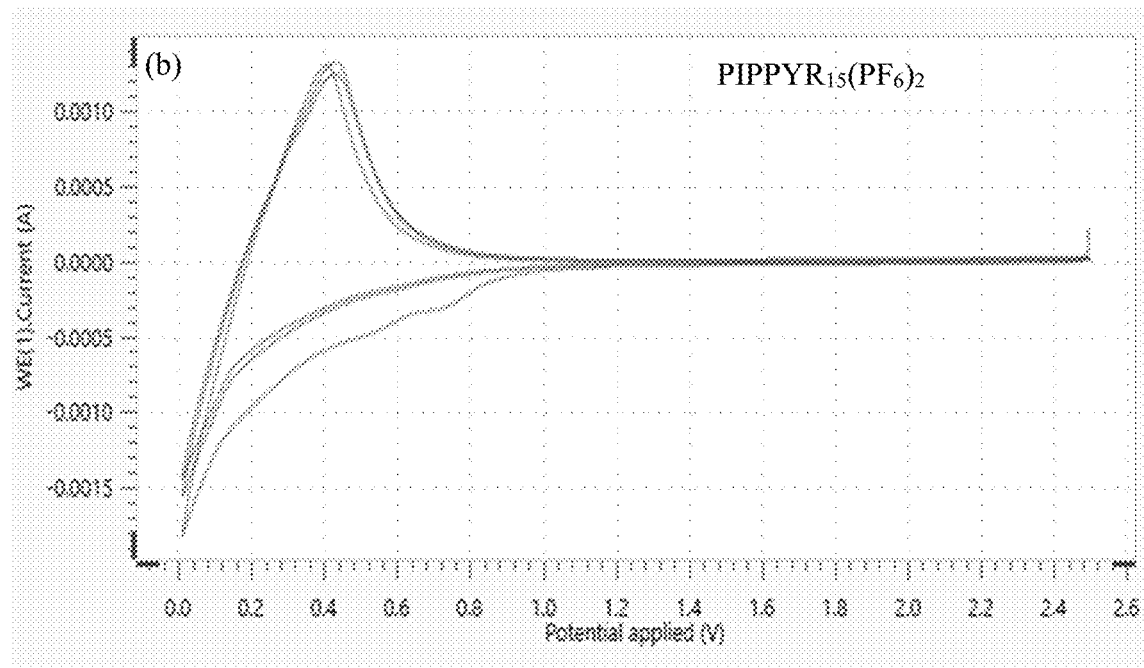
FIG. 19B is a graph showing results of a linear sweep voltammetry LSV of PIPPYR15(PF$_6$)$_2$.
Figure 19C:
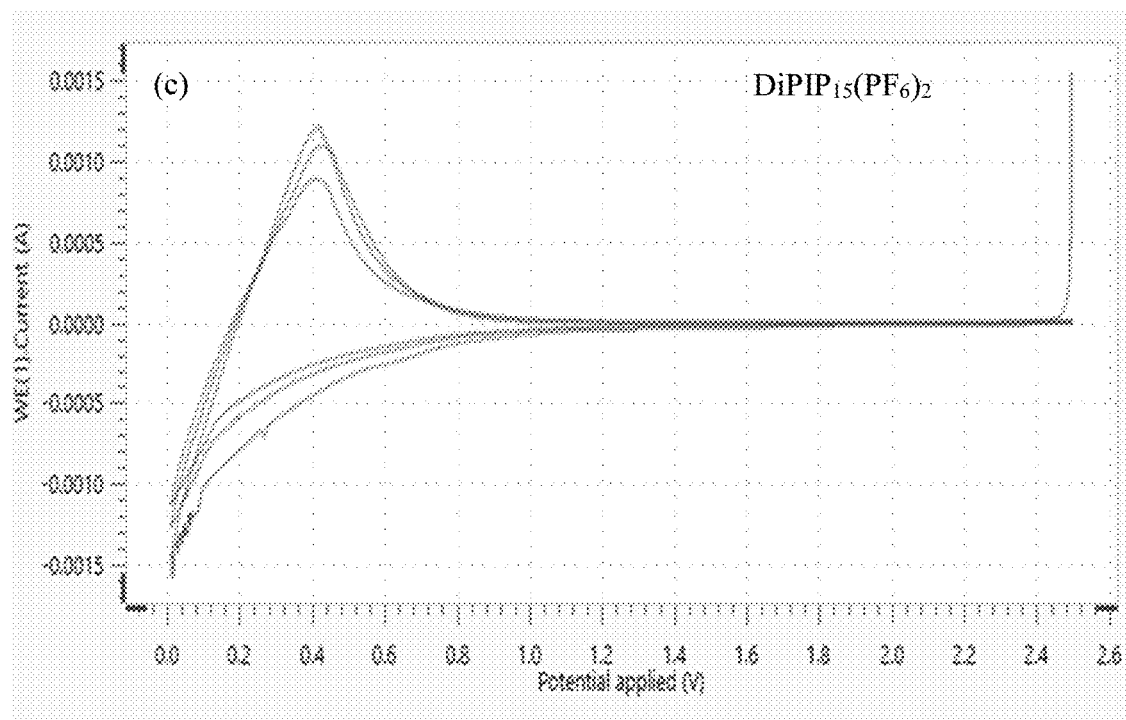
FIG. 19C is a graph showing results of a linear sweep voltammetry LSV of DiPIP$_{15}$(PF$_6$)$_2$.
Figure 19D:
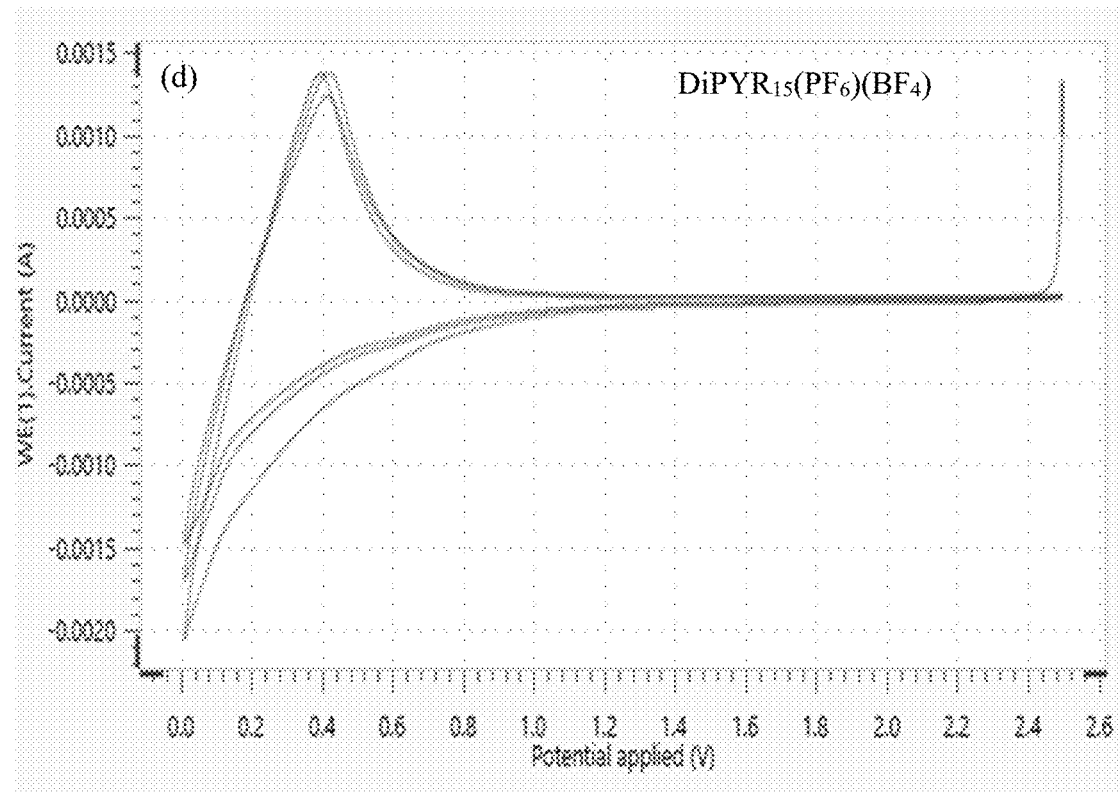
FIG. 19D is a graph showing results of a linear sweep voltammetry LSV of DiPYR$_{15}$(PF$_6$)(BF$_4$)

2. Two-core cationic chain ionic liquid: 1,5 Bis(1-methylpyrrolidium 1-yl) pentane dihexafluorophosphate $[DiPYR_{15}(PF_6)_2]$, 1,8 Bis(1-methylpyrrolidium 1-yl) octane dihexafluorophosphate $[DiPYR_{18}(PF_6)_2]$
   Electrolyte: (a) 1M $LiPF_6$+EC:DMC:EMC=1:1:1 (vol.)+1 wt. % VC+10 wt. % $DiPYR_{15}(PF_6)_2$, (b) 1M $LiPF_6$+EC:DMC:EMC=1:1:1 (vol.)+1 wt. % VC+10 wt. % $DiPYR_{18}(PF_6)_2$
   With reference to FIGS. 18A and 18B, there was no reduction peak at 0.7-1.0 V when 10 wt. % of $DiPYR_{15}(PF_6)_2$ or 10 wt. % of $DiPYR_{18}(PF_6)_2$ ionic liquid is added to the electrolyte. This indicates that when the molecular weight and functional group of the cation is sufficiently large, the ionic liquid would not be able to intercalate into the MCMB layered structure. The ionic liquids with two-core cationic chain or the cation ionic liquid with aromatic bonded to the cation according to the invention, in which the two cations are linked together, their molecular weight is increased sufficiently so as to result in poor intercalation into the anode material.

3. Replacement of the alkyl chain Y with other functional groups, and replacement of the cation $X_1$ and $X_2$ with other heterocyclic aromatic or amine, and replacement of other anionic groups $Z_1$ and $Z_2$: Taking the following two ionic liquids with dual core cationic chain as examples: bis[2-(1-methylpyrrolidinium 1-yl) ethyl] ether dihexafluorophosphate $[DiPYR_{IEE}(PF_6)_2]$, 1,5-(1-methylpyrrolidin 1-yl)(1-methylpiperidinium 1-yl) pentane dihexafluorophosphate $[PYRPIP_{15}\ (PF_6)_2]$, $_{1,5}$-bis(1-methylpiperidinium 1-yl) pentane dihexafluorophosphate

[DiPIP$_{15}$(PF$_6$)$_2$], 1,5-bis(1-methylpyrrolidium 1-yl) pentane (hexafluorophosphate) (tetrafluoroborate) [DiPYR$_{15}$(PF$_6$)(BF$_4$)]

Electrolyte: (a) 1M LiPF$_6$+EC:DMC:EMC=1:1:1 (vol.)+1 wt. % VC+15 wt. % DiPYR$_{IEE}$(PF$_6$)$_2$, (b) 1M LiPF$_6$+EC:DMC:EMC=1:1:1 (vol.)+1 wt. % VC+10 wt. % PYRPIP$_{15}$(PF$_6$)$_2$, (c) 1M LiPF$_6$+EC:DMC:EMC=1:1:1 (vol.)+1 wt. % VC+10 wt. % DiPIP$_{15}$(PF$_6$)$_2$, (d) 1M LiPF$_6$+EC:DMC:EMC=1:1:1 (vol.)+1 wt. % VC+15 wt. % DiPYR$_{is}$(PF$_6$)(BF$_4$)

With reference to FIGS. 19A to 19D, there is no reduction peak at 0.7-1.0 V when DiPYR$_{IEE}$(PF$_6$)$_2$, DiPIPPYR$_{15}$(PF$_6$)$_2$, DiPIP$_{15}$(PF$_6$)$_2$ or DiPYR$_{15}$(PF$_6$)(BF$_4$) ionic liquid is added to the electrolyte. It indicates that the molecular weight of the two-core structure and its functional group is sufficiently large to minimize intercalation into the MCMB layered structure, yet does not hinder the intercalation and exfoliation of lithium ions. The interface impedance on the surface of the anode is reduced.

Embodiment 5

A pouch cell battery with a capacity of 40 Ah with the ionic liquid added to the organic electrolyte is used to verify or authenticate the composition and structure of a solid electrolyte interface film (SEI) on the surface of the anode during the charging and discharging processes of the lithium ion battery with the two-core structure ionic liquid according to the invention developed in this patent. In the test, the battery undergo splint formation to charge to 3.5 V, and then discharge with a small current to 2.0 V. The battery is disassembled in an inert atmosphere glove box with the anode being removed. The removed anode is soaked in the dimethyl carbonate (DMC) for about 15 minutes, followed by shaking the anode to remove any remaining lithium salt. The anode is then left to dry in the shade.

The National Synchrotron Radiation Research Center (NSRRC) Beamline at the 20A1 station is used to perform Soft X-ray Absorption Spectroscopy (sXAS) to verify the composition and structure of the SEI film on the surface of anode. The oxygen K-edge absorption spectrum includes total electron yield (TEY) and total fluorescence yield (TFY). In TEY, due to the restraint of the coulomb force between electrons, it would not be easy for the electrons deep inside the electrode to reach the electrode surface and be received. Only the electrons close to the surface are attracted by the applied bias and are received by the receiver. As such, the structure of the material in the range of 10 nm on a surface can be analyzed. As for the TFY, fluorescence is composed of photons, it will not be restricted by the coulomb force. It is useful in detecting/analyzing electronic structure deeper within the electrode, i.e. in the range of 200 nm on a surface.

Synchrotron sXAS Experiment Conditions:
1. A pouch cell of lithium iron phosphate (LFP) battery with the capacity of 40 Ah.
2. Splint formation: charge at the 0.01 C for 3 hours, charge at the 0.1 C to 3.6 V, and then discharge at the 0.1 C to 2.0 V;
3. The anode material is meso carbon micro bead MCMB: SuperP:CMC:SBR=95.5:1.0:1.5:2.0;
4. Electrolyte: (a) Organic electrolyte (OE): 1M LiPF$_6$+EC:DMC:EMC=1:1:1 (vol.)+1 wt. % VC, (b) 1M LiPF$_6$+EC:DMC:EMC=1:1:1 (vol.)+1 wt. % VC+6 wt. % PYRTEA$_{15}$(PF$_6$)$_2$, (c) 1M LiPF$_6$+EC:DMC:EMC=1:1:1 (vol.)+1 wt. % VC+6 wt. % DiPYR$_{15}$(PF$_6$)$_2$, (d) 1M LiPF6+EC:DMC:EMC=1:1:1 (vol.)+1 wt. % VC+6 wt. % DiPYR$_{IEE}$(PF$_6$)$_2$;
5. Oxygen K-edge total electron yield (TEY), Energy range: 525~555 eV.

Figure 20:
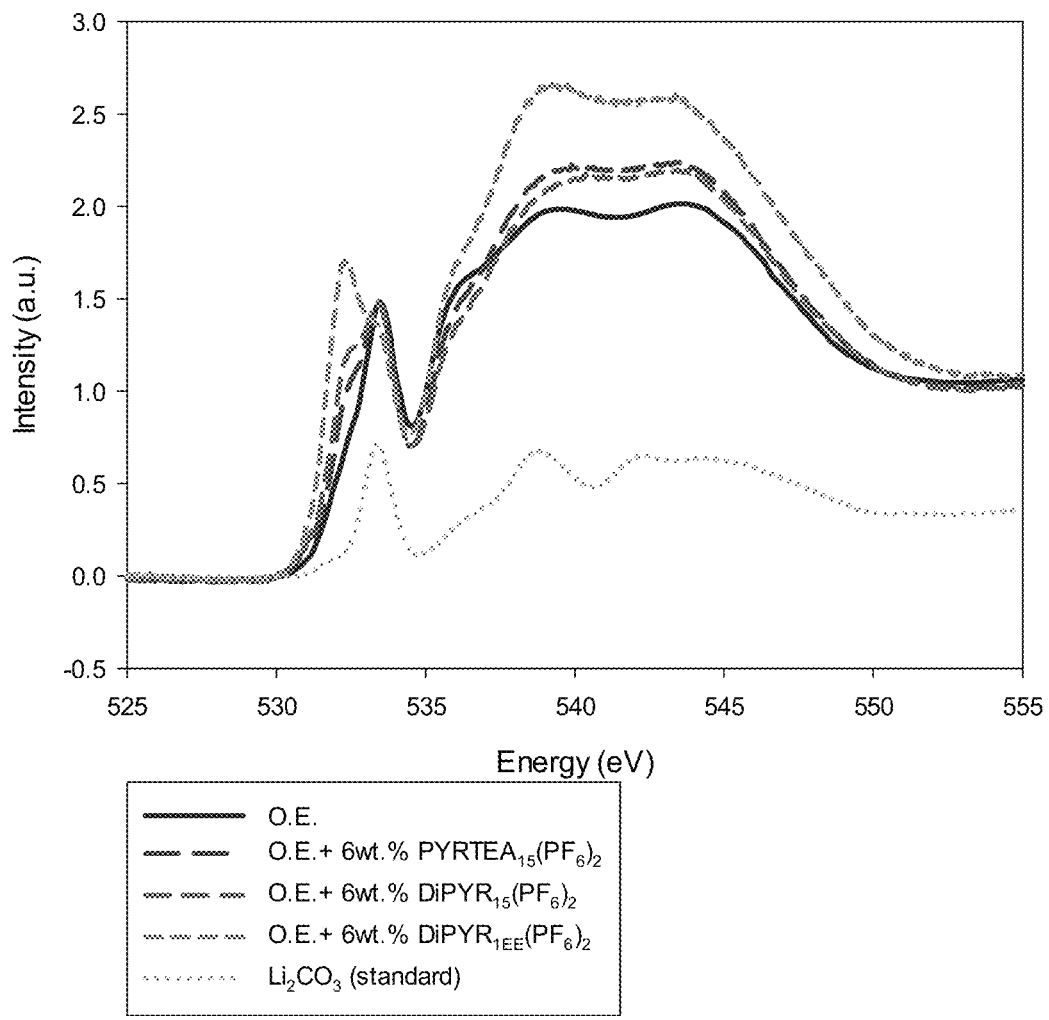
FIG. 20 is a graph showing results of Li$_2$CO$_3$ product, PYRTEA$_{15}$(PF$_6$)$_2$ added at 6 wt. % to the OE, DiPYR$_{15}$(PF$_6$)$_2$ added at 6 wt. % to the OE and DiPYR$_{IEE}$(PF$_6$)$_2$ added at 6 wt. % to the OE as well as an organic electrolyte (OE) being tested by X-ray absorption spectrum O K-edge TEY.

With reference to FIG. 20, the standard Li$_2$CO$_3$ product is tested by X-ray absorption spectrum O K-edge TEY. The characteristic peak positions of C=O ($\pi$*bond) and C—O ($\alpha$*bond) of CO$_3^{2-}$ are at 533.5 eV, 538.7 eV and 542 eV, respectively. A pouch cell of LFP battery with the capacity of 40 Ah with organic electrolyte (OE) without adding any ionic liquid of the invention is charged at the 0.01 C for 3 hours, charge at the 0.1 C to 3.6 V, and then discharged at the 0.1 C to 2.0 V, the SEI film produced by the reaction of interface between the electrolyte and anode is detected. The TEY test result shows that the characteristic curve is similar to that of the standard Li$_2$CO$_3$, and an obvious characteristic peak appears at 533.5 eV, indicating that the structure of SEI film produced by the OE electrolyte is mainly Li$_2$CO$_3$.

Again with reference to FIG. 20, the ionic liquid with dual core structure, including PYRTEA$_{15}$(PF$_6$)$_2$, DiPYR$_{15}$(PF$_6$)$_2$ and DiPYR$_{IEE}$(PF$_6$)$_2$ are added at 6 wt. % to the OE electrolyte respectively. Three samples of pouch cell LFP battery, capacity of 40 Ah is used, with OE+PYRTEA$_{15}$(PF$_6$)$_2$, organic electrolyte (OE)+DiPYR$_{15}$(PF$_6$)$_2$ and OE+DiPYR$_{IEE}$(PF$_6$)$_2$ respectively. The surface of the anodes is tested by the sXAS absorption spectrum O K-edge TEY. Each of them shows an obvious Li$_2$CO$_3$ characteristic peak at 533.5 eV, but the other peaks also appear at the position of 532~533 eV. The main components includes the characteristic peaks of COH at 531.7 eV and the O—O of organic lithium salt ROCO$_2$Li at 532.5 eV, which means in each of the three samples, a thin layer of organic film is formed in the range of ~5 nm on the surface of anode. The amount of organic film formed in the three samples are of the order of OE+DiPYR$_{IEE}$(PF$_6$)$_2$>OE+DiPYR$_{15}$(PF$_6$)$_2$>OE+PYRTEA$_{15}$(PF$_6$)$_2$. It is concluded that the addition of the ionic liquids according to the invention not only inhibits the intercalation at the anode, but also result in the formation of a thin layer of organic film on the anode surface. By adding an appropriate amount of the ionic liquid to the electrolyte, the interface resistance will be reduced and the thermal stability of the overall lithium-ion battery will be improved as the ionic liquid has high melting point and is an effective flame retardant.

Embodiment 6

The performance of LFP batteries with the pouch cell of 40 Ah and 60 Ah with different electrolyte formulations.

Preparation of Cathode Sheet

Cathode active material: LFP, binder: polyvinylidene fluoride (PVDF), conductive agent: carbon black (Super P®) are mixed according to the weight ratio of LFP:Super P:PVDF=96:2:2, followed by adding the solvent: N-methyl pyrrolidone. It is then stirred and dispersed uniformly in a vacuum stirring machine to obtain the cathode slurry. The cathode slurry is uniformly coated on an aluminum foil by a coating machine, and the solvent is removed by the drying in hot air. The cathode sheet is obtained by cold pressing and slitting.

Preparation of Anode Sheet

Anode active material: meso carbon micro bead (MCMB), conductive agent: carbon black (Super P), thickener: sodium carboxymethyl cellulose (CMC), binder: styrene butadiene rubber (SBR) emulsion are mixed in a ratio of MCMB:Super P:CMC:SBR=95.5:1.0:1.5:2.0 with deionized water as solvent. It is stirred and dispersed uniformly in a vacuum stirring machine to obtain the anode slurry. The anode slurry is uniformly coated on the copper foil by a coating machine, and the solvent is removed by the drying in hot air. Anode sheet is obtained by cold pressing and slitting.

Preparation of Electrolyte

Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 mole/L (M) of $LiPF_6$ in the specified sequence. The electrolyte is formed after mixing. Electrolyte with different film-forming agent (A), stabilizer (B), ionic liquid (C) are shown in FIG. 21A, FIG. 21B and Table 9.

With Reference to FIG. 21A, Electrolyte Formula 1:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A) and 1 M of $LiPF_6$ in the specified sequence. Film-forming agent (A): VC: Vinylene carbonate at 1 wt. %. The electrolyte is formed after mixing.

With Reference to FIG. 21A, Electrolyte Formula 2:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A) and 1 M of $LiPF_6$ in the specified sequence. Film-forming agent (A) is VC: Vinylene carbonate at 1 wt. % and FEC: Fluoroethylene carbonate at 1 wt. %. The electrolyte is formed after mixing.

With Reference to FIG. 21A, Electrolyte Formula 3:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is EPFCP: Ethoxy(pentafluoro)cyclotriphosphazene at 3 wt. %. The electrolyte is formed after mixing.

With Reference to FIG. 21A, Electrolyte Formula 4:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the ionic liquid (C) is $PYR_{13}PF_6$ at 5 wt. %. The electrolyte is formed after mixing.

With Reference to FIG. 21A, Electrolyte Formula 5:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is HFCP: Hexafluoro cyclotriphosphazene at 2.9 wt. %, the ionic liquid (C) is $PYR_{13}PF_6$ at 5 wt. %. The electrolyte is formed after mixing.

With Reference to FIG. 21A, Electrolyte Formula 6:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is EPFCP: Ethoxy(pentafluoro)cyclotriphosphazene at 2.9 wt. %, the ionic liquid (C) is $PYR_{13}PF_6$ at 5 wt. %. The electrolyte is formed after mixing.

With Reference to FIG. 21A, Electrolyte Formula 7:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is EPFCP: Ethoxy(pentafluoro)cyclotriphosphazene at 2.9 wt. %, the ionic liquid (C) is $PYR_{13}PF_6$ at 10 wt. %. The electrolyte is formed after mixing.

With Reference to FIG. 21A, Electrolyte Formula 8:
LFP Batteries with the Pouch Cell of 40 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is EPFCP: Ethoxy(pentafluoro)cyclotriphosphazene at 2.9 wt. %, the ionic liquid (C) is $PYR_{13}PF_6$ at 15 wt. %. The electrolyte is formed after mixing.

With Reference to FIG. 21A, Electrolyte Formula 9:
LFP Batteries with the Pouch Cell of 60 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), ionic liquid (C) and 1 M of LiPF6 in the specified sequence. Film-forming agent (A) is VC: Vinylene carbonate at 1 wt. % and FEC: Fluoroethylene carbonate at 1 wt. %, the stabilizer, the ionic liquid (C) is $DiPYR_{15}(PF_6)_2$ at 6 wt. %. The electrolyte is formed after mixing.

With Reference to FIG. 21A, Electrolyte Formula 10:
LFP Batteries with the Pouch Cell of 60 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is HFCP at 2 wt. %, the ionic liquid (C) is $DiPYR_{15}(PF_6)_2$ at 6 wt. %. The electrolyte is formed after mixing.

With Reference to FIG. 21A, Electrolyte Formula 11:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is EPFCP at 2 wt. %, the ionic liquid (C) is $DiPYR_{15}(PF_6)_2$ at 6 wt. %. The electrolyte is formed after mixing.

With Reference to FIG. 21A, Electrolyte Formula 12:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is EPFCP at 2 wt. %, the ionic liquid (C) is $DiPYR_{15}(PF_6)_2$ at 8 wt. %. The electrolyte is formed after mixing.

With Reference to FIG. 21A, Electrolyte Formula 13:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 1 wt. %, the stabilizer (B) is EPFCP at 2 wt. %, the ionic liquid (C) is $DiPYR_{15}(PF_6)_2$ at 10 wt. %. The electrolyte is formed after mixing.

With Reference to FIG. 21A, Electrolyte Formula 14:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 2 wt. % and FEC: Fluoroethylene carbonate at 1 wt. %, the stabilizer (B) is EPFCP at 2 wt. %, the ionic liquid (C) is $DiPYR_{15}(PF_6)_2$ at 6 wt. %. The electrolyte is formed after mixing.

With Reference to FIG. 21A, Electrolyte Formula 15:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 3 wt. % and FEC: Fluoroethylene carbonate at 1 wt. %, the stabilizer (B) is EPFCP at 2 wt. %, the ionic liquid (C) is $DiPYR_{15}(PF_6)_2$ at 6 wt. %. The electrolyte is formed after mixing.

With Reference to FIG. 21B, Electrolyte Formula 16:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 2 wt. %, the stabilizer (B) is EPFCP at 2 wt. %, the ionic liquid (C) is $DiPYR_{15}(PF_6)_2$ at 6 wt. %. The electrolyte is formed after mixing.

With Reference to FIG. 21B, Electrolyte Formula 17:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of LiPF6 in the specified sequence. Film-forming agent (A) is VC: Vinylene carbonate at 1 wt. % and FEC: Fluoroethylene carbonate at 3 wt. %, the stabilizer (B) is EPFCP at 2 wt. %, the ionic liquid (C) is $DiPYR_{15}(PF_6)_2$ at 6 wt. %. The electrolyte is formed after mixing.

With Reference to FIG. 21B, Electrolyte Formula 18:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 2 wt. %, the stabilizer (B) is EPFCP at 2.8 wt. %, the ionic liquid (C) is $Furoyl-PYR_{11}(PF_6)_2$ at 6 wt. %. The electrolyte is formed after mixing.

With Reference to FIG. 21B, Electrolyte Formula 19:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 2 wt. %, the stabilizer (B) is EPFCP at 2.8 wt. %, the ionic liquid (C) is $DiPYR_{15}(PF_6)_2$ at 6 wt. %. The electrolyte is formed after mixing.

With Reference to FIG. 21B, Electrolyte Formula 20:
LFP Batteries with the Pouch Cell of 60 Ah Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt $LiPF_6$ is dissolved in the organic solvent followed by adding film-forming agent (A), stabilizer (B), ionic liquid (C) and 1 M of $LiPF_6$ in the specified sequence. Film-forming agent (A) is VC: Vinylene carbonate at 1 wt. % and FEC: Fluoroethylene carbonate at 2 wt. %, the stabilizer (B) is EPFCP at 2.8 wt. %, the ionic liquid (C) is DiPYR$_{IEE}$(PF$_6$)$_2$ at 6 wt. %. The electrolyte is formed after mixing.

With Reference to FIG. 21B, Electrolyte Formula 21:
LFP Batteries with the Pouch Cell of 60 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt LiPF$_6$ is dissolved in the organic solvent followed by adding film-forming agent (A), stabilizer (B), ionic liquid (C) and 1 M of LiPF$_6$ in the specified sequence. Film-forming agent (A) is VC: Vinylene carbonate at 1 wt. % and FEC: Fluoroethylene carbonate at 2 wt. %, the stabilizer (B) is EPFCP at 2.5 wt. %, the ionic liquid (C) is PYRPIP$_{IEE}$(PF$_6$)$_2$ at 6 wt. %. The electrolyte is formed after mixing.

With Reference to FIG. 21B, Electrolyte Formula 22:
LFP Batteries with the Pouch Cell of 60 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt LiPF$_6$ is dissolved in the organic solvent followed by adding film-forming agent (A), stabilizer (B), ionic liquid (C) and 1 M of LiPF$_6$ in the specified sequence. Film-forming agent (A) is VC: Vinylene carbonate at 1 wt. % and FEC: Fluoroethylene carbonate at 2 wt. %, the stabilizer (B) is EPFCP at 2.5 wt. %, the ionic liquid (C) is DiPIP$_{15}$(PF$_6$)$_2$ at 6 wt. %. The electrolyte is formed after mixing.

With Reference to FIG. 21B, Electrolyte Formula 23:
LFP Batteries with the Pouch Cell of 60 Ah
Organic solvent (OE): Ethylene carbonate (EC), dimethyl carbonate (DMC) and ethyl methyl carbonate (EMC) are mixed according to the weight ratio of EC:DMC:EMC=1:1:1. The lithium salt LiPF$_6$ is dissolved in the organic solvent followed by adding film-forming agent (A), stabilizer (B), ionic liquid (C) and 1 M of LiPF$_6$ in the specified sequence. Film-forming agent (A) is VC: Vinylene carbonate at 1 wt. % and FEC: Fluoroethylene carbonate at 2 wt. %, the stabilizer (B) is EPFCP at 2.5 wt. %, the ionic liquid (C) is DiPYR$_{15}$(PF$_6$)(BF$_4$) at 6 wt. %. The electrolyte is formed after mixing.

Figure 22A:
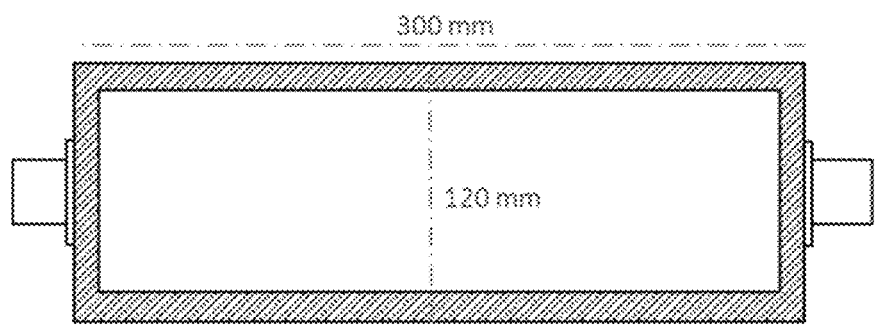
FIG. 22A shows a top plan view of a LFP battery (Lithium-ion battery) in accordance with the invention.
Figure 22B:
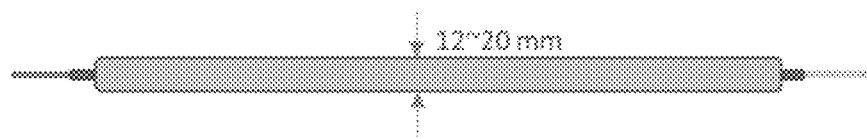
FIG. 22B shows a side view of the LFP batter in FIG. 22A.

Formation of LFP Battery
With reference to FIGS. 22A and 22B, cathode sheet, anode sheet, and separator are laminated. Ultrasonic welding is used to attach the conductive lugs to obtain a bare battery cell. The bare battery cell is inserted into the aluminum-plastic film pit. After encapsulation, any one of the electrolytes 1 to 23 as detailed in FIG. 21/Table 9 is injected. The pouch is sealed. The pouch battery is allowed to stand, undergo cold pressing, formation, exhausting, capacity testing, aging and other processes, the pouch cell of LFP battery with the capacity of 40~60 Ah is obtained. The specification of battery is shown in the figure below.

Self-extinguishing time SET of electrolyte for battery prepared according to FIG. 21/Table 9
1.2 g of each electrolyte as detailed in FIG. 21/Table 9 is placed onto a glass fiber filter with a diameter of 47 mm and a thickness of 0.5 mm. The electrolyte is ignited and burnt. The time from ignition to extinguishment per gram of electrolyte in each of the batteries in FIG. 21/Table 9 is recorded, the unit is sec/g, referred to as the self-extinguishing time (Self-extinguish time, SET). Each of Electrolyte formula 1 to 23 are tested respectively. The results are produced in FIG. 10.

Performance Test of Lithium-Ion Battery Prepared According to FIG. 21/Table 9

At 25° C., each LFP battery with any one of electrolyte 1 to 23 is charged to 3.6 V at a constant current of 0.5 C followed by charging the battery at a constant voltage of 3.6 V until the current drops to 0.05 C, and then discharged to 2.5 V at a constant current of 0.5 C. This is one charge-discharge cycle and this is the first discharge capacity of lithium-ion battery. Under the aforementioned charge and discharge conditions, the lithium-ion battery is subjected to multiple cycles of testing until the discharge capacity reaches 80% of the first discharge capacity (The capacity retention (C.R.) being 80%). The number of charge and discharge cycles until C.R.=80% of respective batteries is recorded. The results are produced in FIG. 10. The lithium ion battery with different electrolyte formula (1 to 23) are tested respectively.

Figure 10A:
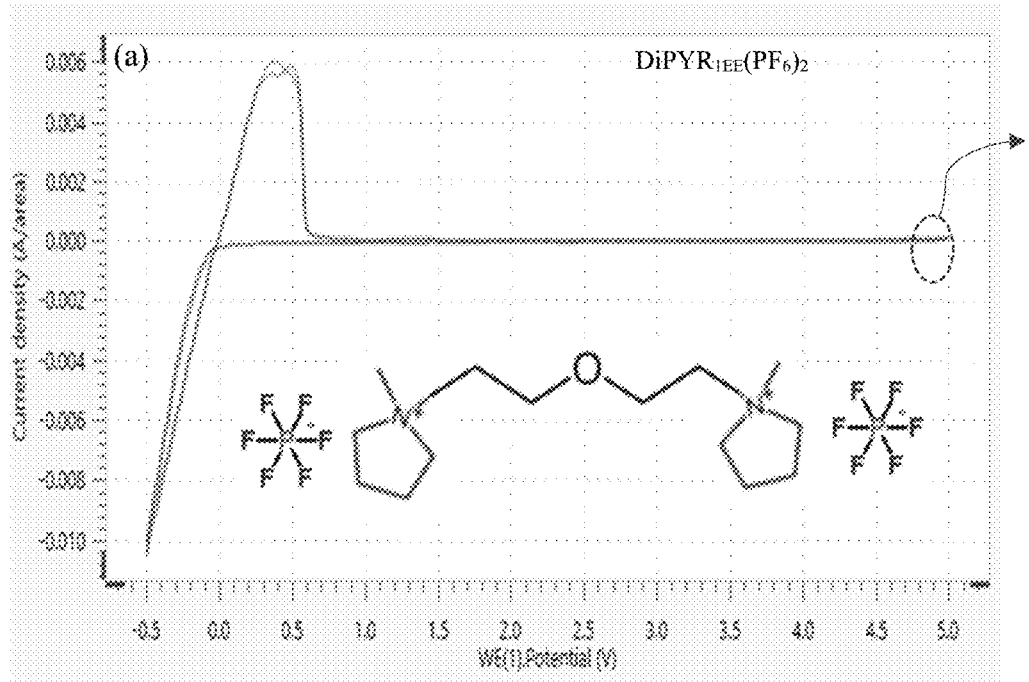
FIG. 10A is a graph showing results of a linear sweep voltammetry LSV of $DiPYR_{IEE}(PF_6)_2$.
Figure 10B:
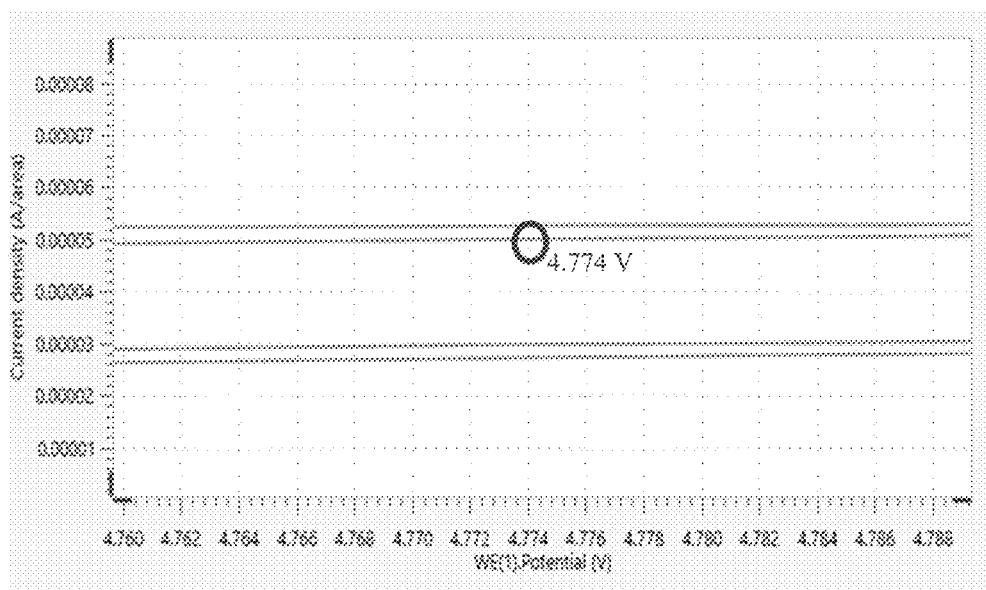
FIG. 10B is a graph showing the reading of the circled part in FIG. 10A.
Figure 11A:
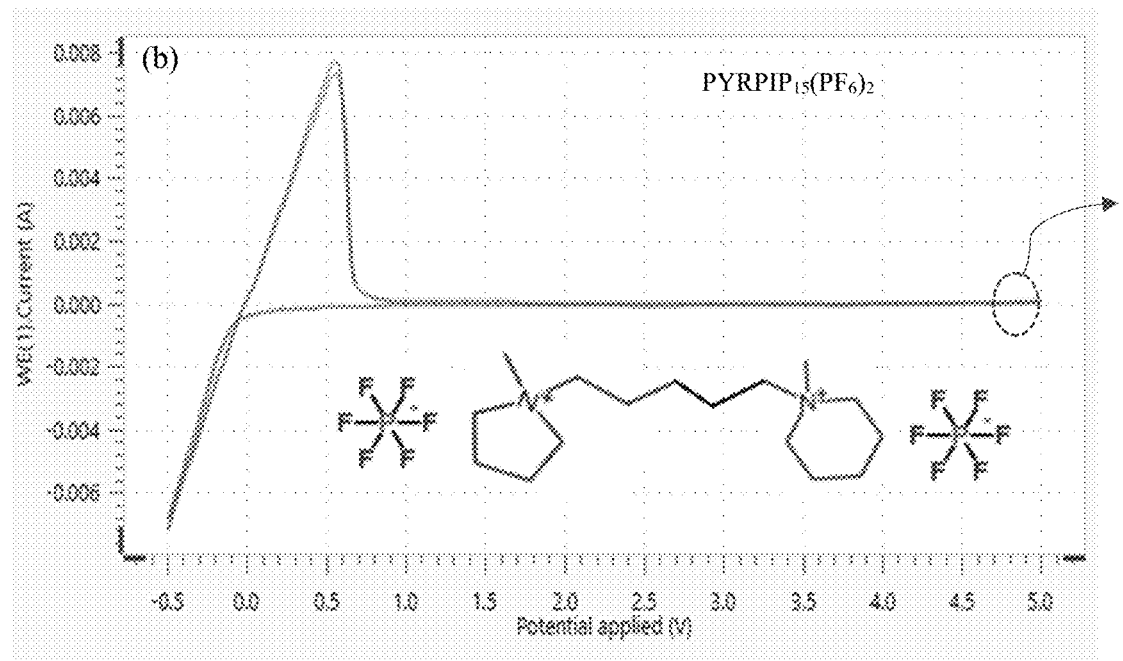
FIG. 11A is a graph showing results of a linear sweep voltammetry LSV of $PYRPIP_{15}(PF_6)_2$.
Figure 11B:
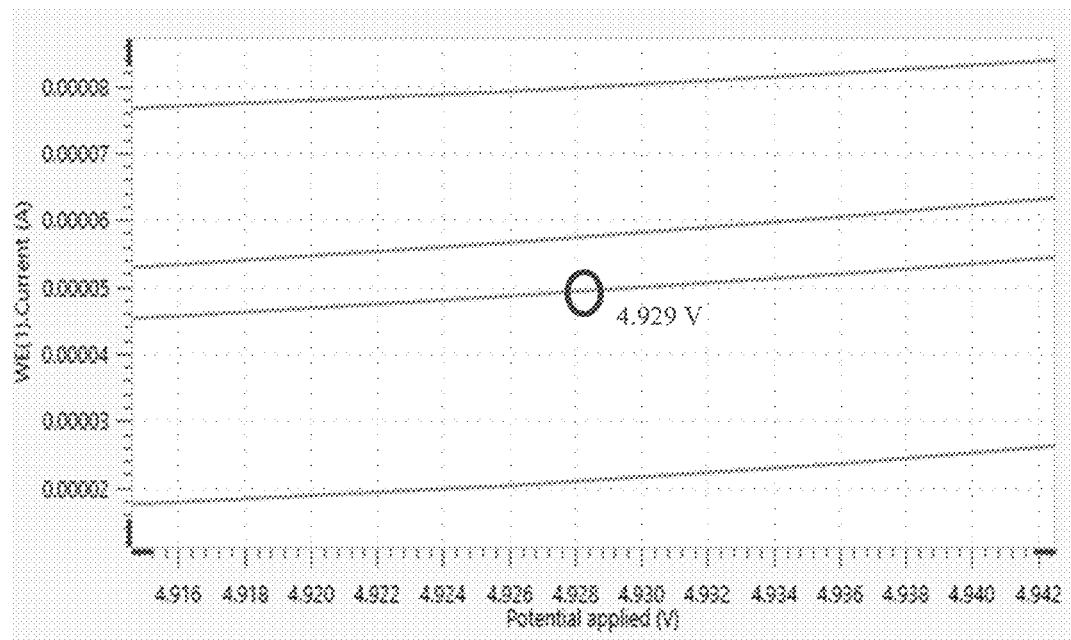
FIG. 11B is a graph showing the reading of the circled part in FIG. 11A.
Figure 12A:
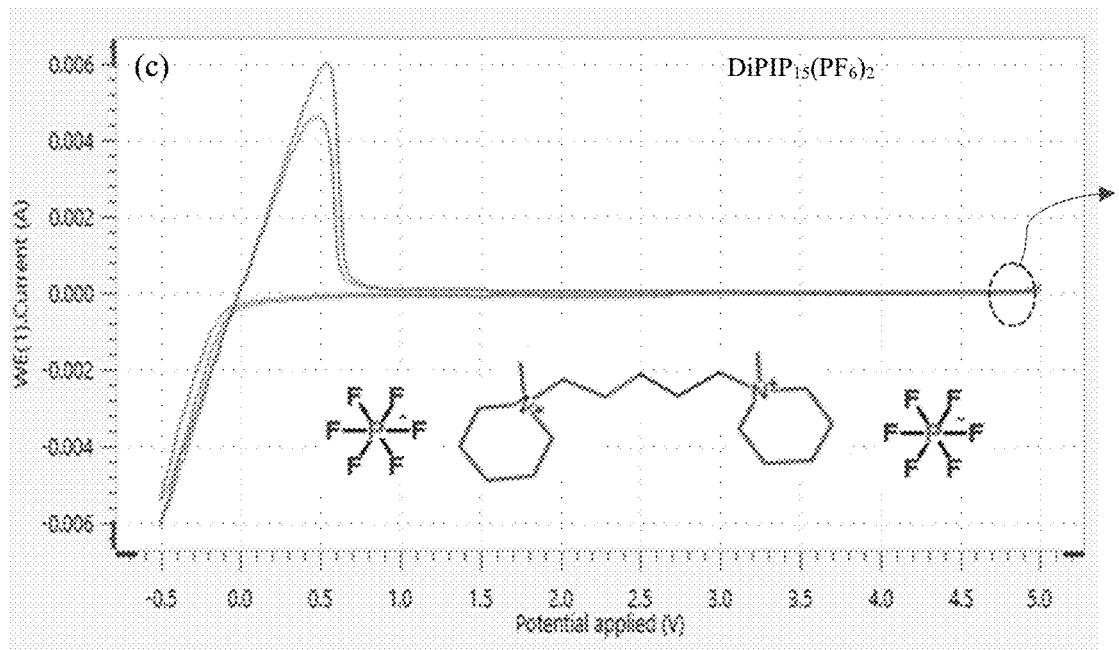
FIG. 12A is a graph showing results of a linear sweep voltammetry LSV of DiPIP$_{15}$(PF$_6$)$_2$.
Figure 12B:
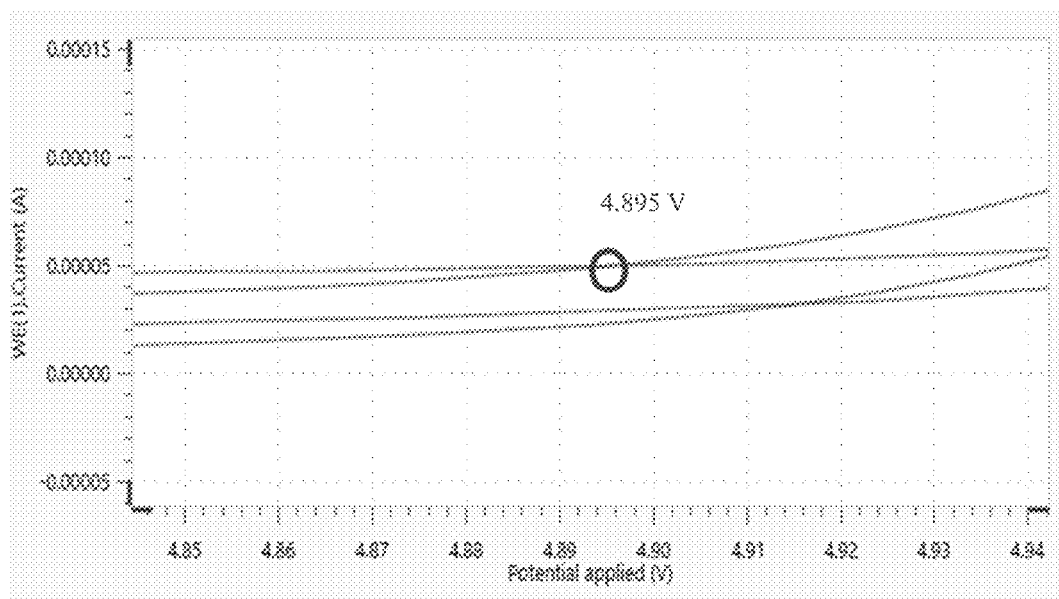
FIG. 12B is a graph showing the reading of the circled part in FIG. 12A.
Figure 13A:
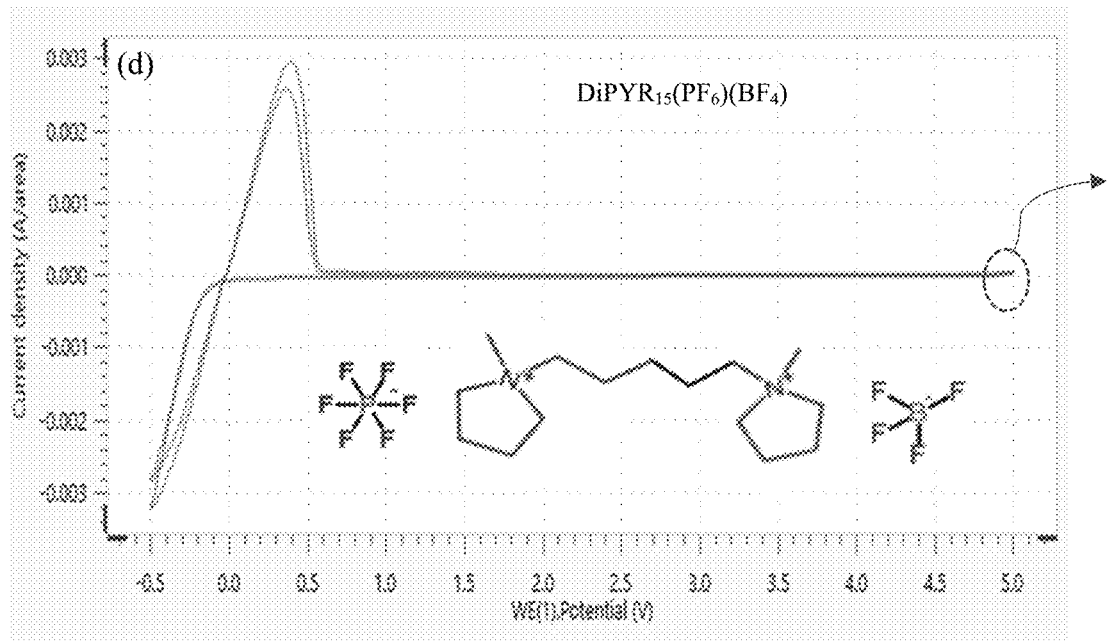
FIG. 13A is a graph showing results of a linear sweep voltammetry LSV of DiPYR$_{15}$(PF$_6$)(BF$_4$)
Figure 13B:
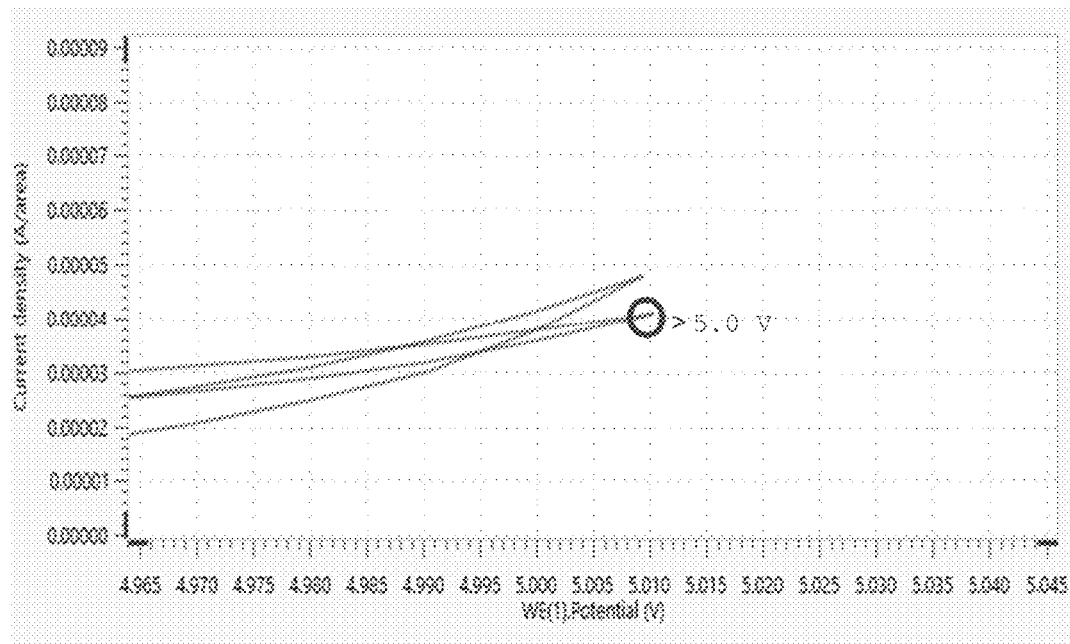
FIG. 13B is a graph showing the reading of the circled part in FIG. 13A.
Figure 14A:
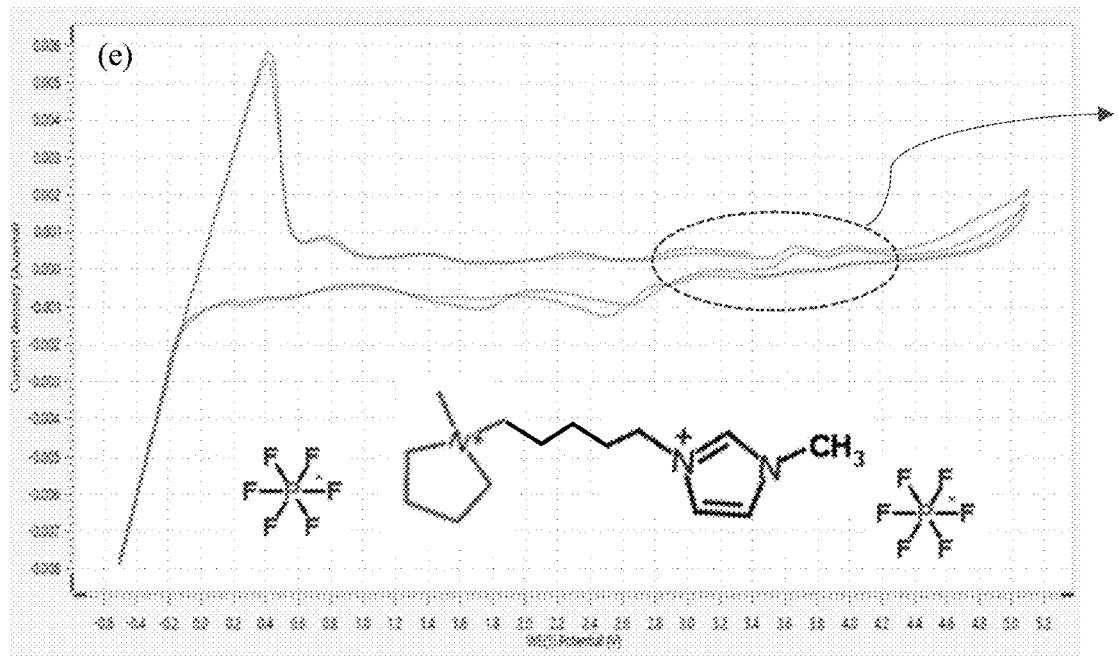
FIG. 14A is a graph showing results of a linear sweep voltammetry LSV of DiPYR$_{15}$(PF$_6$)(BF$_4$)
Figure 14B:
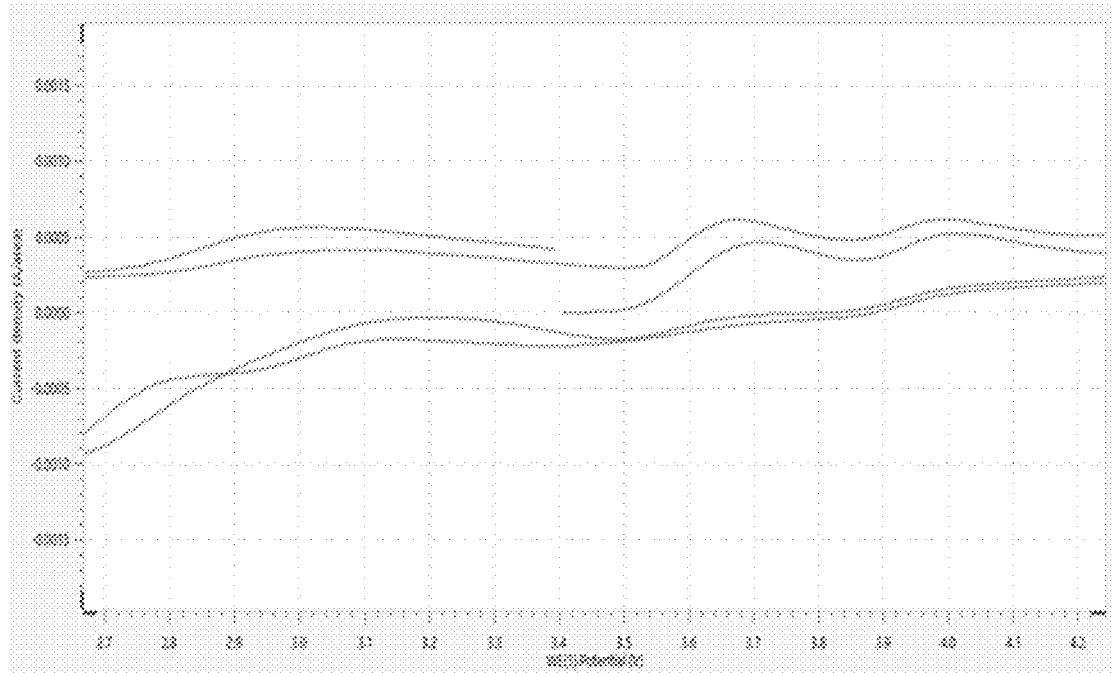
FIG. 14B is a graph showing the reading of the circled part in FIG. 14A.

Internal Impedance Test
The internal impedance AC IR value of the lithium ion battery with any one of electrolyte formula 1 to 23 as detailed in Table 9 is detected by HIOKI BT3561 battery internal resistance meter and the results are recorded in FIG. 10.

Referring to FIGS. 23A and 23B, it shows the performance of LFP battery in the form of pouch cell 40 Ah (No. 1 to 8) and the performance of LFP battery in the form of pouch cell 60 Ah (No. 9 to 23).

The self-extinguishing time, internal impedance and performance of each battery with any one of the electrolyte formulae listed in FIG. 23 are recorded in FIG. 10. The batteries are given the same number (No.) as the number of assigned to each electrolyte formulae as detailed in FIG. 23.

With reference to FIG. 23A, No. 1, the LFP battery 40 Ah with electrolyte formula 1 has a self-extinguishing time of 63 sec/g, an internal impedance ACIR (Alternate Current Internal Resistance) of 3.27 mΩ and the charge/discharge cycle number under 25 degree C. is 1359.

In No. 2, the LFP battery 40 Ah with electrolyte formula 2 has a self-extinguishing time of 58 sec/g, an internal impedance ACIR (Alternate Current Internal Resistance) of 3.05 mΩ and the charge/discharge cycle number under 25 degree C. is 1492.

In No. 3, the LFP battery 40 Ah with electrolyte formula 3 has a self-extinguishing time of 45 sec/g, an internal impedance ACIR (Alternate Current Internal Resistance) of 2.92 mΩ and the charge/discharge cycle number under 25 degree C. is 1553.

In No. 4, the LFP battery 40 Ah with electrolyte formula 4 has a self-extinguishing time of 36 sec/g, an internal impedance ACIR (Alternate Current Internal Resistance) of 3.48 mΩ and the charge/discharge cycle number under 25 degree C. is 1265.

In No. 5, the LFP battery 40 Ah with electrolyte formula 5 has a self-extinguishing time of 22 sec/g, an internal impedance ACIR (Alternate Current Internal Resistance) of 3.12 mΩ and the charge/discharge cycle number under 25 degree C. is 1463.

In No. 6, the LFP battery 40 Ah with electrolyte formula 6 has a self-extinguishing time of 18 sec/g, an internal impedance ACIR (Alternate Current Internal Resistance) of 2.86 mΩ and the charge/discharge cycle number under 25 degree C. is 1620.

In No. 7, the LFP battery 40 Ah with electrolyte formula 7 has a self-extinguishing time of 8 sec/g, an internal impedance ACIR (Alternate Current Internal Resistance) of 3.28 inn and the charge/discharge cycle number under 25 degree C. is 1335.

In No. 8, the LFP battery 40 Ah with electrolyte formula 8 has a self-extinguishing time of 3 sec/g, an internal impedance ACIR (Alternate Current Internal Resistance) of 4.37 mΩ and the charge/discharge cycle number under 25 degree C. is 1065.

In No. 9, the LFP battery 60 Ah with electrolyte formula 9 has a self-extinguishing time of 27 sec/g, an internal impedance ACIR (Alternate Current Internal Resistance) of 3.05 mΩ and the charge/discharge cycle number under 25 degree C. is 1517.

In No. 10, the LFP battery 60 Ah with electrolyte formula 10 has a self-extinguishing time of 17 sec/g, an internal impedance ACIR (Alternate Current Internal Resistance) of 2.56 mΩ and the charge/discharge cycle number under 25 degree C. is 1662.

In No. 11, the LFP battery 60 Ah with electrolyte formula 11 has a self-extinguishing time of 11 sec/g, an internal impedance ACIR (Alternate Current Internal Resistance) of 2.37 mΩ and the charge/discharge cycle number under 25 degree C. is 1918.

In No. 12, the LFP battery 60 Ah with electrolyte formula 12 has a self-extinguishing time of 8 sec/g, an internal impedance ACIR (Alternate Current Internal Resistance) of 2.69 mΩ and the charge/discharge cycle number under 25 degree C. is 1739.

In No. 13, the LFP battery 60 Ah with electrolyte formula 13 has a self-extinguishing time of 6 sec/g, an internal impedance ACIR (Alternate Current Internal Resistance) of 3.05 mΩ and the charge/discharge cycle number under 25 degree C. is 1505.

In No. 14, the LFP battery 60 Ah with electrolyte formula 14 has a self-extinguishing time of 14 sec/g, an internal impedance ACIR (Alternate Current Internal Resistance) of 3.18 mΩ and the charge/discharge cycle number under 25 degree C. is 1554.

In No. 15, the LFP battery 60 Ah with electrolyte formula 15 has a self-extinguishing time of 13 sec/g, an internal impedance ACIR (Alternate Current Internal Resistance) of 4.06 mΩ and the charge/discharge cycle number under 25 degree C. is 1258.

In No. 16, the LFP battery 60 Ah with electrolyte formula 16 has a self-extinguishing time of 10 sec/g, an internal impedance ACIR (Alternate Current Internal Resistance) of 2.32 mΩ and the charge/discharge cycle number under 25 degree C. is 2035.

In No. 17, the LFP battery 60 Ah with electrolyte formula 17 has a self-extinguishing time of 8 sec/g, an internal impedance ACIR (Alternate Current Internal Resistance) of 2.45 mΩ and the charge/discharge cycle number under 25 degree C. is 1906.

In No. 18, the LFP battery 60 Ah with electrolyte formula 18 has a self-extinguishing time of 14 sec/g, an internal impedance ACIR (Alternate Current Internal Resistance) of 2.63 mΩ and the charge/discharge cycle number under 25 degree C. is 1734.

In No. 19, the LFP battery 60 Ah with electrolyte formula 19 has a self-extinguishing time of 10 sec/g, an internal impedance ACIR (Alternate Current Internal Resistance) of 2.39 mΩ and the charge/discharge cycle number under 25 degree C. is 1895.

In No. 20, the LFP battery 60 Ah with electrolyte formula 20 has a self-extinguishing time of 11 sec/g, an internal impedance ACIR (Alternate Current Internal Resistance) of 2.15 mΩ and the charge/discharge cycle number under 25 degree C. is 2120.

In No. 21, the LFP battery 60 Ah with electrolyte formula 21 has a self-extinguishing time of 12 sec/g, an internal impedance ACIR (Alternate Current Internal Resistance) of 2.46 mΩ and the charge/discharge cycle number under 25 degree C. is 1887.

In No. 22, the LFP battery 60 Ah with electrolyte formula 22 has a self-extinguishing time of 13 sec/g, an internal impedance ACIR (Alternate Current Internal Resistance) of 2.43 mΩ and the charge/discharge cycle number under 25 degree C. is 1864.

In No. 23, the LFP battery 60 Ah with electrolyte formula 23 has a self-extinguishing time of 9 sec/g, an internal impedance ACIR (Alternate Current Internal Resistance) of 2.23 mΩ and the charge/discharge cycle number under 25 degree C. is 2117.

With reference to the batteries 1 to 3 in Table 10/FIG. 23A: the organic electrolyte contains 1% VC (Battery 1), which is considered as flammable electrolyte. The self-extinguishing time is 63 sec/g, and the internal impedance of the battery is 3.27 mΩ. The number of charge-discharge cycle is only 1359 cycles at the 0.5 C until reaching the capacity retention (C.R.) of 80%. By adding 1% FEC (Battery 2) and 3% EPFCP (Battery 3) in sequence, the self-extinguishing time is significantly reduced, and the long-cyclic performance of the battery tends to be slightly improved.

For Batteries 4 to 6 in FIG. 10/FIG. 23A: 1% VC, 1% FEC, and then 5% $PYR_{13}PF_6$ are added to the organic electrolyte (Battery 4), the self-extinguishing time is significantly reduced compared with that of Battery 2. By adding a high melting point, low vapor pressure ionic liquid in the electrolyte, the self-extinction ability will be significantly improved but the performance of the overall battery drops. This is because $PYR_{13}PF_6$ ionic liquid is used and $PF_6^-$ readily intercalate into the layered structure of graphite, resulting in a significant increase in the internal resistance of the relevant lithium-ion battery. In the Battery 5 2.9% HFCP is added as Stabilizer and in Battery 6 2.9% EPFCP is added as stabilizer. The self-extinguishing times of Batteries 5 and 6 are significantly reduced when comparing to Battery 4. The performance of the Batteries 5 and 6 have improved when comparing to Battery 4. Based on the test results, the addition of EPFCP as a stabilizer produce better results.

The Batteries 9 to 11 in FIG. 23A may be considered similar to Batteries 4 to 6 in FIG. 23A. By using $DiPYR_{15}(PF_6)_2$ as the ionic liquid with 2% HFCP or 2% EPFCP added as stabilizers, the self-extinguishing times of both are significantly reduced, and the performance of the Batteries have been enhanced. The use of EPFCP as a stabilizer produce better results.

For Batteries 6 to 8 om FIG. 23A, the organic electrolyte is fixed with 1% VC, 1% FEC as the film forming agents and 2.9% EPFCP, 5, 10, 15% $PYR_{13}PF_6$ respectively, or 6, 8, 10% $DiPYR_{15}(PF_6)_2$ respectively for Batteries 11 to 13. The self-extinguishing time for these batteries reduces by increasing the amount of ionic liquid added. However, the impedance value of battery increases with the amount of ionic liquid added resulting in overall battery performance. Therefore, it is important to find the optimal amount of A+B+C and it is a fine balance.

As to Batteries 11, 14 to 15 in FIG. 23A, it shows that the increase in the amount of film-forming agent VC will significantly increase the battery impedance, resulting in the poor performance.

With reference to Batteries 11 and 16 to 17 in FIG. 23A, by increasing the FEC content as the film forming agent, the self-extinguishing time is slightly reduced while the impedance value of battery remains relatively stable without significant increment. Among them, Battery 16 with 2% FEC as the film-forming agent shows best stability.

Batteries 16 in FIG. 23A, 18 to 23 in FIG. 23B show the best performance, with 1% VC, 2% FEC, 2.5~2.8% EPFCP and 6% ionic liquid added to the organic electrolyte, with ionic liquid being a dual-core cationic chain or the aromatic bonded to cation according to the invention. Among them, the range of self-extinguishing time is from 9 to 14 sec/g, which is considered as a flame-retardant electrolyte. By adding an appropriate amounts of stabilizer and ionic liquid, a uniform and dense of SEI film with low impedance can be formed on the surface of the anodes which effectively reduce the internal impedance of battery to about 2.15~2.46 mΩ, consequently enhance the performance of the overall batteries.

The invention claimed is:

1. An ionic liquid for adding to an electrolyte of a lithium-ion battery, wherein the ionic liquid comprises a compound with a dual core structure having the general formula (I):

$Z_1X_1YX_2Z_2$ (formula I), wherein $Z_1$ and $Z_2$ are selected from the group consisting of $PF_6^-$(hexafluorophosphate), $POF_2^-$(difluorophosphate), $BF_4^-$(tetrafluoroborate), $B(C_2O_4)_2^-$($BOB^-$, bis (oxalato) borate), $BF_2(C_2O_4)^-$($ODFB^-$, difluoro(oxalato)borate), $CF_3BF_3^-$(trifluoromethyltrifluoroborate), $(FSO_2)_2N^-$($FSI^-$, bis(fluorosulfonyl)imide), $(CF_3SO_2)_2N^-$($TFSI^-$, bis(trifluoromethane)sulfonamide), $CH_3SO_4^-$($MeSO_4^-$, methyl sulfate) and

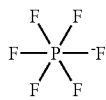

wherein $X_1YX_2$ is selected from the group consisting of

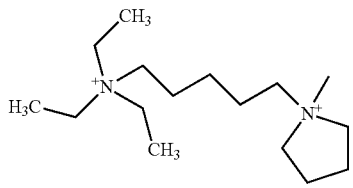 [SMILES: CC[N+](CC)(CC)CCCCC[N+]1(C)CCCC1]

1,5-[(1-methylpyrrolidium 1-yl) (triethylamine N-yl)] pentane

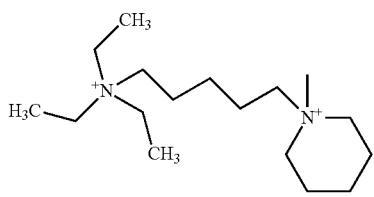 [SMILES: CC[N+](CC)(CC)CCCCC[N+]1(C)CCCCC1]

1,5-[(1-methylpiperidinium 1-yl) (triethylamine N-yl)] pentane

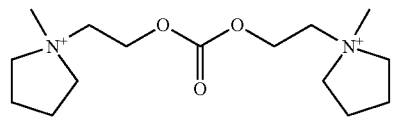 [SMILES: C[N+]1(CCOC(=O)OCC[N+]2(C)CCCC2)CCCC1]

Bis [2-(1-methylpyrrolidinium 1-yl) ethyl] carbonate

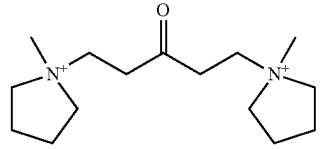 [SMILES: C[N+]1(CCC(=O)CC[N+]2(C)CCCC2)CCCC1]

1,5-Bis(1-methylpyrrolidinium 1-yl) pentan-3-one and

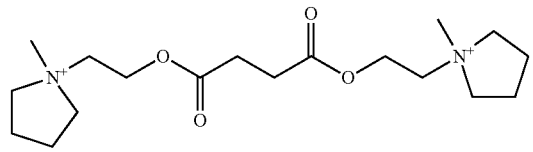 [SMILES: C[N+]1(CCOC(=O)CCC(=O)OCC[N+]2(C)CCCC2)CCCC1]

Bis[2-(1-methylpyrrolidinium 1-yl) ethyl] butanedioate
wherein an overall amount of ionic liquid added to the electrolyte is 0.1-15 wt. %.

2. A lithium ion battery comprising a positive electrode, a negative electrode, a separator, an electrolyte and one or more ionic liquid as claimed in claim 1.

3. The lithium ion battery as claimed in claim 2 further comprising a stabilizer, wherein the stabilizer is a cyclophosphazene compound.

4. The lithium ion battery as claimed in claim 3, wherein the stabilizer is selected from the group consisting of:

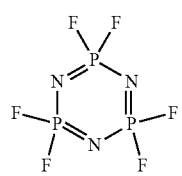

Hexafluoro cyclotriphosphazene; and

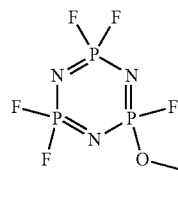

Ethoxy (pentafluoro) cyclotriphosphazene.

5. The lithium ion battery as claimed in claim 3, wherein an amount of the stabilizer added to the electrolyte is 0.1-2.9 wt. %.

6. The lithium ion battery as claimed in claim 2, wherein a SEI film forming agent is added to the electrolyte.

7. The lithium ion battery as claimed in claim 6, wherein the SEI film forming agent is selected from the group consisting of fluoroethylene carbonate (FEC), vinylene carbonate (VC), vinyl ethylene carbonate (VEC), ethylene sulfite (ES), propylene sulfite (PS), and ethylene sulfate (DTD), and combinations thereof.

8. The lithium ion battery as claimed in claim 6, wherein an amount of the SEI film forming agent added to the electrolyte is 0.1-5 wt. %.

9. The lithium ion battery as claimed in claim 2, wherein the electrolyte is a non-aqueous electrolyte; wherein optionally, the non-aqueous electrolyte comprises a lithium salt selected from the group consisting of $LiPF_6$, $LiClO_4$, $LiBF_4$, $LiSO_3CF_3$, $LiN(SO_2F)_2$, $LiN(SO_2CF_3)_2$, $LiN(SO_2CF_2CF_3)_2$, $LiAsF_6$, $LiAlCl_4$, $LiNO_3$, $LiPOF_2$, $LiB(C_2O_4)_2$, $LiBF_2(C_2O_4)$, $LiCF_3BF_3$, and combinations thereof; and
wherein optionally, a concentration of the lithium salt in the electrolyte is 0.5~1.5 mol/L.

10. The lithium ion battery as claimed in claim 9, wherein the nonauqeous electrolyte comprises an organic solvent selected from the group consisting of carbonate, carboxylate, ether, ketone, and combinations thereof;
wherein optionally, the carbonate is selected from the group consisting of ethylene carbonate (EC), propylene carbonate (PC), diethyl carbonate (DEC), methyl ethyl carbonate (EMC), dimethyl carbonate (DMC), dipropyl carbonate, dibutyl carbonate, and a combination thereof;
wherein optionally, the carboxylate is carboxylic acid ester;
wherein optionally, the carboxylic acid ester comprises at least one of methyl acetate, ethyl acetate, methyl butyrate, ethyl butyrate, methyl propionate, ethyl propionate and propyl acetate, and a combination thereof; and
wherein optionally, the positive electrode comprises an active material being which is a lithium metal complex oxide compound.

11. The lithium ion battery as claimed in claim 10, wherein a metal element of the lithium metal complex oxide is selected from the group consisting of a transition metal and a non-transition metal;
wherein optionally, the transition metal is selected from the group consisting of vanadium, titanium, chromium, copper, iron, nickel and cobalt; and
wherein optionally, the non-transition metal is selected from the group consisting of aluminum and manganese.

12. The lithium ion battery as claimed in claim 2, wherein the negative electrode comprises an active material selected from the group consisting of soft carbon, hard carbon, artificial graphite, natural graphite, meso carbon micro bead (MCMB), silicon, silicon oxide compounds, silicon carbon composites, lithium titanate oxide, and metals that form alloys with lithium;
wherein optionally, the negative electrode comprises an active material that is carbon-based, silicon-based or tin-based;
wherein optionally, the separator comprises a membrane; and
wherein optionally, the membrane comprises a material selected from the group consisting of polyethylene (PE), polypropylene (PP), polyvinylidene fluoride (PVDF), ceramic material, glass fiber and combinations thereof.

\* \* \* \* \*